(12) United States Patent
Nakatani et al.

(10) Patent No.: US 6,522,912 B1
(45) Date of Patent: Feb. 18, 2003

(54) EAR TYPE THERMOMETER

(75) Inventors: Naofumi Nakatani, Osaka (JP); Keiko Noda, Osaka (JP); Hirofumi Inui, Osaka (JP); Kazuko Awaya, Hirakata (JP); Kiyoshi Kanazawa, Katano (JP); Hirohisa Imai, Nara (JP)

(73) Assignee: Matsushita Electric Industrial Co., Ltd. (JP)

( * ) Notice: Subject to any disclaimer, the term of this patent is extended or adjusted under 35 U.S.C. 154(b) by 0 days.

(21) Appl. No.: 09/674,732

(22) PCT Filed: Apr. 30, 1999

(86) PCT No.: PCT/JP99/02327

§ 371 (c)(1),
(2), (4) Date: Jan. 16, 2001

(87) PCT Pub. No.: WO99/56629

PCT Pub. Date: Nov. 11, 1999

(30) Foreign Application Priority Data

| May 6, 1998 | (JP) | 10-123176 |
| May 6, 1998 | (JP) | 10-123177 |
| May 6, 1998 | (JP) | 10-123178 |
| Jun. 29, 1998 | (JP) | 10181843 |

(51) Int. Cl.[7] .............................................. A61B 10/00
(52) U.S. Cl. ...................... 600/474; 600/549; 374/121; 374/130
(58) Field of Search ................................ 600/474, 549; 374/121, 129, 130

(56) References Cited

U.S. PATENT DOCUMENTS

| 3,530,718 A | 9/1970 | Ehlo ............................ 73/362 |
| 4,151,831 A | 5/1979 | Lester ......................... 128/736 |
| 4,648,055 A | 3/1987 | Ishizaka et al. ............. 364/557 |
| 4,784,149 A | 11/1988 | Berman et al. ............. 128/664 |
| 4,993,419 A | * 2/1991 | Pompei et al. .............. 374/130 |
| 5,015,102 A | 5/1991 | Yamaguchi .................. 374/107 |
| 5,199,436 A | * 4/1993 | Pompei et al. .............. 600/474 |
| 5,246,292 A | * 9/1993 | Gal et al. ..................... 374/121 |
| 5,333,784 A | 8/1994 | Pompei ..................... 236/91 C |
| 5,445,158 A | * 8/1995 | Pompei ....................... 600/474 |
| 5,653,238 A | 8/1997 | Pompei ....................... 128/664 |
| 5,685,319 A | 11/1997 | Marett ........................ 128/738 |

FOREIGN PATENT DOCUMENTS

| DE | 42 04 429 A1 | 8/1993 |
| DE | 195 24 966 A1 | 1/1997 |
| EP | 0 502 277 A2 | 9/1992 |
| EP | 0 572 095 A1 | 12/1993 |
| GB | 2 293 243 A | 3/1996 |
| JP | 57-185049 | 11/1982 |
| JP | 60-6835 A | 1/1985 |
| JP | 62-183807 A | 8/1987 |
| JP | 5-269088 A | 10/1993 |
| JP | 6-165 A | 1/1994 |
| JP | 6-63851 | 8/1994 |
| JP | 6-285028 A | 10/1994 |
| JP | 7-155296 | 6/1995 |
| JP | 8-56909 A | 3/1996 |
| JP | 8-107884 A | 4/1996 |
| JP | 8-275924 A | 10/1996 |
| JP | 10-75934 A | 3/1998 |

* cited by examiner

*Primary Examiner*—Patrick Brinson
(74) *Attorney, Agent, or Firm*—Rossi & Associates

(57) ABSTRACT

A thermometer for measuring a body temperature by using infrared rays and on the basis of a measuring method in which a measurement error fluctuates depending upon the length of the measuring time including computation time. The measuring time is calculated on the basis of a required measurement error, so that a temperature can be measured in a suitable time corresponding to a required allowable error. A probe is formed of a porous structure so as to improve the heat insulating effect thereof, and an auxiliary adapter is provided to permit the thermometer to be fitted better in the earhole in spite of an individual difference in size thereof with the function of reporting a relative ovulation date based on a desired delivery date also incorporated in the thermometer.

42 Claims, 48 Drawing Sheets

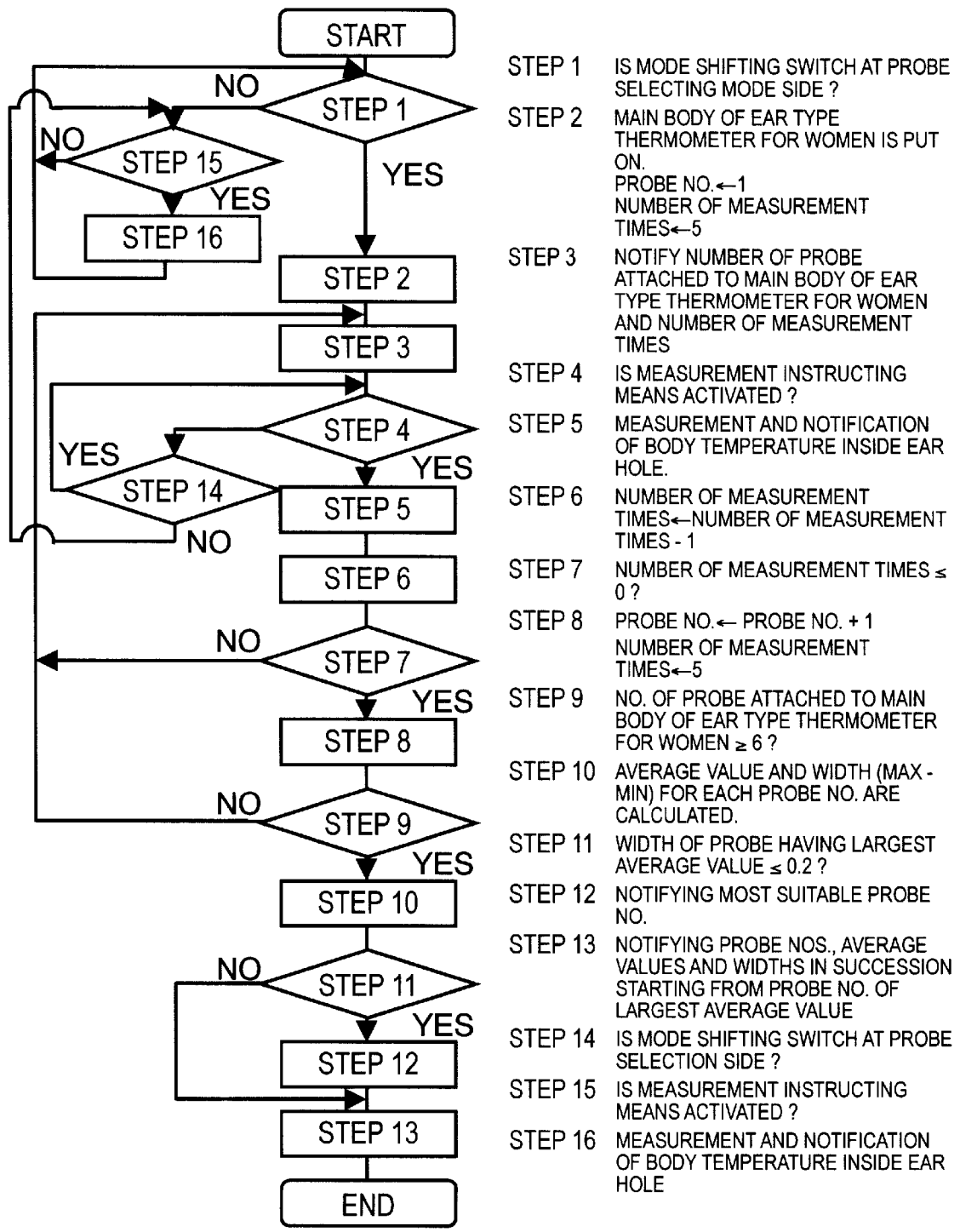

STEP 1  IS MODE SHIFTING SWITCH AT PROBE SELECTING MODE SIDE ?
STEP 2  MAIN BODY OF EAR TYPE THERMOMETER FOR WOMEN IS PUT ON.
PROBE NO.←1
NUMBER OF MEASUREMENT TIMES←5
STEP 3  NOTIFY NUMBER OF PROBE ATTACHED TO MAIN BODY OF EAR TYPE THERMOMETER FOR WOMEN AND NUMBER OF MEASUREMENT TIMES
STEP 4  IS MEASUREMENT INSTRUCTING MEANS ACTIVATED ?
STEP 5  MEASUREMENT AND NOTIFICATION OF BODY TEMPERATURE INSIDE EAR HOLE.
STEP 6  NUMBER OF MEASUREMENT TIMES←NUMBER OF MEASUREMENT TIMES - 1
STEP 7  NUMBER OF MEASUREMENT TIMES ≤ 0 ?
STEP 8  PROBE NO.← PROBE NO. + 1
NUMBER OF MEASUREMENT TIMES←5
STEP 9  NO. OF PROBE ATTACHED TO MAIN BODY OF EAR TYPE THERMOMETER FOR WOMEN ≥ 6 ?
STEP 10  AVERAGE VALUE AND WIDTH (MAX - MIN) FOR EACH PROBE NO. ARE CALCULATED.
STEP 11  WIDTH OF PROBE HAVING LARGEST AVERAGE VALUE ≤ 0.2 ?
STEP 12  NOTIFYING MOST SUITABLE PROBE NO.
STEP 13  NOTIFYING PROBE NOS., AVERAGE VALUES AND WIDTHS IN SUCCESSION STARTING FROM PROBE NO. OF LARGEST AVERAGE VALUE
STEP 14  IS MODE SHIFTING SWITCH AT PROBE SELECTION SIDE ?
STEP 15  IS MEASUREMENT INSTRUCTING MEANS ACTIVATED ?
STEP 16  MEASUREMENT AND NOTIFICATION OF BODY TEMPERATURE INSIDE EAR HOLE

FIG. 53

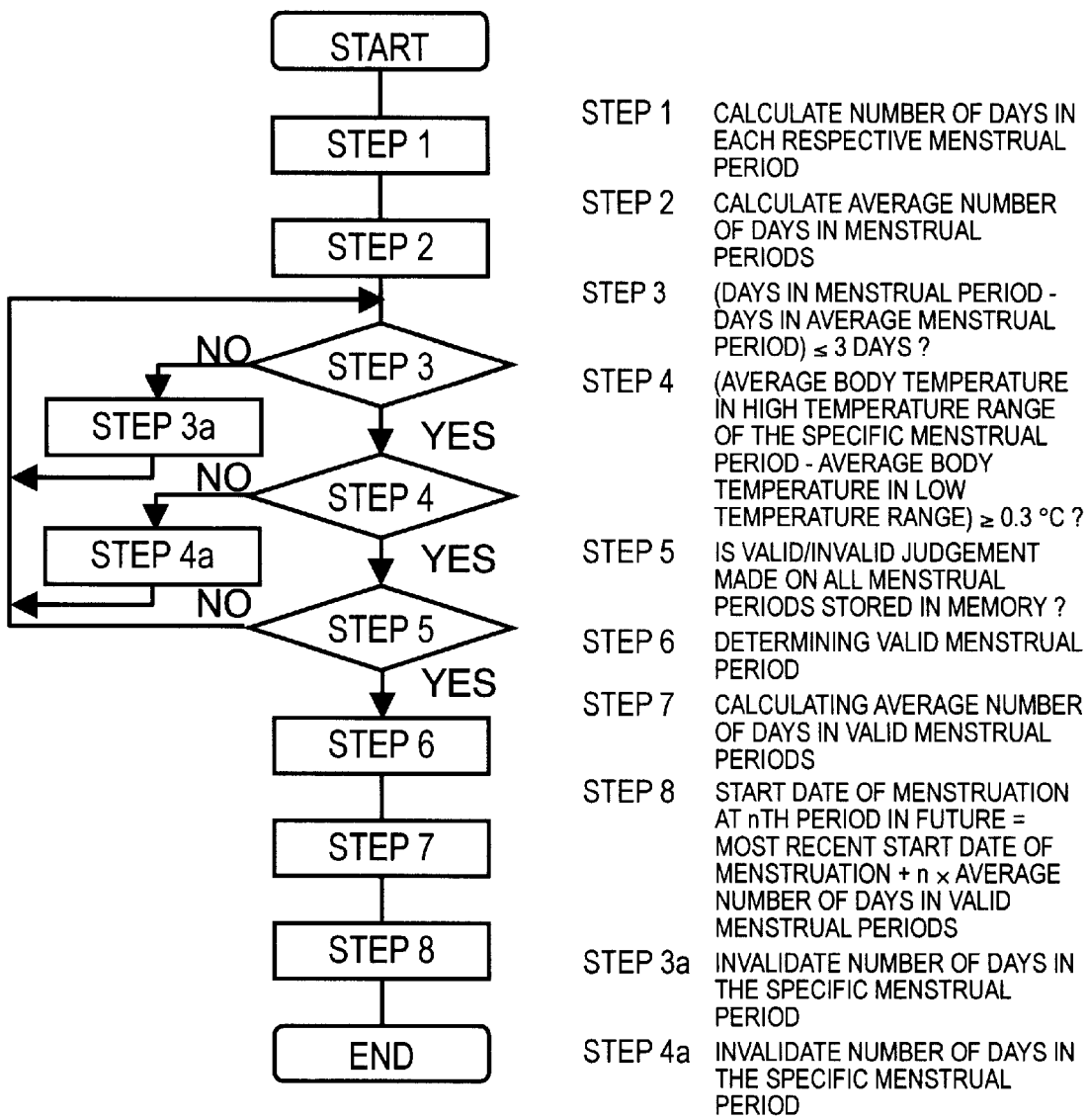

STEP 1  CALCULATE NUMBER OF DAYS IN EACH RESPECTIVE MENSTRUAL PERIOD
STEP 2  CALCULATE AVERAGE NUMBER OF DAYS IN MENSTRUAL PERIODS
STEP 3  (DAYS IN MENSTRUAL PERIOD - DAYS IN AVERAGE MENSTRUAL PERIOD) ≤ 3 DAYS ?
STEP 4  (AVERAGE BODY TEMPERATURE IN HIGH TEMPERATURE RANGE OF THE SPECIFIC MENSTRUAL PERIOD - AVERAGE BODY TEMPERATURE IN LOW TEMPERATURE RANGE) ≥ 0.3 °C ?
STEP 5  IS VALID/INVALID JUDGEMENT MADE ON ALL MENSTRUAL PERIODS STORED IN MEMORY ?
STEP 6  DETERMINING VALID MENSTRUAL PERIOD
STEP 7  CALCULATING AVERAGE NUMBER OF DAYS IN VALID MENSTRUAL PERIODS
STEP 8  START DATE OF MENSTRUATION AT nTH PERIOD IN FUTURE = MOST RECENT START DATE OF MENSTRUATION + n × AVERAGE NUMBER OF DAYS IN VALID MENSTRUAL PERIODS
STEP 3a  INVALIDATE NUMBER OF DAYS IN THE SPECIFIC MENSTRUAL PERIOD
STEP 4a  INVALIDATE NUMBER OF DAYS IN THE SPECIFIC MENSTRUAL PERIOD

FIG. 54

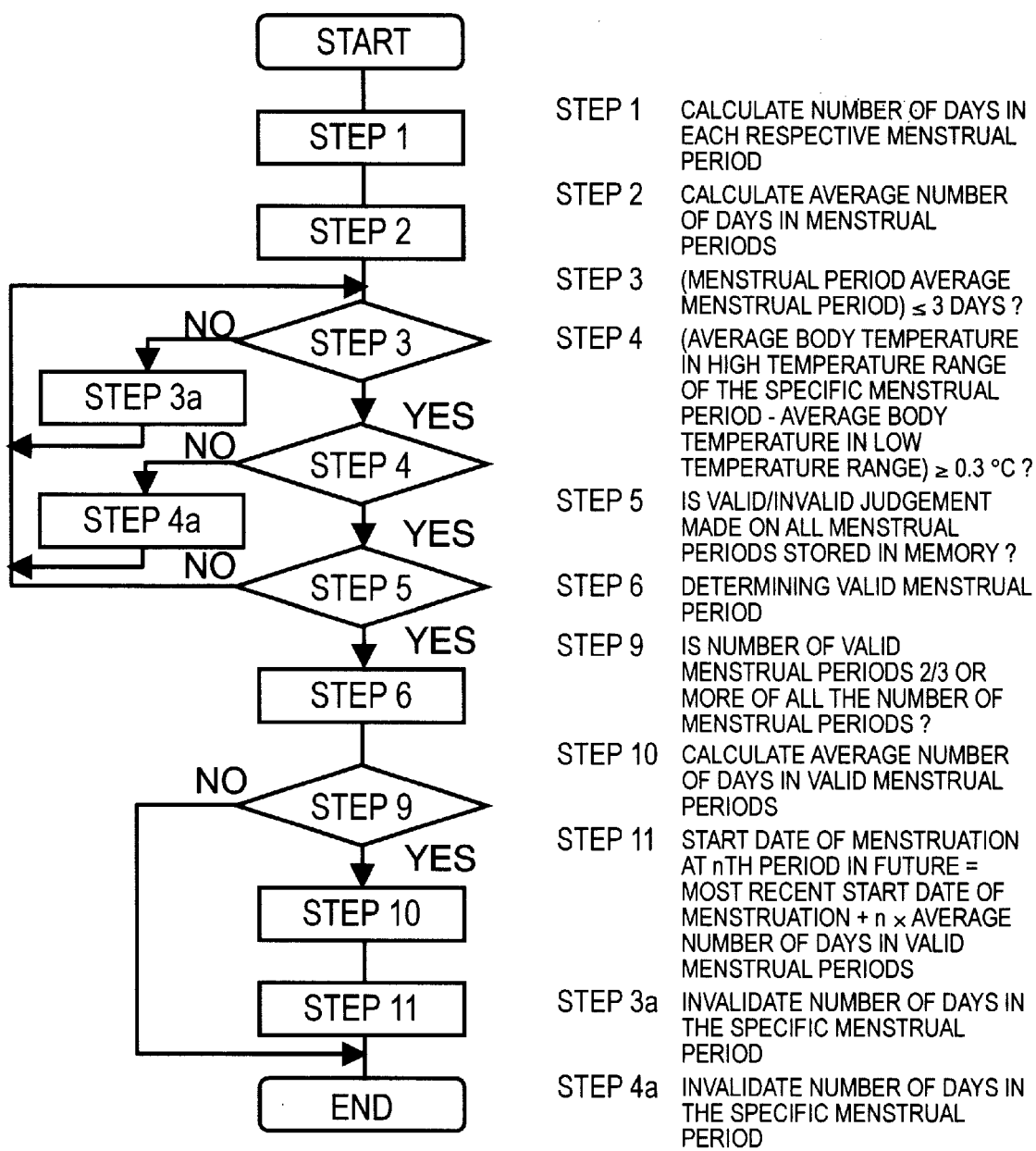

STEP 1    CALCULATE NUMBER OF DAYS IN EACH RESPECTIVE MENSTRUAL PERIOD
STEP 2    CALCULATE AVERAGE NUMBER OF DAYS IN MENSTRUAL PERIODS
STEP 3    (MENSTRUAL PERIOD AVERAGE MENSTRUAL PERIOD) ≤ 3 DAYS ?
STEP 4    (AVERAGE BODY TEMPERATURE IN HIGH TEMPERATURE RANGE OF THE SPECIFIC MENSTRUAL PERIOD - AVERAGE BODY TEMPERATURE IN LOW TEMPERATURE RANGE) ≥ 0.3 °C ?
STEP 5    IS VALID/INVALID JUDGEMENT MADE ON ALL MENSTRUAL PERIODS STORED IN MEMORY ?
STEP 6    DETERMINING VALID MENSTRUAL PERIOD
STEP 9    IS NUMBER OF VALID MENSTRUAL PERIODS 2/3 OR MORE OF ALL THE NUMBER OF MENSTRUAL PERIODS ?
STEP 10   CALCULATE AVERAGE NUMBER OF DAYS IN VALID MENSTRUAL PERIODS
STEP 11   START DATE OF MENSTRUATION AT nTH PERIOD IN FUTURE = MOST RECENT START DATE OF MENSTRUATION + n × AVERAGE NUMBER OF DAYS IN VALID MENSTRUAL PERIODS
STEP 3a   INVALIDATE NUMBER OF DAYS IN THE SPECIFIC MENSTRUAL PERIOD
STEP 4a   INVALIDATE NUMBER OF DAYS IN THE SPECIFIC MENSTRUAL PERIOD

FIG. 55

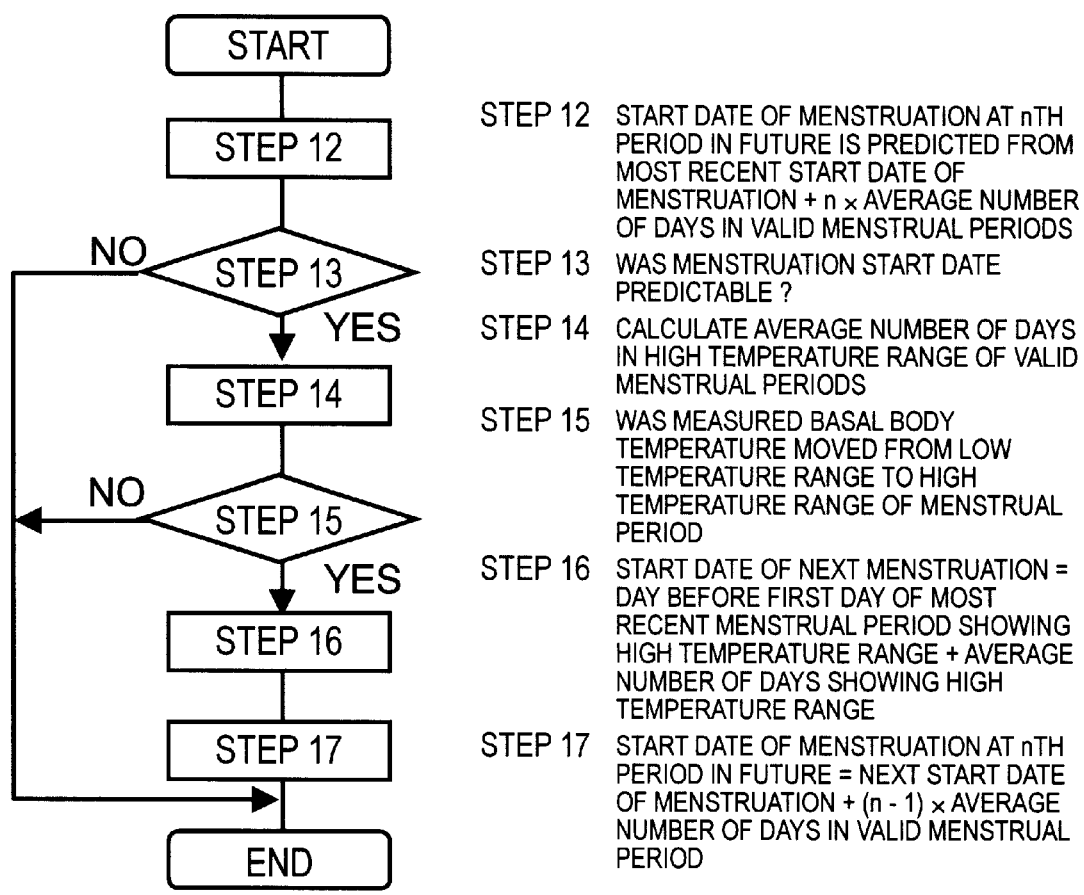

STEP 12  START DATE OF MENSTRUATION AT nTH PERIOD IN FUTURE IS PREDICTED FROM MOST RECENT START DATE OF MENSTRUATION + n × AVERAGE NUMBER OF DAYS IN VALID MENSTRUAL PERIODS

STEP 13  WAS MENSTRUATION START DATE PREDICTABLE ?

STEP 14  CALCULATE AVERAGE NUMBER OF DAYS IN HIGH TEMPERATURE RANGE OF VALID MENSTRUAL PERIODS

STEP 15  WAS MEASURED BASAL BODY TEMPERATURE MOVED FROM LOW TEMPERATURE RANGE TO HIGH TEMPERATURE RANGE OF MENSTRUAL PERIOD

STEP 16  START DATE OF NEXT MENSTRUATION = DAY BEFORE FIRST DAY OF MOST RECENT MENSTRUAL PERIOD SHOWING HIGH TEMPERATURE RANGE + AVERAGE NUMBER OF DAYS SHOWING HIGH TEMPERATURE RANGE

STEP 17  START DATE OF MENSTRUATION AT nTH PERIOD IN FUTURE = NEXT START DATE OF MENSTRUATION + (n - 1) × AVERAGE NUMBER OF DAYS IN VALID MENSTRUAL PERIOD

FIG. 57

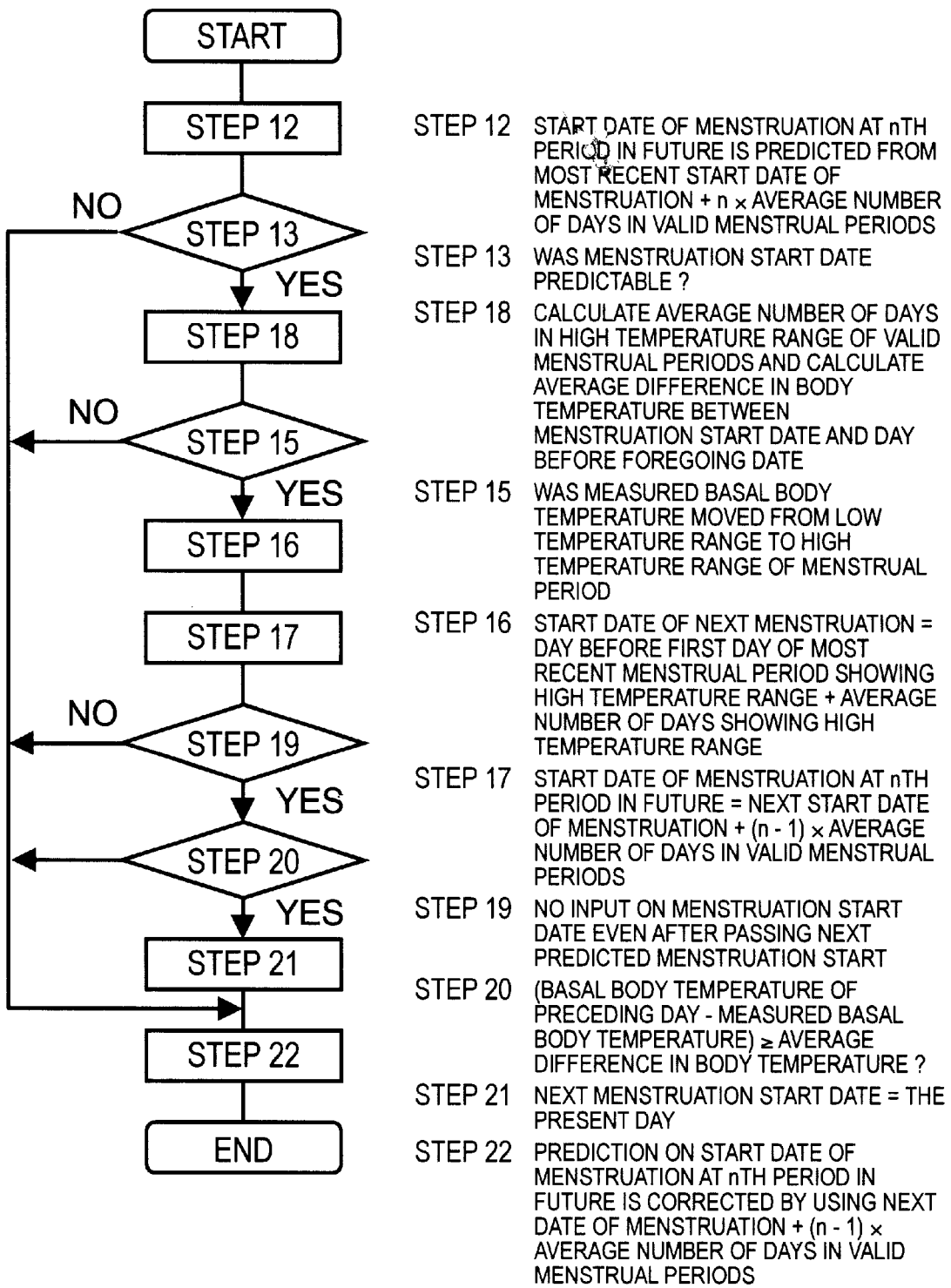

STEP 12 START DATE OF MENSTRUATION AT nTH PERIOD IN FUTURE IS PREDICTED FROM MOST RECENT START DATE OF MENSTRUATION + n × AVERAGE NUMBER OF DAYS IN VALID MENSTRUAL PERIODS

STEP 13 WAS MENSTRUATION START DATE PREDICTABLE ?

STEP 18 CALCULATE AVERAGE NUMBER OF DAYS IN HIGH TEMPERATURE RANGE OF VALID MENSTRUAL PERIODS AND CALCULATE AVERAGE DIFFERENCE IN BODY TEMPERATURE BETWEEN MENSTRUATION START DATE AND DAY BEFORE FOREGOING DATE

STEP 15 WAS MEASURED BASAL BODY TEMPERATURE MOVED FROM LOW TEMPERATURE RANGE TO HIGH TEMPERATURE RANGE OF MENSTRUATION PERIOD

STEP 16 START DATE OF NEXT MENSTRUATION = DAY BEFORE FIRST DAY OF MOST RECENT MENSTRUAL PERIOD SHOWING HIGH TEMPERATURE RANGE + AVERAGE NUMBER OF DAYS SHOWING HIGH TEMPERATURE RANGE

STEP 17 START DATE OF MENSTRUATION AT nTH PERIOD IN FUTURE = NEXT START DATE OF MENSTRUATION + (n - 1) × AVERAGE NUMBER OF DAYS IN VALID MENSTRUAL PERIODS

STEP 19 NO INPUT ON MENSTRUATION START DATE EVEN AFTER PASSING NEXT PREDICTED MENSTRUATION START

STEP 20 (BASAL BODY TEMPERATURE OF PRECEDING DAY - MEASURED BASAL BODY TEMPERATURE) ≥ AVERAGE DIFFERENCE IN BODY TEMPERATURE ?

STEP 21 NEXT MENSTRUATION START DATE = THE PRESENT DAY

STEP 22 PREDICTION ON START DATE OF MENSTRUATION AT nTH PERIOD IN FUTURE IS CORRECTED BY USING NEXT DATE OF MENSTRUATION + (n - 1) × AVERAGE NUMBER OF DAYS IN VALID MENSTRUAL PERIODS

EAR TYPE THERMOMETER

TECHNICAL FIELD

The present invention relates to an ear type thermometer for women, which utilizes infrared rays radiated from an eardrum to measure body temperatures, thereby enhancing the measurement accuracy of the ear type thermometer for women.

BACKGROUND ART

An ear type thermometer, whereby infrared rays radiated from an eardrum are detected and a non-contact measurement of the eardrum temperature is carried out, is generally like what is described in the Japanese Patent Unexamined Application No. S 60-6835.

The ear type thermometer of above is structured as FIG. 60 shows and operates as follows:

First, the infrared rays radiated from an eardrum 200, the temperature of which is to be measured, are incident intermittently on a pyroelectric infrared sensor 202 as a chopper 201 interrupts the infrared rays, thereby converting the infrared rays to an electrical signal that varies in output with the same frequency as the operating frequency of the chopper 201. Next, after amplification in an amplifier circuit 203 and rectification in a synchronous detector circuit 204, the electrical signal is changed to a DC via a filter circuit 205 formed of low-pass filters. The value gained as an output signal from the filter circuit 205 represents a measurement value of the infrared rays corresponding to the temperature of the eardrum 200. On the other hand, the temperature of the chopper 201 is measured in advance by using a sensor temperature measuring means 206 formed of a thermister. The temperature of the chopper 201 thus obtained is used as a temperature compensating signal when the temperature of the eardrum 200 is derived by calculation from the output signal of the filter circuit 205.

Finally, a body temperature calculating means 207 reads the temperature of the chopper 201 and also the measured value of infrared rays obtained as an output signal of the filter circuit 205, thereby deriving by calculation the temperature of the eardrum 200 from the readout. The foregoing calculation to derive the temperature of the eardrum 200 is based on an assumption that the value obtained as an output signal form the filter circuit 205, i.e., a value tantamount to the output of the pyroelectric infrared sensor is proportionate to the difference between the fourth, power of the absolute temperature of the eardrum 200 and the fourth power of the absolute temperature of the chopper 201. However, when the ambient temperature range and also the measurement temperature range, in which an ear type thermometer is used, is narrow, almost the same result can be obtained in calculating the temperature of the eardrum 200 by assuming that the amplitude of the output signal from the pyroelectric sensor 202 is proportionate to the difference between the absolute temperature of the eardrum 200 and the absolute temperature of the chopper 201.

In addition, the magnitude of an error included in the temperature of the eardrum thus derived by calculation has not been allowed to be designated by the user as a permissible error but has been determined in advance as one of the specification items of an ear type thermometer itself.

Furthermore, an eardrum is located toward the back of an external auditory miatus and it is known that the temperature of the external auditory miatus is lower than the temperature of the eardrum by 0.5° C. to 1° C. Consequently, it is difficult to obtain a consistent measurement result at the time of measuring body temperatures unless only the infrared rays radiated from an eardrum are accurately measured, eliminating the effects of the infrared rays radiated from other areas of the external auditory miatus than the area where the eardrum is located.

In order to deal with the problems as described above, a proposal is made on a technology whereby temperatures are measured at a plurality of points on the surface in an ear hole formed of an external auditory miatus and the eardrum and the highest value in the temperatures measured is considered as the temperature of the eardrum. (Refer to the Japanese Patent Unexamined Application No. H6-285028 and the Japanese Patent Unexamined Application No. H8-275924.)

FIG. 61 is a diagram to illustrate the principle whereby temperatures of an eardrum are measured with a conventional ear type thermometer. In FIG. 61, the reference numeral 211 is an optical vision of the ear type thermometer, reference numeral 212 is an external auditory miatus, reference numeral 213 is the eardrum and reference numeral 214 is a probe acting as an inlet for infrared rays to reach the ear type thermometer.

With the foregoing ear type thermometer, by narrowing down the optical vision 211 for receiving infrared rays, only the infrared rays radiated from a minute area on the ear hole surface formed of the external auditory miatus 212 and eardrum 213 are captured to allow the temperature of the specific area to be measured and also to allow the temperatures at a plurality of positions on the eardrum surface to be measured while changing the direction of the opptical vision 211 by altering the direction of the probe 214 within the external auditory miatus 212, thereby treating the highest temperature obtained from above measurements as the temperature of the eardrum 213.

As the flow chart in FIG. 62 shows, the method for determining the highest value in temperatures measured comprises an infrared measurement process whereby infrared rays radiated from a spot captured in the optical vision 211 are measured and a computation process, whereby the temperature of the foregoing spot is derived by calculation according to the measured value of the infrared rays and the highest value in temperature that has been obtained by calculation by that time is updated, wherein these two processes are repeated.

As referred to in the Japanese Patent Unexamined Application No. H6-285028, it is conceivable theoretically to utilize a special-purpose table during the foregoing computation process, the special-purpose table being intended for deriving a body temperature from the measured value of infrared rays. However, the table of that kind tends to become enormous and, therefore, as described in the Japanese Patent Unexamined Publication No. H6-63851, a computation formula as expressed below is used.

$$T = \sqrt[4]{T_a^4 + \frac{V_s}{f(T_a)}} \qquad (1)$$

where T is a body temperature of the eardrum expressed in kelvins (K), Ta is an ambient temperature in kelvins (K), in which the ear type thermometer is used, and Vs is an output voltage of the infrared sensor.

Here, f(Ta) is a correcting term corresponding to the temperature characteristics of the infrared sensor and it is known that this can be expressed in practice by a second order polynomial expression as follows:

$$f(T_a) = A \times T_a^2 + B \times T_a + C \quad (2)$$

where A, B and C are constants.

Depending on the situations where the body temperature at the eardrum is higher than the ambient temperature and vice versa, Vs may be a positive value or a negative value. Usually, the sign of Vs is made positive when the body temperature at the eardrum is higher than the ambient temperature and made negative when the body temperature at the eardrum is lower than the ambient temperature. At this time, f(Ta) becomes always a positive value regardless of the value of Ta. In the vicinity of a room temperature, a variation of f(Ta) per the change of 1° C. in the ambient temperature Ta, namely, $$\frac{f(T_a + 1) - f(T_a)}{f(T_a)} \quad (3)$$

is about 0.2%.

Recently, more and more women go into the workaday world and there are many women who leave their children at a day-care facility and work at office or factory. For a working woman, it is important to know when to give birth to a baby because it is closely related to the schedules of her work, her putting out a baby to nurse after the baby is born, her doing things while she is pregnant and the like. Even for house wives, it is desirable to plan ahead well for delivery in consideration of a delicate relation between a seasons and physical conditions of theirs.

As a simple means to satisfy the foregoing needs, there is a thermometer for women with a function allowing a woman to know the date when her baby is due in advance by entering necessary data. More specifically this thermometer for women has the function of determining whether a woman in question is pregnant or not by having a menstruation start date and a basal body temperature entered manually or automatically and notifying an expected delivery date. When this thermometer for women is used, the user is allowed to know the expected delivery date before she is informed of the expected delivery date at hospital.

Furthermore, there once existed a thermometer for women to predict and notify a start date of the next menstruation obtained by adding an average number of days in a menstrual period to the most recent menstruation start date, the number of days in each respective menstrual period being derived from the time interval between the menstruation start dates entered into a menstruation start date entering means. There also existed a thermometer for women to predict and notify a start date of the next menstruation obtained by adding 12 days (the 14th day counted from the first day of a high temperature range) to the date at the time when shifting from a low temperature range to a high temperature range is confirmed to have taken place, (the foregoing time corresponding to the time when the basal body temperature determined as being in the high temperature range continues for three days). (Refer to the Japanese Patent Unexamined Publication No. S 62-183807.) The magnitude of a tolerance on the measurement value of an ear type thermometer and how quickly the body temperature has to be measured by the ear type thermometer are determined according to the application purpose of the ear type thermometer.

A thermometer for measuring body temperatures in such a short time as a few seconds or so with a rated accuracy of about ±0.1°C. is already available in the market as a radiation thermometer as it is commonly called. Suppose a situation where such an ear type thermometer is used in measuring body temperatures of babies and infants at the time when they are sick and feverish. A tolerance on the temperature measurement value of ±0.1° C. is good enough and, in addition, the measurement of body temperatures being finished in such a short time as a few seconds is a great benefit to babies and infants who are not likely to stay quiet. On the other hand, when it comes to using the ear type thermometer as an ear type thermometer for women to measure women's basal body temperatures, it is more important for the thermometer to reduce the tolerance on the temperature measurement value to the limit established by an Act on Metric, i.e., ±0.05° C. at the maximum, for example, even if the time required for temperature measurement may increase by an order of magnitude.

Thus, when the ear type thermometer is used as an ear type thermometer for women, the extent of tolerance on the temperature measurement value and the length of time allowable for temperature measurement vary.

However, with the conventional ear type thermometer, a temperature measurement has been carried out with a given constant tolerance imposed on the measurement value and a given constant time spent in the temperature measurement regardless of the user's wish about tolerance on the measurement value and the time period to be spent in temperature measurement.

Furthermore, in consideration of a body temperature determination procedure whereby temperatures are measured at a plurality of spots on the ear hole surface formed of an external auditory miatus and an eardrum and the fact that the highest value in the temperature measurement is taken as the temperature of the eardrum, suppose a situation where an ear type thermometer is put to use actually. In order to measure the temperature of the eardrum accurately, the direction of a probe has to be changed to some extent and the optical vision of the probe needs to be momentarily headed exactly in the direction of the eardrum. In addition, it is required of the probe not to change its direction too much during respective periods of body temperature measurement, thereby allowing an almost constant amount of infrared rays to enter into the probe.

As the method to satisfy both conditions of above is easily thought of a method for urging the user to change the probe direction by generating a signal such as sounding a buzzer and the like every time when the respective temperature measurements are finished while keeping the probe in a standstill during each respective body temperature measurement period, for example.

If ease of handling on the part of the user is taken into consideration, however, the utmost of what is required by the user in using an ear type thermometer is preferably something like rotating the probe round and round continuously in the external auditory miatus without being bothered with the timing in motion of the ear type thermometer.

On an assumption that the foregoing handling would take place, a series of processes from an infrared measurement process to a computing process are required to be finished in the shortest possible time. The reason is that, as the time of the foregoing processes is extended, the distance for the optical vision of an ear type thermometer to travel during the time of above becomes longer, thereby creating a greater possibility for the optical vision to end up with hitting other areas than the eardrum at the end of the travel notwithstanding hitting just the eardrum in the beginning. In other words, on an assumption that the user would handle the ear type thermometer in this manner, unless the time required to perform the series of processes is made as short as possible, the essential point of the technology featuring a selection of the highest value among a plurality of measurement values in body temperature is in danger of negation of the effectiveness thereof.

The ear type thermometers so far proposed, however, present the problem of an unnecessarily long period for a computing process since a body temperature itself is derived by calculation in the computing process every time when an infrared measurement is carried out.

More specifically, the computation of the computation formula (1) involves a biquadratic root calculation including mathematical computations to require a long computation time in comparison with the four fundamental operations of arithmetic, resulting in a long time needed in the computing process.

A thermister is usually used in measuring the ambient temperature Ta and the ambient temperature Ta in kelvins (K) is derived by calculation from thermister resistance Rth as follows:

$$T_a = \frac{1}{\frac{\log\left(\frac{R_{th}}{R_0}\right)}{B} + \frac{1}{T_0}} \qquad (4)$$

where B, Ro and To are constants determined according to the physical properties of the thermistor.

However, in deriving by calculation the ambient temperature Ta as above, complex mathematical computations of a logarithmic calculation are involved, thereby ending up with requiring a much longer time in the computing process.

In order for these mathematical computations to be performed at a high speed, the use of hardware having a high speed computation processing capability such as a digital signal processor and the like is possible, but in that case the power consumption of an ear type thermometer that is assumed to be battery operated is inadvertently increased, resulting in creating another problem.

In addition, an ear type thermometer of the conventional structure uses a probe of a given unified size, thereby presenting a problem of an inability to perform a not necessarily accurate measurement of body temperatures.

More specifically, the size of an external auditory miatus is different between adult and child and between male and female. Further, the way a curvature of an external auditory miatus is formed differs from person to person. Therefore, when a probe of a unified outline dimension is used by a variety of people, the sense of fitting differs between individuals, resulting in a different insertion position of the probe from time to time in use and in degraded reliability of measurement values. Another problem is that a mother sets the probe by insertion in an ear hole of children and infants when an ear type thermometer is used to measure body temperatures, for example, but the mother can not figure out how deep the probe is inserted in the ear hole.

When a measurement is carried out correctly, an eardrum temperature reflects a truer body temperature in comparison with the body temperatures measured under a tongue or an armpit that is exposed to outside air at the time of temperature measurement. However, the configurations of an external auditory miatus of the human body are greatly different from person to person in diameter and straightness. Therefore, when the probe of an ear type thermometer is not fitting well with the external auditory miatus, the vision of the probe has a great difficulty in hitting the eardrum just by having the probe inserted into the ear hole, resulting in measurement of the temperature of the external auditory miatus, which is lower than the eardrum temperature, and in a failure in measuring correctly the eardrum temperature. When the temperature of the external auditory miatus is measured, suppose the room temperature happens to be low. Then, the external auditory miatus is cooled by outside air or by the inserted probe of a low temperature. As a result, the temperature picked up by the probe becomes lower than the correct temperature due to the adverse effect of low room temperature and the repeatability of the temperature measurement is degraded. A conventional ear type thermometer is just provided with a plurality of probes and the user only selects one of the probes according to her own judgement about probe selection, relying on her sense of fitting and the like. Therefore, there has not been any assurance that the probe selected by the user allows a correct measurement of eardrum temperatures to be performed.

Further, a conventional thermometer for women is just intended for enabling the expected delivery date to be found out after pregnancy, thereby presenting a problem of insufficient functions made available for a woman who desires to have a planned delivery.

Furthermore, it is important for a woman to know correctly and beforehand about future menstruation start dates in order to get prepared in advance and to plan ahead on the courses of action that follow.

However, women's physiological conditions are delicate and even those women who have fairly stable regular menstrual periods tend to develop irregular periods caused easily by a stress and the like, thereby causing the number of days in a menstrual period to be increased or decreased. Particularly, the women in modern times are increasingly thrown into a situation where they suffer from stresses and are likely to develop irregular menstrual periods frequently.

In order to cope with such irregular periods, the conventional thermometer for women designed for just taking an averaged out measurement value does not serve the purpose of predicting accurately the start date of next menstruation since even a woman having a rather stable number of days in a menstrual period may end up developing an irregular average number of days due to the existence of a few of the irregular periods, resulting in degradation of accuracy in the prediction on the start date of next menstruation.

Furthermore, there once existed a thermometer for women to predict and notify a start date of the next menstruation obtained by adding an average number of days in a menstrual period to the most recent menstruation start date, the number of days in each respective menstrual period being derived from the time interval between the menstruation start dates entered into a menstruation start date entering means. There also existed a thermometer for women to predict and notify a start date of the next menstruation obtained by adding 12 days (the 14th day counted from the first day of a high temperature range) to the date at the time when shifting from a low temperature range to a high temperature range is confirmed to have taken place, (the foregoing time corresponding to the time when the basal body temperature determined as being in the high temperature range continues for three days). (Refer to the Japanese Patent Unexamined Publication No. S 62-183807.)

However, when irregular periods are developed, it is said that only the number of days in the low temperature range varies and the number of days in the high temperature range remains almost constant and, therefore, with the thermometer for women whereby prediction and notification are given about the start date of next menstruation derived by adding 12 days to the date when shifting from the foregoing low temperature range to high temperature range was confirmed to have taken place, the influence of irregular periods developed is not so great as the influence to the thermometer for women whereby prediction and notification are given about the start date of next menstruation derived by simply adding the average number of days in a menstrual period to the most recent start date of menstruation, and yet it is impossible to cope with individual differences since the number of days in the high temperature range is fixed to 14 days. The number of days in the high temperature range extending over 14 days is considered as the norm but in actuality it ranges generally from 12 days to 16 days with 14 days serving as the median number of days. With the youth and women in menopause, their physiological functions are not stable, resulting in the number days in the high temperature range somewhat more or less than the norm. Due to an inability to cope with such individual differences, the accuracy in predictions tends to be degraded after all.

SUMMARY OF THE INVENTION

The present invention deals with the problems presented by conventional thermometers for women and aims at realizing an ear type thermometer for women whereby the accuracy in predicting a future start date of menstruation is enhanced.

In order to solve the foregoing problems, an ear type thermometer for women has a functional structure comprising the elements of enabling the extent of a tolerance of calculated eardrum temperature to be instructed; having the time spent on infrared measurement changed according to the tolerance instructed; performing infrared measurement according to a method whereby the extent of tolerance contained in an infrared measurement value is changed in accordance to the time spent on the infrared measurement; and deriving by calculation an eardrum temperature from the infrared measurement value.

According to this invention, the time spent on the infrared measurement is changed on the basis of an instructed tolerance, thereby allowing the eardrum temperature.measurement to be carried out within an appropriate time corresponding to the tolerance.

Also, the present invention solves the foregoing problems and makes it possible for the highest value in body temperatures to be found without relying on a large table of data and hardware for a high speed computation process. In a computation processing step after each respective infrared measurement process, a method of deriving by calculation a body temperature itself is replaced by a method of deriving by calculation a functional value which requires a smaller amount of computation than deriving body temperatures by calculation and also has a relationship of a simple function with body temperatures, thereby deriving by calculation the highest value in body temperature by using an infrared measurement value selected on the basis of the magnitude of the foregoing functional value. According to the present invention, a high and low relation of respective body temperatures derived by calculation from each respective infrared measurement value is analyzed according to a large and small relation of a cluster of functional values derived by calculation with a smaller computation amount spent than deriving body temperatures by calculation instead of deriving by calculation each respective body temperature. Thus, an infrared measurement value, which makes the result of deriving the body temperatures by calculation as the largest value, is selected and the process of deriving by calculation is just to be applied to a body temperature corresponding to the foregoing infrared measurement value, thereby leading to a reduction in the amount of computation itself of the computation process after each respective infrared measurement step and allowing the time required of the computation process to be made shorter.

In addition, in order to realize an ear type thermometer for women whereby an accurate measurement can be carried out, the present invention provides the probe attached to the ear type thermometer for women with an additional auxiliary probe that is designed to fit a specific user exclusively.

Further, the present invention discloses an ear type thermometer for women, comprising:

an infrared ray measuring means to measure a body temperature in an ear hole;

a plurality of interchangeable probes to be inserted in the ear hole for guiding infrared rays radiated from a human body to the infrared ray measuring means;

a probe adaptability determining means, which comprises: and a notifying means, wherein the probe adaptability determining means comprises:

a body temperature comparing means to make a comparison between the maximum value or the mean value of body temperatures in the ear hole measured the predetermined number of measurement times with a probe selected out of a plurality of the foregoing probes and the maximum values or the mean values of body temperatures in the ear hole derived in the same manner as above with other respective probes; and a body temperature variation determining means to determine the extent in variation of body temperatures in the ear hole measured a predetermined number of measurement times with a plurality of the foregoing probes, and, wherein the adaptability of each respective probe is determined from the outcome of at least the body temperature determining means and body temperature variation determining means and so notified, thereby making the ear type thermometer for women allow the user to select easily a probe whereby a correct measurement of an eardrum temperature can be carried out in accordance to the user's individual differences in external auditory miatus.

Also, the present invention proposes an ear type thermometer for women that has the configuration of a probe devised to realize a reduction in its contact area with the external auditory miatus, thereby allowing an accurate body temperature to be measured.

Additionally, an ear type thermometer for women of the present invention comprises:

a room temperature measuring means to perform a room temperature measurement;

an infrared ray measuring means for performing a body temperature measurement in the ear hole;

a continuous measurement times determining means to find out the continuous measurement times in one round of measurement in accordance with the room temperature measured by the room temperature measuring means; and a notifying means to send information on the number of continuous measurement times determined by the continuous measurement times determining means, thereby performing the measurements until stabilized repeatability corresponding to the room temperature is insured so as to realize the ear type thermometer for women whereby an adverse effect on the measured values at low temperatures is reduced as much as possible and also a change in the direction of the probe is handled properly when the probe is not aligned in the direction of an eardrum.

The present invention also proposes an ear type thermometer for women provided with a function of allowing the user to be assisted in making a planned delivery by noting via a controlling.means an ovulation date that is closest to the date derived by subtracting the normal number of days of pregnancy from the desired delivery date entered into a desired delivery date entering means.

In addition, an ear type thermometer for women according to the present invention comprises:

- an ear type body temperature measurement unit to measure a basal body temperature;
- a menstruation start date entering means to enter the first day of each respective menstrual period;
- a storing means to store the basal body temperatures measured in the body temperature measurement unit, the menstruation start dates entered by the menstruation start date entering means and the like; and
- a menstruation start date predicting means with a calendar function to predict a future menstruation start date on the basis of the data stored in the storing means, the menstruation start date predicting means being structured in such a way that:
  - a time period between the menstruation start dates stored in the storing means is taken as the number of days in a menstrual period corresponding to each respective menstrual period;
  - an average number of days in a valid menstrual period is derived by calculation for the valid menstrual period derived by eliminating menstrual periods, the number of days in each of which has a difference from the average number of days in a menstrual period exceeding a predetermined number of days, and also by eliminating menstrual periods, in which the difference between an average body temperature in the high temperature range and an average body temperature in the low temperature rang within each respective menstrual period does not exceed a predetermined value; and
  - the start date of menstruation at the nth period in future is predicted as (the most recent start date of menstruation+n×the average number of days in a valid menstrual period), thereby eliminating irregular menstrual periods to enhance the accuracy of prediction future menstruation start dates.

An ear type thermometer for women in a first mode of the present invention is an ear type thermometer for women whereby an eardrum temperature is derived by calculation based on the measurement value of infrared rays radiated from an object to be measured in temperature, i.e., an eardrum and the amount of time spent on the infrared measurement is changed according to the extent of tolerance of the eardrum temperature to be obtained. More specifically, the temperature measurement system is configured so as to carry out an infrared measurement by a method of changing the magnitude of errors contained in measurement values in accordance with the time spent on the measurement.

In other words, it becomes possible for the measurement of an eardrum temperature to be performed in an appropriate time period corresponding to a tolerance.

An ear type thermometer for women in a second mode of the present invention comprises the elements of:

- an infrared ray measuring means to measure infrared rays radiated from an object to be measured in temperature, i.e., an eardrum by a method of changing the extent of tolerance in a measured value according to the time period spent on the measurement;
- a tolerance instruction means to give an instruction on a tolerance for a temperature measurement result;
- a measurement time determining means to determine an infrared measurement time for the infrared ray measuring means based on a tolerance given as an instruction by the tolerance instructing means; and
- a body temperature calculating means to derive by calculation the temperature of an object to be measured in temperature, i.e., an eardrum by utilizing the result of infrared measurement performed in the infrared ray measuring means.

Therefore, it becomes possible for the temperature of an eardrum to be measured in an appropriate time period corresponding to a tolerance since the measurement time period of the infrared ray measuring means is determined by the measurement time determining means based on the tolerance instructed by the tolerance instructing means.

The result of temperature measurement includes the following two kinds of errors. One is a mechanical error that shows up with a certain steady tendency like being calculated always larger by a certain value and can be corrected by calibration and the other is a probability error, which varies in an irregular manner and the adverse effect of which can only be minimized by statistical processing. An ear type thermometer for women in a third mode of the present invention is structured to have a tolerance instructing means configured so as to give directions according to the aforementioned probability error.

By having probability errors only instructed by the tolerance instructing means, a measurement time determining means is allowed to eliminate the influence of mechanical errors and to determine a measurement time accurately.

An ear type thermometer in a fourth mode of the present invention is structured to have a measurement time determining means configured to determine a measurement time so as to have a simple decreasing relation against the tolerances instructed by a tolerance instructing means Since the infrared measurement time determined by a measurement time determining means is: short when a tolerance is large and long when the tolerance is small, it becomes possible to measure temperatures by freely selecting between the priorities placed on a shorter measurement time and a more accurate measurement.

An ear type thermometer for women in a fifth mode of the present invention is structured to have an infrared ray measuring means provided with a plurality of filter circuits having, respectively, a time constant different from one another, thereby smoothing the infrared measurement values.

More specifically, the infrared measurement values are allowed to be smoothed over a time period corresponding to the time constant of each respective filter circuit and a filter circuit with a time constant varying according to a tolerance is selected for use, thereby enabling an appropriate temperature measurement to be carried out.

An ear type thermometer for women in a sixth mode of the present invention is structured to have a measurement time determining means to determine a measurement time so as to be inversely proportional to a value expressed by a quadratic equation of tolerance.

In other words, the infrared measurement time determined by the measurement time determining means vary inversely with the square of the tolerance and since the measurement time becomes shorter when the tolerance is large and conversely becomes longer when the tolerance is small, it becomes possible to measure temperatures by freely selecting between the priorities placed on a shorter measurement time and a more accurate measurement.

An ear type thermometer for women in a seventh mode of the present invention is structured to have a measurement time determining means to determine the infrared measurement time so as to be inversely proportional to the square of a tolerance.

When principal errors contained in the infrared measurement value obtained by one round of measurement are probability errors varying according to such a Gaussian distribution as applicable to thermal noises and the like, the SN ratio of a measurement value can be enhanced in proportionate to the square root of the number of measurement times, where the final measurement value is obtained as an average value of a plurality of measurements performed on infrared rays. Also, by devising the infrared measurement time of the measurement time determining means as varying inversely with the square of a tolerance, it is made possible for the magnitude of an error contained in the infrared measurement value to be proportionate to a specified tolerance.

With an ear type thermometer for women in an eighth mode of the present invention, an infrared measurement time determined by a measurement time determining means is determined so as to be inversely proportional to the square of a value derived by subtracting a predetermined value from a tolerance.

Further, when an error contained in an infrared measurement value obtained by one round of measurement includes a probability error varying according to such a Gaussian distribution as applicable to thermal noises and the like and a predetermined amount of mechanical errors the SN ratio of a measurement value can be enhanced in proportionate to the square root of a value derived by subtracting a predetermined numerical value corresponding to mechanical noises from the number of measurement times, where the final measurement value is obtained as an average value of a plurality of measurements performed on infrared rays, thereby making it possible for the magnitude of an error contained in the infrared measurement value to be proportionate to a specified tolerance.

With an ear type thermometer for women in a ninth mode of the present invention, a tolerance instructing means has a tolerance entering means whereby a tolerance is entered in a numerical value Further, a measurement time determining means determines an infrared measurement time based on the numerical number entered from the tolerance entering means, thereby allowing the temperature of an eardrum to be measured in an appropriate time period corresponding to the tolerance entered.

With an ear type thermometer for women in a tenth mode of the present invention, a tolerance instructing means has a tolerance selecting means whereby one of a plurality of predetermined tolerances is selected.

Further, a measurement time determining means determines an infrared measurement time based on the tolerance selected by the tolerance selecting means, thereby allowing the temperature of an eardrum to be measured in an appropriate time period corresponding to the tolerance.

An ear type thermometer for women in an eleventh mode of the present invention is structured to have an infrared ray measuring means so as to start an infrared measurement when a tolerance is selected by a tolerance selecting means.

Upon selecting the tolerance through operation of the tolerance selecting means, the infrared measurement and a subsequent calculation of temperatures are carried out automatically, thereby allowing the temperature measurement to be performed promptly without taking the trouble of giving a separate instruction to start a temperature measurement.

An ear type thermometer for women in a twelfth mode of the present invention is structured to have a measurement instructing means to instruct a temperature measurement start so as to have the infrared measurement started when an infrared ray measuring means receives an instruction from the measurement instructing means.

Further, since the infrared measurement and the subsequent start of deriving temperatures by calculation are carried out according to an instruction from the measurement instructing means, after having set a tolerance by utilizing a tolerance instructing means in advance, the operation of the measurement instructing means is repeated a few times, thereby allowing the temperatures of a plurality of eardrums to be measured with the same tolerance in succession without resetting the tolerance many times.

An ear type thermometer for women in a thirteenth mode of the present invention has a human body as the object to be measured in temperature and has a tolerance selecting means provided with a thermometer function selecting means whereby a selection is made between the use of the ear type thermometer for women as a thermometer for women and the use as a general purpose thermometer requiring a less stringent tolerance than the thermometer for women.

Further, a tolerance is selected by the tolerance selecting means based on the application of the ear type thermometer for women as a thermometer for women or a general purpose thermometer selected by the thermometer function selecting means, thereby allowing the body temperature measurement to be carried out with a measurement error and measurement time period corresponding to the purpose of application.

An ear type thermometer for women in a fourteenth mode of the present invention is structured to have a tolerance instructing means located so as to allow the user to perform the operation thereof whenever necessary.

Further, since a tolerance can be set at any time by operating the tolerance instructing means, a tolerance as required and a measurement time determined accordingly are allowed to be determined at the user's own will.

An ear type thermometer for women in a fifteenth, mode of the present invention is structured to have a tolerance instructing means arranged to be operated at the maker side before shipment so that the user cannot operate the tolerance instructing means thereafter.

By operating the tolerance instructing means before shipment on the part of the company who produces the ear type thermometer for women, it becomes possible for a plurality of kinds of ear type thermometers for women having an error contained in a temperature measurement result and a time period required by temperature measurement, both of which differ from one thermometer to another, to be produced on the same production line of the same factory.

With an ear type thermometer for women in a sixteenth mode of the present invention, a measurement value of infrared rays radiated from an eardrum is treated as a variable and a functional value, which can be derived by calculation at a smaller amount of calculation than that of a body temperature and also belongs to a function in a simple functional relation with the body temperature, is derived by calculation. In other words, a functional value is derived by calculation against each respective measurement value obtained by carrying out a plurality of measurements performed on infrared rays and then a body temperature is derived by calculation with the use of an infrared measurement value selected based on the magnitude of each respective functional value.

According to the present mode, instead of deriving by calculation individual body temperatures themselves, a high and low relation of individual body temperatures derived by calculation from respective infrared measurement values is checked based on a large and small relation of a group of functional values derived with a smaller amount of calculation of body temperatures, and an infrared measurement value yielding the largest value as a result of deriving body temperatures by calculation is selected for deriving a particular body temperature by calculation against the infrared measurement value, thereby allowing the computation processing time after individual infrared measurement processes to be made shorter when compared with the case where body temperatures are derived by calculation each time.

An ear type thermometer for women in a seventeenth mode of the present invention comprises:

an infrared ray measuring means to measure infrared rays radiated from an eardrum;

a functional value calculating means to derive by calculation a functional value, which can be derived at a smaller amount of computation than deriving a body temperature with an infrared measurement value treated as a variable and also belongs to a function in a simple, functional relation with a body temperature, in accordance with each respective measurement value obtained by the infrared ray measuring means in carrying out a plurality of times of infrared measurement;

a functional value selecting means to select one functional value out of a group of functional values derived by calculation by the functional value calculating means based on a magnitude of each respective functional value; and a body temperature calculating means to derive by calculation a body temperature by using an infrared measurement value corresponding to the functional value selected by the functional value selecting means.

More specifically, the infrared ray measuring means measures infrared rays radiated from an eardrum and the functional value calculating means derives by calculation a functional value with the infrared measurement value treated as a variable. At this time, the amount of calculation is smaller than deriving a body temperature by calculation. This function is in a simple functional relation with body temperatures. When the functional value calculating means derives a functional value by calculation, the infrared ray measuring means derives by calculation each respective measurement value obtained by performing a plurality of times in infrared measurement according to the functional value, the functional value selecting means selects an infrared measurement value yielding the largest value as the calculation result of body temperatures by checking a large and small relation of the functional values derived by calculation by the functional value calculating means and finally the body temperature calculating means derives body temperatures by calculation against only the infrared measurement values selected by the functional value selecting means. Thereby allowing the time required of the calculation process after the individual infrared measurement processes to be shorter than deriving by calculation body temperatures each time and checking a high and low relation for requiring the highest value.

In addition to what is described about the ear type thermometer in the seventeenth mode of the present invention, an ear type thermometer for women in an eighteenth mode of the present invention comprises the functions of:

deriving by calculation from the functional value calculating means a functional value of a function in a simple increasing relation with a body temperature; and selecting the largest functional value out of a group of functional values derived by calculation from the functional value calculating means via the functional value selecting means.

Further, since the largest functional value is selected from a group of the functional values derived by calculation from the functional value calculating means and body temperatures against the selected infrared measurement values only are derived by calculation by the body temperature calculating means, the time required by calculation processes after each respective infrared measurement process can be made shorter than the case where body temperatures are derived by calculation each time.

In addition to what is described about the ear type thermometer in the seventeenth mode of the present invention, an ear type thermometer for women in a nineteenth mode of the present invention comprises the functions of:

deriving by calculation from the functional value calculating means a functional value of a function in a simple decreasing relation with a body temperature; and selecting the smallest functional value via the functional value selecting means out of a group of functional values derived by calculation from the functional value calculating means.

In the same manner as with the eighteenth mode, since body temperatures against the selected infrared measurement values only are derived by calculation by the body temperature calculating means, the time required by calculation processes after each respective infrared measurement process can be made shorter than the case where body temperatures are derived by calculation each time.

In addition to what is described about the ear type thermometer in the seventeenth mode of the present invention, an ear type thermometer for women in an twentieth mode of the present invention comprises a function of deriving by calculation body temperatures via the body temperature calculating means from functional values selected by the functional value selecting means.

Since body temperatures are directly derived by calculation via the body temperature calculating means from the functional values themselves selected by the functional value selecting means, body temperatures can be derived by calculation easily without taking the trouble of storing the infrared measurement values used in deriving by calculation the functional values via the functional value calculating means.

In addition to the invention in any one of the seventeenth and twentieth modes of the present invention, an ear type thermometer for women in a twenty first mode of the present invention is structured to make a measurement value from the infrared ray measuring means, as is, as a functional value by the functional value calculating means.

A Since the measurement value obtained from the infrared ray measuring means, as is, is made the functional value via the functional value calculating means, the time required in computations after each respective infrared measuring process can be shortened by the time required of the functional value calculating means to derive the functional values by calculation.

In addition to the invention in the seventeenth mode of the present invention, an ear type thermometer for women in a twenty second mode of the present invention is provided with a sensor temperature measuring means to measure an operating ambient temperature and structured to have a smaller number of measurement times performed on the operating ambient temperature than the number of the infrared measurement times performed by the infrared ray measuring means and also to derive by calculation via the body temperature calculating means a body temperature corrected.by using a temperature measured by the sensor temperature measuring means.

Since the number of temperature measurement times of the sensor temperature measuring means is smaller than the number of infrared measurement times, the time required of calculation processes after each respective infrared process can be made shorter than ever when compared with the case where a body temperature is derived by calculation with a correction applied thereto according to an ambient temperature measured by the sensor temperature measuring means every time an infrared measurement is carried out by the infrared ray measuring means.

In addition to the invention in the twenty second mode of the present invention, an ear type thermometer for women in a twenty third mode of the present invention is structured to include a process of measuring via the sensor temperature measuring means an operating ambient temperature only once every time a body temperature is derived by calculation from the body temperature calculating means.

Since the sensor temperature measuring means measures a temperature only once, a body temperature measurement can be finished in a shorter time period than the sensor temperature measuring means carries out a plurality of times in temperature measurement.

In addition to the seventeenth mode of the present invention or the eighteenth mode of the present invention, an ear type thermometer for women in a twenty fourth mode of the present invention is structured to include a process of deriving by calculation a value corresponding to the fourth power of a body temperature via the functional value calculating means.

Since the biquadratic root calculation required to be performed as the final step of deriving by calculation a body temperature from an infrared measurement value can be omitted at the time of deriving by calculation a functional value via the functional value calculating means, the time required of computations after each respective infrared measuring process is allowed to be made shorter.

In addition to the seventeenth mode of the present invention or the eighteenth mode of the present invention, an ear type thermometer for women in a twenty fifth mode of the present invention is structured to include a process of deriving by calculation a value corresponding to the square of a body temperature via the functional value calculating means.

Further, since the biquadratic root calculation that has to be performed at the last step of deriving by calculation a body temperature from an infrared measurement value is to be replaced by a square root calculation when deriving a functional value by calculation via the functional value calculating means, the time required of calculation processes performed for each respective infrared measurement value by the functional value calculating means can be shortened by the time required for one time of the square root calculation when two times of the square root calculation are needed to, perform the biquadratic root calculation.

An ear type thermometer for women in a twenty sixth mode of the present invention has a method of temperature measurement comprising the steps of:

converting infrared rays radiated from an eardrum to an electrical signal; obtaining an infrared measurement value by applying a first calculating method and also a second calculating method that requires a longer calculation time than the first calculating method and achieves a higher degree of accuracy than the first calculating method;

deriving by calculation a functional value, which can be derived by calculation with a smaller amount of calculation than deriving a body temperature by calculation and also belongs to a function in a simple functional relation with body temperatures, for each respective measurement value obtained by carrying out a plurality of times in infrared measurement according to the first calculation method by using the respective measurement values as variables; selecting one functional value out of the functional values derived by calculation based on the magnitude thereof; and deriving by calculation a body temperature using an infrared measurement value obtained by applying the second calculating method to the foregoing electrical signal corresponding to the selected functional value. In other words, a large and small relation of each respective body temperature derived by calculation from the infrared measurement values is checked based on a large and small relation of a group of functional values derived by calculation by the first calculating method with a smaller amount of calculation than deriving by calculation a body temperature from each respective infrared measurement value, and an infrared measurement value that makes the calculating result of body temperatures as the largest value is selected and determined from the electrical signal of the infrared sensor corresponding thereto according to the second calculating method, thereby deriving by calculation a body temperature against the particular infrared measurement value only. At the time of deriving by calculation each respective functional value, the infrared measurement values obtainable with a short calculating time according to the first calculating method are used and at the time of deriving by calculation body temperatures, the infrared measurement values obtainable with a high degree of accuracy according to the second calculating method are used, thereby allowing a body temperature to be derived by calculation with a high degree of accuracy while the time required of computations after each respective infrared measurement process being kept short.

An ear type thermometer for women in a twenty seventh mode of the present invention comprises the elements of:

an infrared sensor to convert infrared rays radiated from an eardrum into an electrical signal;

a first infrared measurement value calculating means to take in the electrical signal from the infrared sensor and derive by calculation a measurement value of the infrared rays radiated from the eardrum;

a second infrared measurement value calculating means to derive by calculation a measurement value of the infrared rays by taking in the electrical signal from the infrared sensor and spending a longer calculating time than the first infrared measurement value calculating means with a higher degree of calculating accuracy than the first infrared measurement value calculating means;

a functional value calculating means to derive by calculation a functional value for each respective measurement value derived by calculation from the first infrared measurement value calculating means by carrying out a plurality of times in infrared measurement with the measurement values treated as variables, the functional value being allowed to be derived by calculation with a smaller amount of computation than deriving body temperatures by calculation and also of a function in a simple functional relation with body temperatures, and at the same time to derive by calculation a measurement value derived from the foregoing second infrared measurement value calculating means against the electrical signal of the infrared sensor used in deriving by calculation the foregoing measurement value in accordance to the functional value derived by calculation;

a functional value selecting means to select one functional value out of a group of functional values derived by calculation from the functional value calculating means based on the magnitude of each respective functional value; and a body temperature calculating means to derive by calculation body temperatures according to measurement values derived from the second infrared measurement value calculating means corresponding to the functional values selected by the functional value selecting means, thereby allowing the body temperatures to be derived at a high degree of accuracy by calculation while keeping the time required of the functional value calculating means to carry out computations for each respective infrared measurement value short.

In addition to what is described about the ear type thermometer in the twenty seventh mode of the present invention, an ear type thermometer for women in a twenty eighth mode of the present invention comprises the functions of:

deriving by calculation from the functional value calculating means a functional value of a function in a simple increasing relation with a body temperature; and selecting the largest functional value out of a group of functional values derived by calculation from the functional value calculating means via the functional value selecting means.

Further, the functional value calculating means derives by calculation a functional value, which can be derived by calculation with a smaller amount of computation than deriving a body temperature by calculation and also belongs to a function in a simple increasing relation with a body temperature, while treating an infrared measurement value as a variable, and the functional value selecting means selects the largest functional value out of a group of functional values derived by calculation via the functional value calculating means rather than selecting the highest value from each respective body temperature itself, thereby deriving by calculation a body temperature only against an output value of the second infrared measurement value calculating means corresponding to the selected infrared measurement value. As a result, the time required of the functional value calculating means to carry out computations for each respective infrared measurement value can be made short and also body temperatures can be derived by calculation with a higher degree of accuracy.

In addition to what is described about the ear type thermometer in the twenty seventh mode of the present invention, an ear type thermometer for women in a twenty ninth mode of the present invention comprises the functions of:

deriving by calculation from the functional value calculating means a functional value of a function in a simple decreasing relation with a body temperature; and selecting the smallest functional value out of a group of functional values derived by calculation from the functional value calculating means via the functional value selecting means.

Further, the functional value calculating means derives by calculation a functional value, which can be derived by calculation with a smaller amount of calculation than deriving a body temperature by calculation and also belongs to a function in a simple decreasing relation with a body temperature, while treating an infrared measurement value as a variable, the functional value selecting means selects the smallest functional value out of a group of functional values and the body temperature calculating means derives by calculation a body temperature only against the output value of the second infrared measurement value calculating means corresponding to the selected infrared measurement value, thereby allowing body temperatures to be derived by calculation with a high degree of accuracy while the time required of the functional value calculating means to carry out computations for each respective infrared measurement value being made short.

In addition to whatever described in the twenty seventh or twenty ninth mode of the present invention, an ear type thermometer for women in a thirtieth mode of the present invention is structured to have a signal value storing means to store an electrical signal value obtained by the infrared sensor, wherein the second infrared measurement value calculating means derives by calculation an infrared measurement value corresponding to a functional value selected by the functional value selecting means by using the electrical signal value stored in the signal value storing means after the functional value is selected.

Further, since the second infrared measurement value is derived by calculation by using a signal value stored in the signal value storing means as a measurement value corresponding to a functional value after the functional value is selected by the functional value selecting means, the second infrared measurement value calculating means requiring a long calculating time needs to obtain only one measurement value corresponding to the functional value selected by the functional value selecting means, thereby allowing the total amount of time required of computations to obtain the second infrared measurement value to be made short.

In addition to whatever described in the twenty seventh or thirtieth mode of the present invention, an ear type thermometer for women in a thirty first mode of the present invention is structured to have the number of taking in times of the output signal of the infrared sensor necessary for the first infrared measurement calculating means to derive by calculation an infrared measurement value made smaller than the number of taking in the output signal of the infrared sensor necessary for the second infrared measurement calculating means to derive by calculation an infrared measurement value.

Since the number of taking in times of the electrical signal of the infrared sensor required of the first infrared measurement value calculating means to derive by calculation an infrared measurement value is smaller than the number of taking in times of the electrical signal of the infrared sensor required of the second infrared measurement value calculating means to derive by calculation an infrared measurement value, the calculation time of the first infrared measurement value calculating means is allowed to be made easily shorter than the calculation time of the second infrared measurement value calculating means.

In addition to whatever described in the twenty seventh or thirty first mode of the present invention, an ear type thermometer for women in a thirty second mode of the present invention is structured to use a measurement value of the first infrared measurement value calculating means, as is, as a functional value in the functional value calculating means.

In other words, since the functional value calculating means employs the measurement value obtained by the infrared ray measuring means, as is, as a functional value, the time required of computations after each respective infrared measurement process can be made further short by the time period required of the functional value calculating means to derive the functional value by calculation.

In addition to whatever described in the twenty: seventh or thirty second mode of the present invention, an ear type thermometer for women in a thirty third mode of the present invention is structured to have a sensor temperature measuring means to measure the operating ambient temperature of an ear type thermometer for women, thereby allowing the body temperature calculating means to derive by calculation a corrected body temperature with the use of a temperature measured by the sensor temperature measuring means.

Since the number of temperature measurement times performed by the sensor temperature measuring means is smaller than the number of infrared measurement times performed by the infrared ray measuring means, the time required of computations after each respective infrared measurement process is allowed to be made further short when compared with the case where a body temperature is corrected by the ambient temperature from the sensor temperature calculating means each time when the infrared measurement is carried out by the infrared ray measuring means.

In addition to what is described in the thirty third mode of the present invention, an ear type thermometer for women in a thirty fourth mode of the present invention is structured to carry out an operating ambient temperature measurement by the sensor temperature measuring means only once for one time of deriving a body temperature by calculation by the body temperature calculation means.

In other words, since the ambient temperature is measured only once by the sensor temperature measuring means, a body temperature measurement is allowed to be finished in a shorter time period in comparison with the case where a plurality of temperature measurement times are carried out by the sensor temperature measuring means.

An ear type thermometer for women in a thirty fifth mode of the present invention has an auxiliary probe to suit the user provided to a probe of the main body of ear type thermometer for women, thereby allowing the ear type thermometer for women to carry out an accurate temperature measurement.

An ear type thermometer for women in a thirty sixth mode of the present invention has a coupling means to fix the position of an auxiliary probe provided to a probe of the main body of ear type thermometer for women, thereby keeping the fixing position of the auxiliary probe invariant and allowing the ear type thermometer for women to carry out an accurate temperature measurement.

An ear type thermometer for women in a thirty seventh mode of the present invention has a plurality of grooves provided to a probe of an ear type thermometer for women and further has a coupling means to fix the position of an auxiliary probe, thereby keeping the position of the auxiliary probe fixed and allowing the ear type thermometer for women to carry out an accurate temperature measurement.

An ear type thermometer for women in a thirty eighth mode of the present invention has a probe provided with tick marks on the surface thereof so as to allow the depth of insertion of the probe in an ear hole to be checked from outside, thereby allowing the ear type thermometer for women to carry out an accurate temperature measurement.

An ear type thermometer for women in a thirty ninth mode of the present invention comprises the elements of:
 an infrared ray measuring means to measure a body temperature in an ear hole;
 a plurality of interchangeable probes, each being inserted in the ear hole and intended for guiding the infrared rays radiated from the human body to the infrared ray measuring means;
 a probe adaptability determining means; and
 a notifying means,
 wherein the probe adaptability means comprises the elements of:
  a body temperature comparing means to compare the maximum value or average value of body temperatures in the ear hole, which are obtained as a result of temperature measurement performed a predetermined number of times, the comparison being made between one probe of a plurality of the foregoing probes and another; and
  a body temperature variation determining means to determine an extent of the variation in body temperatures in the ear hole obtained as a result of temperature measurement performed a predetermined number of times on a plurality of the foregoing probes, thereby determining a degree of the adaptability of a probe from the output of at least the body temperature comparing means and body temperature variation determining means and notifying the determined degree of the adaptability to the user so as to allow the user to select easily a probe that enables the eardrum temperature measurement to be carried out accurately in accordance to individual differences in an external auditory miatus.

With an ear type thermometer for women in a fortieth mode of the present invention, the foregoing probe adaptability determining means has a probe identifying means to identify automatically a probe of a plurality of the foregoing probes when the probe is attached to the infrared ray measuring means, and notifies the degree of adaptability of the probe identified automatically by the probe identifying means to the user, thereby allowing the user to select the most suitable probe with added easiness.

An ear type thermometer for women in a forty first mode of the present invention further comprises the elements of:
 a room temperature measuring means to measure a room temperature; and
 a room temperature storing means,
 wherein the room temperature measuring means notifies the user that the probe's adaptability is urged to be determined again by using the probe adaptability determining means when the room temperature turns out to be below a predetermined value for the first time after storing the temperature at the time of measurement performed by the infrared ray measuring means, thereby allowing the user to select the most suitable probe enabling a more accurate eardrum temperature measurement to be carried out even when the room temperature is low.

An ear type thermometer for women in a forty second mode of the present invention further has a clocking means, wherein the clocking means measures the lapse of time after determining the probe's adaptability at the probe adaptability determining means and notifying the lapse of time to the user and, when the foregoing lapse of time passes a predetermined time, a notification is made to the effect that the probe's adaptability is urged to be determined again by the use of the probe adaptability determining means, thereby allowing the user to select easily the most suitable probe to enable an eardrum temperature measurement to be carried out more accurately, also according to secular changes in the external auditory miatus.

An ear type thermometer for women in a forty third mode of the present invention further comprises the elements of:

an individuals switching means; and an adaptability storing means, wherein the probe adaptability determining means notifies the latest probe's adaptability determined for each respective individual by using the individuals switching means and so notified, thereby allowing the user to find out quickly her own probe's adaptability once the individuals switching means is adjusted to her own position, thereby allowing the user to select easily the most suitable probe to enable the eardrum temperature measurement to be carried out more accurately even by coping with the case where a particular thermometer is used by the members of a family jointly.

An ear type thermometer for women in a forty fourth mode of the present invention further comprises a menstruation start date entering means, wherein, at the time when a menstruation start date is entered, a notification is given to the effect that the probe's adaptability is urged to be determined again by the use of the probe adaptability determining means, thereby allowing the user to select easily the most suitable probe to enable a basal female body temperature measurement to be carried out correctly and with stability for each respective menstrual period.

An ear type thermometer for women in a forty fifth mode of the present invention, employs a probe having many holes to reduce the amount of heat dissipation 0from an ear hole when the probe is inserted in the ear hole, thereby allowing a body temperature to be measured accurately even in an environment of a low room temperature.

An ear type thermometer for women in a forty sixth mode of the present invention employs a probe with grooves to reduce the amount of heat dissipation from an ear hole when the probe is inserted in the ear hole, thereby allowing a body temperature to be measured accurately even in an environment of a low room temperature. An ear type thermometer for women in a forty seventh mode of the present invention employs a probe formed of only an outer framework for inserting the main body of the probe into an ear hole to reduce the amount of heat dissipation from the ear hole when the probe is inserted in the ear, thereby allowing a body temperature to be measured accurately even in an environment of a low room temperature.

An ear type thermometer for women in a forty eighth mode of the present invention employs a probe covered with a raising material, thereby preventing an ear hole from dissipating heat when the probe is inserted in the ear and allowing a body temperature to be measured accurately even in an environment of a low room temperature.

An ear type thermometer for women in a forty ninth mode of the present invention comprises the elements of:

a room temperature measuring means to measure a room temperature;

an infrared ray measuring means to measure body temperatures in an ear hole;

a continuous measurement times determining means to determine the number of continuous measurement times per a measurement in accordance with a room temperature measured, by the room temperature measuring means; and a notifying means, wherein the continuous measurement times determining means is to notify the number of continuous measurement times determined so as to prevent an adverse effect imposed on the measurement value under a low temperature as much as possible and also to cope with a change in direction when a probe is not aligned in the direction of an eardrum.

An ear type thermometer for women in a fiftieth mode of the present invention further comprises the elements of:

a storing means; and a notifying means, wherein the maximum value of the body temperatures in an ear hole measured during a period covering the continuous measurement times determined by the continuous measurement times determining means is stored in the storing means and the continuous measurement times and the maximum value in body temperatures are informed via the notifying means, thereby allowing the user to know easily a highly reliable measurement value.

An ear type thermometer for women in a fifty first mode of the present invention further comprises a clocking means, wherein the continuous measurement times determining means determines again the number of continuous measurement times at a room temperature when the measurement time interval of body temperatures in an ear hole is stretched to exceed a predetermined time period and notifies the redetermined number of continuous measurement times, thereby allowing the change in room temperature, which occurs during the period when the measurement interval of body temperatures in the ear hole is stretched to exceed a predetermined time period, to be coped with.

An ear type thermometer for women in a fifty second mode of the present invention further comprises a measurement value variation determining means, wherein the continuous measurement times determining means increases the number of continuous measurement times when a range of measurement value variations of body temperatures in an ear hole is found to be a predetermined value or more, thereby enhancing the reliability of measurement values.

With an ear type thermometer for women in a fifty third mode of the present invention, a continuous measurement times determining means notifies the user about the balance of the number of continuous measurement times every time the user stops temperature measurement, thereby creating awareness on the part of the user to obtain a highly reliable measurement value.

With an ear type thermometer for women in a fifty fourth mode of the present invention, a continuous measurement times determining means provides a notification of alarm when the user is about to end a measurement with the number of continuous measurement times not having reached a predetermined value, thereby creating awareness on the part of the user to obtain a highly reliable measurement value.

With an ear type thermometer for women in a fifty fifth mode of the present invention, a controlling means has the functions of:

predicting a future menstruation start date and a future ovulation date from the body temperature data and data on menstruation start dates that are stored in a storing means; and notifying an ovulation date that is closest to the date derived by subtracting a normal period of pregnancy from the desired date of delivery entered in a desired delivery date entering means, thereby allowing a planned delivery to be facilitated.

With an ear type thermometer for women in a fifty sixth mode of the present invention, a controlling means has the function of notifying that, in the case where an ovulation date notified at the time when a desired delivery date is entered by a desired delivery date entering means, turns out to be different from the ovulation date predicted based on the data collected after the foregoing time, the ovulation date is different from prediction, thereby allowing the user to know a more accurate ovulation date corresponding to the desired delivery date and to facilitate a planned delivery.

With an ear type thermometer for women in a fifty seventh mode of the present invention, a controlling means has the function of notifying an applicable ovulation date or that the applicable ovulation date is included in a corresponding menstrual period in the case where the ovulation date notified falls in the period between the menstruation start date entered and the next menstruation start date at the time when the menstruation start date is entered by a menstruation start date entering means, thereby allowing the user to know on the first day of the menstrual period of the applicable ovulation date that she is already in the menstrual period of the applicable ovulation date and to exercise added care in keeping good physical conditions.

With an ear type thermometer for women in a fifty eighth mode of the present invention, a controlling means has the function of notifying an applicable ovulation date or that the applicable ovulation date is included in a corresponding menstrual period in the case where an ovulation date notified during the period between the latest menstruation start date and the next menstruation start date, thereby allowing the user to exercise added care in keeping good physical conditions during the menstrual period of the applicable ovulation date.

With an ear type thermometer for women in a fifty ninth mode of the present invention, a controlling means has the function of notifying that, when the date of a body temperature measurement carried out at a body temperature measurement unit falls within a predetermined number of days before and after the applicable ovulation date notified and also the body temperature of the temperature measurement date is the lowest in comparison with the body temperatures measured within the predetermined number of days before and after the applicable ovulation date already stored in a data storing means, there is a great possibility that the body temperature measurement date is the true applicable ovulation date, thereby allowing the user to know the applicable ovulation date more precisely.

With an ear type thermometer for women in a sixtieth mode of the present invention, a controlling means has the function of notifying an expected delivery date based on an assumption that the user is pregnant on the applicable ovulation date notified, thereby allowing the user to make fine adjustments of the desired delivery date by checking the difference between the expected delivery date and the desired delivery date.

With an ear type thermometer for women in a sixty first mode of the present invention, a controlling means has the function of notifying a miscarriage prone period, a secure period and a premature delivery prone period based on an assumption that the user is pregnant on the, applicable ovulation date notified, thereby allowing the user to plan on a delivery schedule that is the most suited to the activity timetable while in pregnancy by changing the desired delivery date in various ways and checking the expected delivery dates displayed in accordance with each respective desired delivery date.

An ear type thermometer for women in a sixty second mode of the present invention comprises the elements of:

an ear type body temperature measurement unit to measure basal body temperatures;

a menstruation start date entering means to enter the first day of each respective menstrual period;

a storing means to store the basal body temperatures measured at the body temperature measurement unit, the menstruation start dates entered at the menstruation start date entering means and the like; and a menstruation start date predicting means provided with a calendar function to predict a future menstruation start date based on the data stored in the storing means, wherein the menstruation start date predicting means is structured treating the time interval between the menstruation start dates stored in the storing means as the number of days in a menstrual period corresponding to each respective menstrual period, to derive by calculation an average number of days in valid menstrual periods eliminating both the menstrual periods, each of which has a predetermined number of days or more in the difference from the average number of days in a menstrual period, and each of which has the difference between the average body temperature in a high temperature range and the average body temperature in a low temperature range in each respective menstrual period, not exceeding a predetermined value, and to predict the menstruation start date at nth period in future as (the latest menstruation start date+n×the average number of days in valid menstrual periods), thus enhancing the accuracy in predicting the menstruation start date in future by eliminating irregular menstrual periods.

An ear type thermometer for women in a sixty third mode of the present invention is structured to have the foregoing menstruation start date predicting means so as to predict the menstruation start date in future when the number of valid menstruation periods accounts for a predetermined ratio or more of the number of all menstrual periods, thereby enhancing further the accuracy in predicting the menstruation start date in future.

An ear type thermometer for women in a sixty fourth mode of the present invention is structured to have the foregoing menstruation start date predicting means to make a modifying prediction by adopting a date as the next menstruation start date, the date being derived by adding the average number of days in a high temperature range calculated from the basal body temperature for each respective menstrual period as stored in the storing means to the date before the first day in a high temperature range at the time when the transition from the low temperature range to the high temperature range can be determined to have taken place, thus enhancing the accuracy in predicting the menstruation start date in future by eliminating the adverse effect due to variations in the low temperature range of the ongoing menstrual period and also coping with differences between individuals.

An ear type thermometer for women in a sixty fifth mode of the present invention comprises:

a body temperature difference calculating means to derive by calculation an average difference in body temperature between a menstruation start date and the day before the menstruation start date from the basal body temperature and menstruation start dates stored in the storing means, wherein the menstruation start date predicting means is structured so as to have a date predicted by correction as the next menstruation start date, the date being the day when the basal body temperature measured by the ear type body temperature measurement unit has a difference from the basal body temperature of the preceding day exceeding the difference in body temperature derived by calculation at the body temperature difference calculating means in a case where no menstruation dates are entered to the menstruation start date entering means even if the next menstruation date predicted is passed, i.e., a menstrual period has a large number of days in a menstrual period, thus allowing the accuracy in predicting the future menstruation start dates to be enhanced by coping with differences between individuals.

An ear type thermometer for women in a sixty sixth mode of the present invention comprises a notifying means, wherein the notifying means is structured to notify a future menstruation start date every time when a menstruation start date is entered in the menstruation start date entering means or a prediction is made by correction at the menstruation start date predicting means, thereby always allowing the user to recognize the future menstruation dates with a high degree of accuracy in prediction.

An ear type thermometer for women in a sixty seventh mode of the present invention comprises a storing means restricting means, wherein the storing means restricting means is structured so as to restrict the data used at the menstruation start date predicting means for predicting the future menstruation start dates to the data accumulated within a predetermined period from the present day, thus allowing the accuracy in predicting the future menstruation start dates to be enhanced by coping with the recent variations in menstrual period.

BRIEF DESCRIPTION OF DRAWINGS

FIG. 30 is a flow chart to show how the ear type thermometer for women in the twelfth exemplary embodiment of the present invention operates.

FIG. 53 is a flow chart to show an operational flow of the ear type thermometer for women in the thirty fifth exemplary embodiment of the present invention.

FIG. 54 is a flow chart to show an operational flow of an ear type thermometer for women in a thirty sixth exemplary embodiment of the present invention.

FIG. 55 is a flow chart to show an operational flow of an ear type thermometer for women in a thirty seventh exemplary embodiment of the present invention.

FIG. 57 is a flow chart to show an operational flow of the ear type thermometer for women in the thirty eighth exemplary embodiment of the present invention.

PREFERRED EMBODIMENTS OF THE INVENTION

Next, a detailed description is given to preferred embodiments of the present invention with reference to drawings.
(First Exemplary Embodiment)

Figure 1:
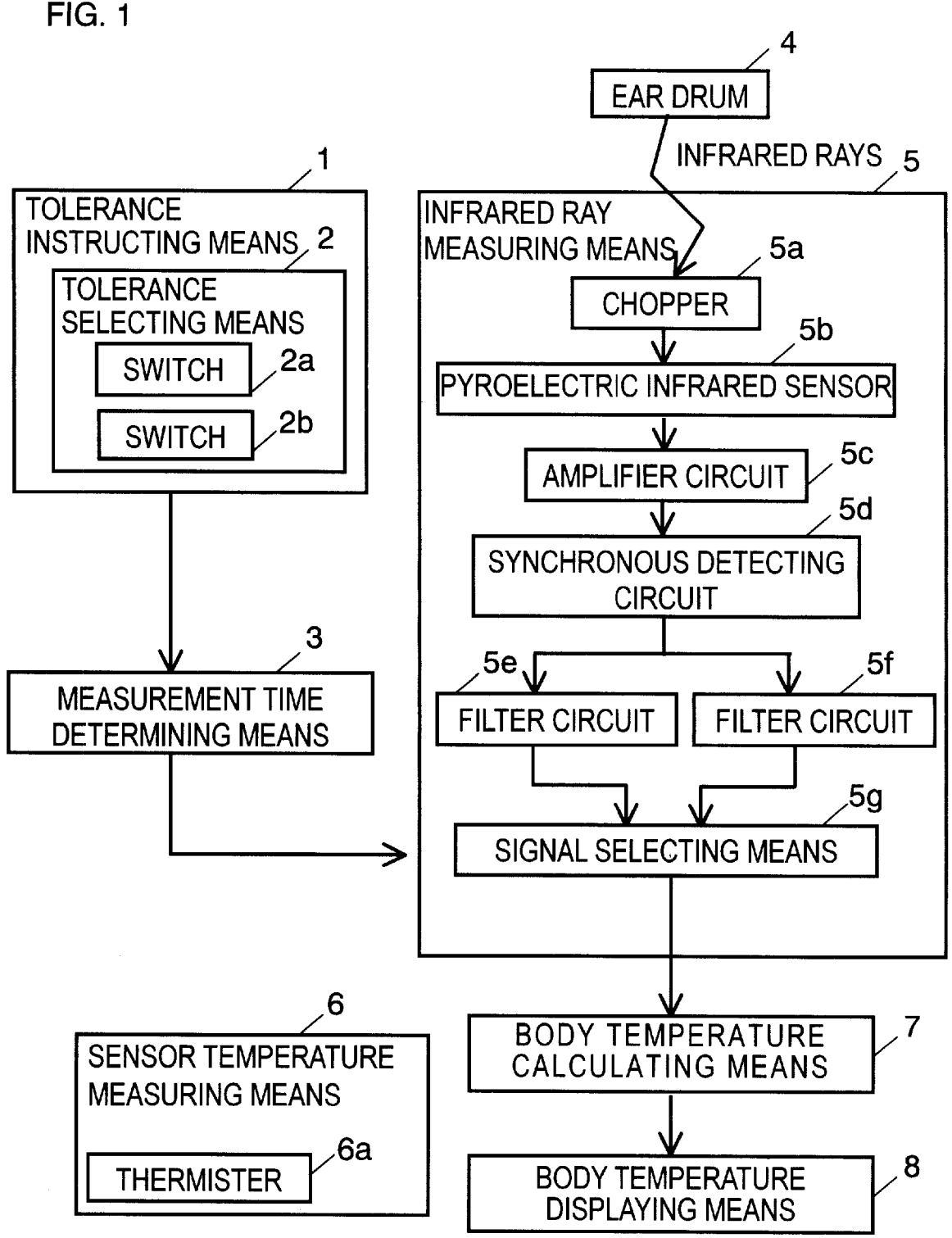
FIG. 1 is a block diagram of an ear type thermometer for women in a first exemplary embodiment of the present invention.

FIG. 1 is a block diagram of an ear type thermometer for women in a first exemplary embodiment of the present invention. In FIG. 1, although a filter circuit 5e and a filter circuit 5f are both formed of a low pass filter, the time constant of the low pass filter used in the filter circuit 5e is made smaller than the time constant of the low pass filter used in the filter circuit 5f. For ease of descriptions that follows, the time period required of the output signal of the filter circuit 5e to reach a stabilized value after a chopper 5a started to operate is expressed as $\tau 1$ and the time period required of the output signal of the filter circuit 5f to reach a stabilized value is expressed as $\tau 2$. At this time, an inequality of $\tau 1 < \tau 2$. is established since the time constant of the filter circuit 5e is smaller than that of the filter circuit 5f.

A sensor temperature measuring means 6 is formed of a thermister thermally coupled with the chopper 5a. The temperature of the chopper 5a measured by the sensor temperature measuring means 6 is used as a signal for temperature correction when the temperature of an eardrum 4 is derived by calculation by a body temperature calculating means 7.

There are two values $\epsilon 1$ and $\epsilon 2$ that can be selected as the tolerance of the temperature derived by calculation in the body temperature calculating means 7, and switches 2a and 2b are used to determine which value of the foregoing two values is selected. The value of $\epsilon 1$ is determined in advance as a probability error created based on the noise superimposed on the output signal of the filter circuit 5e when a body temperature is derived by calculation from the output signal of the filter circuit 5e in the body temperature calculating means 7 and the value of $\epsilon 2$ is determined in advance as a probability error created based on the noise superimposed on the output signal of the filter circuit 5f when a body temperature is derived by calculation from the output signal of the filter circuit 5f in the body temperature calculating means 7 and At this time, since the time constant of the filter circuit 5e is smaller than that of the filter circuit 5f, the output signal of the filter circuit 5f in comparison with the output signal of the filter circuit 5e becomes a value equivalent to the output signal of a synchronous detector circuit 5d that has been averaged out for a longer time period, resulting in a smaller probability error contained therein. In other words, an inequality of $\epsilon 1 > \epsilon 2$ is established.

Next, a description is made on how an ear type thermometer for women operates and performs. The ear type thermometer for women in the present exemplary embodiment starts to operate when any one of the switch 2a or switch 2b is pushed down. A tolerance selecting means 2 starts to operate when any one of the switch 2a or switch 2b is pushed down, and when the switch 2a is pushed down, $\epsilon 1$ is selected as the applicable tolerance and, when the switch 2b is pushed down, $\epsilon 2$ is selected as the applicable tolerance. A tolerance instructing means 1 furnishes a measurement time determining means 3 with a tolerance selected by the tolerance selecting means 2.

When a tolerance is instructed by the tolerance instructing means 1, the measurement time determining means 3 determines according to the tolerance how much time an infrared ray measuring means 5 is allowed to spend in measuring infrared rays. When the tolerance instructed by the tolerance instructing means 1 is $\epsilon 1$, the time allowed to be spent is determined as $\tau 1$, and when the tolerance instructed is $\epsilon 2$, the time is determined as $\tau 2$.

The infrared ray measuring means 5 has the chopper 5a started to operate when the time to be spent on infrared measurement is instructed by the measurement time instructing means 3. The chopper 5a has the infrared rays from an eardrum 4 received by a pyroelectric infrared sensor 5b intermittently at a predetermined frequency. As a result, the pyroelectric infrared sensor 5b receives the, infrared rays radiated from the eardrum 4 when the chopper 5a passes the infrared rays and receives infrared rays radiated from the chopper 5a itself when the chopper 6a blocks the infrared rays from the eardrum 4.

The pyroelectric infrared sensor 5b produces an output electrical signal indicating variations in the foregoing infrared rays. In a case where the temperature Of the eardrum 4 is higher than the temperature of the chopper 5a, the output electrical signal rises in value when the infrared rays radiated from the eardrum 4 are incident on the pyroelectric infrared sensor 5b and falls when the infrared rays from the eardrum 4 are blocked. The period of the foregoing rises and falls is the same as the operating period of the chopper 5a. Conversely, in a case where the temperature of the eardrum 4 is lower than the temperature of the chopper 6a, the output electrical signal falls in value when the infrared rays radiated from the eardrum 4 are incident on the pyroelectric infrared sensor 5b and rises when the infrared rays from the eardrum 4 are blocked. The period of the rises and falls is the same as the operating period of the chopper 5a. However, the output electrical signal from the pyroelectric infrared sensor 5b is not so large in magnitude, since the output electrical signal utilizes an electrical voltage generated by excitation due to a pyroelectric effect on an insulating material that forms the sensor element, and superimposed with thermal noises that are not negligible in magnitude.

An amplifier circuit 5c amplifies the output signal superimposed with thermal noises and tapped off from the pyroelectric infrared sensor and feed the amplified signal to the synchronous detector circuit 5d, which then rectifies this cyclic signal and feeds the rectified signal to the filter circuits 5e and 5f.

The filter circuit 5e makes the signal fed from the synchronous detector circuit 5d smooth by using a low-pass filter and feeds the smoothed signal to a signal selecting means 5g. On the other hand, the filter circuit 5f makes the signal fed from the synchronous detector circuit 5d smooth by using a low-pass filter and feeds the smoothed signal to the signal selecting means 5g. At this time, since the time constant of the filter circuit 5e is smaller than that of the filter circuit 5f, the output signal of the filter circuit 5f in comparison with the output signal of the filter circuit 5e becomes a value that has been averaged out for a longer time period, resulting in a smaller probability error contained therein. However, the time period $\tau 2$ required of the output signal of the filter circuit 5f to reach a stabilized value becomes longer than the time period $\tau 1$ required of the output signal of the filter circuit 5e to reach a stabilized value.

When a measurement time period instructed by the measurement time determining means 3 is $\tau 1$, the signal selecting means 5g selects the output signal of the filter circuit 5e and feeds the output signal as a measurement value of the infrared rays to the body temperature calculating means 7 at the time when the time period $\tau 1$ has elapsed since the start of operation of the chopper 5a. When a measurement time period instructed by the measurement time determining means 3 is $\tau 2$, the signal selecting means 5g selects the output signal of the filter circuit 5f and feeds the output signal as a measurement value of the infrared rays to the body temperature calculating means 7 at the time when the time period $\tau 2$ has elapsed since the start of operation of the chopper 5a.

The sensor temperature measuring means 6 measures the temperature of the chopper 5a using the thermister and feeds the value of the the temperature as the result of the measuring to the body temperature calculating means 7. The body temperature calculating means 7 calculates the temperature of the eardrum 4 using the measurement value of the infrared ray received from the signal selecting means 5g and feeds them to the body temperature displaying means 8. At this time, the temperature of the chopper 5a furnished from the sensor temperature measuring means 6 is utilized as a correcting signal in deriving by calculation. A body temperature displaying means 8 displays temperatures furnished from the body temperature calculating means 7.

According to the present exemplary embodiment, the measurement time determining means 3 determines an infrared measurement time so as to have the probability error contained in the temperature that is derived by calculation in the body temperature calculating means 7 made equal to the tolerance selected by the user by pushing down the switch 2a or the switch 2b. Since the infrared rays radiated from an eardrum 4 are measure by spending a short time period of τ1 when the selected tolerance is a large value of ε1 and a long time period of τ2 when the selected tolerance is a small value of ε2, the temperature of the eardrum 4 can be measured by spending the shortest possible measurement time needed in accordance to the tolerance selected by the tolerance selecting means 2.

In addition, since the temperature of the eardrum 4 is measured spontaneously just upon having a tolerance selected by pushing down any one of the switches 2a and 2b, a temperature measurement can be carried out promptly without waiting for the start of measurement instructed separately.

Although a description is given to the case where the number of the filter circuits owned by the infrared ray measuring means 5 and the number of the switches owned by the tolerance selecting means 2 are two, respectively in the present exemplary embodiment, it does not matter whether both numbers are increased to three or more, respectively, as a matter of course.

When an ear type thermometer for women intended to deal with a temperature of a living body as the object to be measured in temperature is used as a thermometer for measuring body heat, it is possible for the ear type thermometer for women to be used with the tolerance set to ±0.05° C. when the switch 2a is pushed down and ±0.1° C. when the switch 2b is pushed down. More specifically, a thermometer can be used to perform two different purposes by switching the functions thereof, one as a thermometer for women with ±0.05° C. in tolerance although the temperature measurement time takes long or the other as a general purpose thermometer with an accuracy in temperature measurement not so high as the thermometer for women although the temperature measurement can be carried out in a shorter time period.

(Second Exemplary Embodiment)

Figure 2:
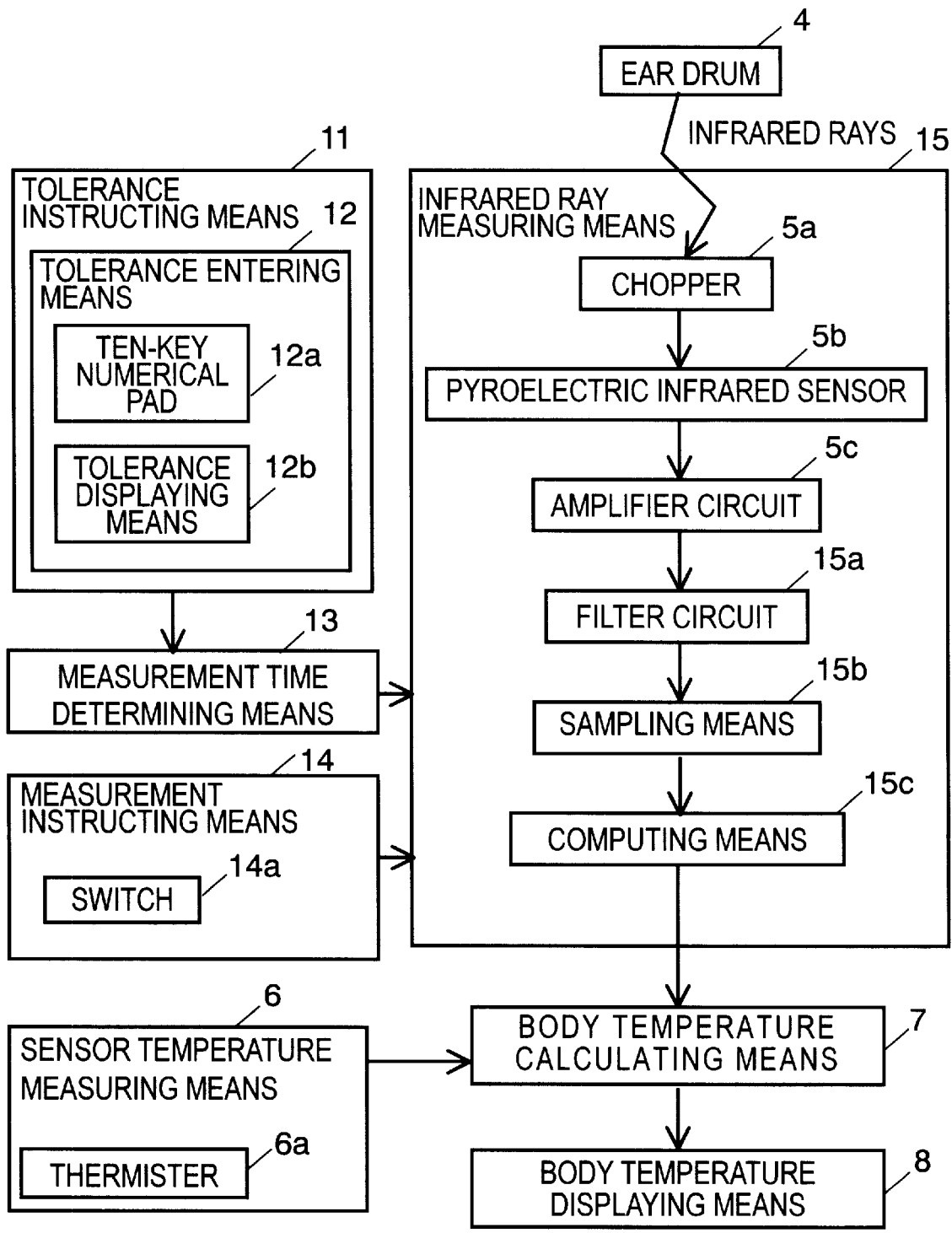
FIG. 2 is a block diagram of an ear type thermometer for women in a second exemplary embodiment of the present invention.

FIG. 2 is a block diagram of an ear type thermometer for women in a second exemplary embodiment of the present invention. In FIG. 2, the reference numeral 11 is a tolerance instructing means to instruct about a tolerance. The reference numeral 12 is a tolerance entering means to enter a tolerance numerically, comprising a ten-key numerical pad for entering numerical values of zero to nine and a decimal point and also for canceling already entered numerical values, and a tolerance displaying means 12b to allow the numeral values of zero to nine and decimal point to be displayed. The reference numeral 13 is a measurement time determining means to determine the time period spent in measuring infrared rays. The reference numeral 14 is a measurement instructing means for instructing to start a temperature measurement, having a switch 14a provided therein. The reference numeral 16 is an infrared ray measuring means to measure infrared rays radiated from an object to be measured in temperature, i.e., an eardrum 4, comprising a filter circuit 15a, a sampling means 15b to sample an analog signal and a computing means 15c to derive by calculation a measurement value of infrared rays based on the sampled signal values. In addition to the foregoing, the same components as used in the first exemplary embodiment are assigned the same reference numerals and detailed descriptions of such components are omitted.

The filter circuit 15a is formed of a low-pass filter which does not pass the signals having higher frequencies than a frequency determined in advance.

By utilizing the concept of discrete Fourier transform, the computing means 15c derives by calculation the magnitude of a signal having the same frequency component as the operating frequency of a chopper 5a out of the various frequency components contained in the output signal of the filter circuit 15a based on a series of signal values sampled by the sampling means 15b.

Next, a description is made on how an ear type thermometer for women operates and performs. The ear type thermometer for women in the present exemplified embodiment starts an advance preparation for temperature measurement when the switch 14a in the measurement instructing means 14 is pushed down after the entry of a tolerable probability error by the tolerance entering means 12.

The probability error tolerated by the user is entered in a numerical value via the ten-key numerical pad 12a of the tolerance entering means 12. The entered numeral value of tolerance is displayed by the tolerance displaying means 12b. The user checks the once entered numerical value of tolerance on the tolerance displaying means 12 and, when the numerical value is found in error, the wrong numerical value is cancelled and a correct tolerance is allowed to be entered again by operating the ten-key numerical pad 12a. For the sake of convenience in explanation, the value of tolerance entered from the ten-key numerical pad 12a is expressed as ε3.

The tolerance instructing means 11 furnishes the measurement time determining means 13 with the value ε3 of tolerance entered to the tolerance entering means 12. The measurement time determining means 13 derives by calculation a time τ3 according to an equation (5) as below and feed the time τ3 to the infrared ray measuring means 15.

$$\tau 3 = \frac{K}{\varepsilon 3^2} \quad (5)$$

where ε3 is a value fed from the tolerance instructing means 11 and K is a positive constant.

The measurement instructing means 14 remains in waiting until the switch 14a is pushed down and feeds an instruction to start measurement to the infrared ray measuring means 15 when the switch 14a is pushed down. Upon receiving the instruction to start measurement from the measurement instructing means 14, the infrared ray measuring means 15 is to have the operation of the chopper 5a started as an advance preparation for temperature measurement.

The chopper 5a is to have the infrared rays radiated from the eardrum 4 irradiated on the pyroelectric infrared sensor 5b intermittently with predetermined periodicity. As a result, the infrared rays radiated from the eardrum 4 are incident on the pyroelectric infrared sensor 5b when the chopper 5a allows the infrared rays to pass and the infrared rays radiated from the chopper 5a itself are incident on the pyroelectric infrared sensor 5b when the chopper 5a blocks the infrared rays. For the sake of convenience in explanation, the operating period of the chopper 5a is expressed as T in the following.

The pyroelectric infrared sensor 5b generates an output electrical signal corresponding to the variation of the infrared rays of above. When the temperature of the eardrum 4 is higher than the temperature of the chopper 5a, the output electrical signal rises upon receiving the infrared rays radiated from the eardrum 4 and falls upon blocking the infrared rays radiated from the eardrum 4, thus proving a signal repeating at the period T. Conversely, when the temperature of the eardrum 4 is lower than the temperature of the chopper 5a, the output electrical signal falls upon receiving the infrared rays radiated from the eardrum 4 and rises upon blocking the infrared rays radiated from the eardrum 4, thus proving a signal repeating at the period T. However, the output electrical signal from the pyroelectric infrared sensor 5b is not so large in magnitude, since the output electrical signal utilizes an electrical voltage generated by excitation due to a pyroelectric effect on an insulating material that forms the sensor element, and superimposed with thermal noises that are not negligible in magnitude.

The amplifier circuit 5c feeds the output signal of the pyroelectric infrared sensor 5b, which is superimposed with thermal noises, to the filter circuit 15 after applying amplification thereto. The filter circuit 15a does not pass the signal components out of the signal fed from the amplifier circuit 5c, which have a frequency of N/2T or higher, the frequency of N/2T corresponding to N/2 times the operating frequency 1/T of the chopper 5a, where N is a nonnegative integer, and passes without attenuation the signal components having a frequency not exceeding the operating frequency 1/T of the chopper 5a. The output signal of the filter circuit 15a is fed to the sampling means 15b. It is preferred to determine the value of N as 10 or more. Since the signal fed to the filter circuit 15a as an input signal is a signal repeating at the period T and superimposed with thermal noises, the waveform of the signal appearing as an output of the filter circuit 15a is also a signal repeating at the period T and superimposed with thermal noises limited with the bandwidth after the influence of the starting up response of the pyroelectric infrared sensor 5b, amplifier circuit 5c and filter circuit 15a is eliminated.

Upon eliminating the foregoing influence of the starting up response, the infrared ray measuring means 15 assumes that an advance preparation for measurement is finished and has the operation of the sampling means 15b and computing means 15c started newly while having the foregoing operation of the chopper 5a, pyroelectric infrared sensor 5b, amplifier circuit 5c and filter circuit 15a kept continuing. The time when the influence of the starting up response disappears is determined in advance based on the physical properties of the chopper 5a, pyroelectric infrared sensor 5b, amplifier circuit 5c and filter circuit 15a. The smallest nonnegative integer M is derived from an inequality of:

$$M \geq \frac{\tau 3}{T} \quad (6)$$

where $\tau 3$ is the time instructed by the measurement time determining means 13 and T is an operating period of the chopper 5a, and the sampling means 15b samples the signal fed from the filter circuit 15a with a period of T/N corresponding to 1/N of the operating period of the chopper 5a, i.e., at a frequency of N/T during the time period of M operating period of the chopper 5a, i.e., during the time period of M×T. Then, a string of sampled signals are fed to the computing means 15c. For the sake of convenience in explanation, the values sampled by the sampling means 15b are expressed as s (0), s (1), s (2), . . . , s (M×N−1) in the order of sampling.

The computing means 15c derives by calculation a measurement value of the infrared rays radiated from the eardrum 4 by using the foregoing string of sampled signals as follows:

$$\sum \cos = \sum_{K=0}^{M \times N-1} \left\{ s(k) \times \cos\left(2\pi \times \frac{k}{N}\right) \right\} \quad (7)$$

$$\sum \sin = \sum_{K=0}^{M \times N-1} \left\{ s(k) \times \sin\left(2\pi \times \frac{k}{N}\right) \right\}$$

$$V_{PP} = \frac{2}{M \times N} \times \sqrt{\left(\sum \cos\right)^2 + \left(\sum \sin\right)^2}$$

After this, what is performed by the sensor temperature measuring means 6, body temperature calculating means 7 and body temperature displaying means 8 is identical with what is performed in the first exemplary embodiment and, therefore, a detailed description thereof is omitted.

After the influence of the starting up response disappears, the output signal of the filter circuit 15a becomes the repeated signal with the period T provided that the component of superimposed thermal noises is neglected. Further, since the output signal of the filter circuit 15a does not contain the signal component of the frequency of N/2T or higher and the sampling frequency of N/T of the sampling means 15b satisfies the Nyquist criterion, the signal component having the same frequency as the operating frequency 1/T of the chopper 5a out of the signal components of a variety of frequencies contained in the output signal of the filter circuit 15a, i.e., the voltage in amplitude of the signal component indicating the measurement value of infrared rays radiated from the eardrum 4 and expressed in terms of a peak-to-peak value can be derived by calculation based on s (0), s (1), s (2), . . . , s (N−1) by performing a discrete Fourier transform as follows:

$$\sum \cos 2 = \sum_{K=0}^{N-1} \left\{ s(k) \times \cos\left(2\pi \times \frac{k}{N}\right) \right\} \quad (8)$$

$$\sum \sin 2 = \sum_{K=0}^{N-1} \left\{ s(k) \times \sin\left(2\pi \times \frac{k}{N}\right) \right\}$$

$$V_{PP} = \frac{2}{N} \times \sqrt{\left(\sum \cos 2\right)^2 + \left(\sum \sin 2\right)^2}$$

In practice, since thermal noises are superimposed on the output signal of the filter circuit 15a, the measurement value of infrared rays derived by calculation is caused to show fluctuations due to the thermal noises even if the temperatures of the eardrum 4 and chopper 5a are stabilized, resulting in a small amount of variation in the values derived by calculation for each respective period of chopper operation by using the equation (8). The extent of the variation can be reduced inversely with a square root of M by taking an average value over the time period of M period of the operation of the chopper 5a. Due to the periodicity of a trigonometric function, the computational formula of the equation (7) ends up performing the same processing as requiring the average value, thereby allowing the magnitude of the error contained in the infrared measurement value derived by calculation by the computing means 15c to vary inversely with a square root of M.

When the operating period T of the chopper 5a is kept constant, it is known from the equation (6) that M is proportionate to $\tau 3$. On the other hand, $\tau 3$ varies inversely with a square of tolerance $\epsilon 3$ according to the equation (5). In other words, it can be known that the magnitude of the tolerance contained in the infrared measurement value derived by calculation from the computing means 15c is proportionate to ∈3.

Therefore, according to the present exemplary embodiment, it becomes possible for the temperature of an eardrum 4 to be measured in the shortest measurement time period corresponding to ∈3 while the user maintaining the error included in the temperature derived by calculation from the body temperature calculating means 7 at the tolerance ∈3 entered from the tolerance entering means 12 by determining the proportionality constant K of the equation (5) in consideration of the computation formula used at the time of deriving by calculation the temperature of the eardrum 4 in the body temperature calculating means 7.

In addition, an instruction alone of a tolerance by the tolerance instructing means 11 does not initiate an operation of the infrared ray measuring means 15 and an infrared ray measurement is initiated only upon pushing down the switch 14a in the measurement instructing means 14, thereby allowing temperatures of a plurality of eardrums to be measured continuously with the same tolerance by pushing down the switch 14a two or more times after making the setting of the tolerance in advance. In other words, it is not needed for the tolerance to be set many times.

Although a description is made in the second exemplary embodiment by paying attention to the probability error only based on the assumption that a mechanical error can be neglected, the tolerance of the probability error can be made as ∈3−∈0 when a predetermined value ∈0>0 is needed to be taken into consideration, thereby determining the infrared measurement time according to an equation (9) in place of the equation (5).

$$\tau 3 = \frac{K}{(\varepsilon 3 - \varepsilon 0)^2} \quad (9)$$

However, it is needless to say that an arrangement is made to allow only a larger value than the mechanical error ∈0 to be fed as the tolerance at that time.

Although a description is given to the case where the user makes the setting of a tolerance by using a tolerance instructing means in the present exemplary embodiment, it is also possible for the tolerance to be determined at the time of production or shipment of an ear type thermometer for women by writing in EPROM or using a jumper wire, thereby configuring so as not to allow the user to manipulate the tolerance thereafter. Accordingly, ear type thermometers for women with plural kinds of specifications, which are different in temperature measurement accuracy and measurement times period from one another, are allowed to be produced by the same production steps and skills except for making the setting of tolerance information.

(Third Exemplary Embodiment)

Figure 3:
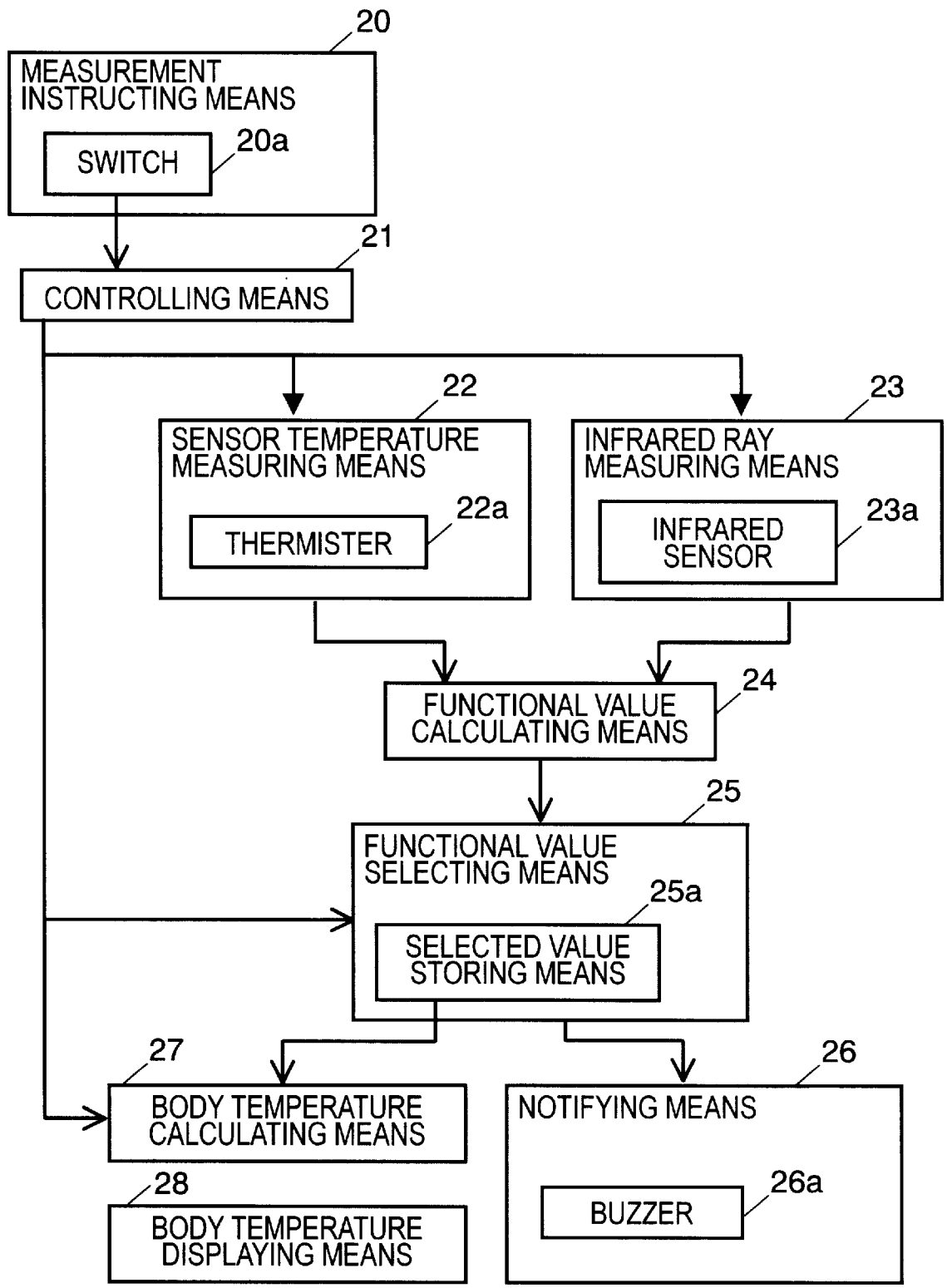
FIG. 3 is a block diagram of an ear type thermometer for women in a third exemplary embodiment of the present invention.

FIG. 3 is a block diagram of an ear type thermometer for women in a third exemplary embodiment of the present invention.

In FIG. 3, the reference numeral 20 is a measurement instructing means to be used in instructing to carry out a body temperature measurement and to be provided with a switch 20a therein. The reference numeral 21 is a controlling means. The reference numeral 22 is a sensor temperature measuring means to measure the temperature of an environment, in which the ear type thermometer for women is used, and a thermister 22a is provided therein. The reference numeral 23 is an infrared ray measuring means to measure infrared rays radiated from an eardrum and provided with an infrared sensor 23a therein. The infrared sensor 23a is realized by the use of a kind of thermal type infrared sensors, i.e., thermopile. The case of the infrared sensor 23a is thermally coupled with the thermister 22a. The reference numeral 24 is a functional value calculating means to derive by calculation a functional value that is in a simple increasing relation with body temperatures. The reference numeral 25 is a functional value selecting means to select the maximum value of the functional values derived by calculation in the functional value calculating means 24 and provided with a selected value storing means 25a therein, whereby a selected value is stored. The selected value storing means 25a stores values selected by the functional value selecting means 25. The reference numeral 26 is a notifying means to notify the user of the fact that a value stored in the selected value storing means 25a is renewed when such a renewal takes place, and provided with a buzzer 26a therein. The reference numeral 27 is a body temperature calculating means to derive body temperatures by calculation and the reference numeral 28 is a body temperature displaying means to display the body temperatures derived by calculation.

The ear type thermometer for women in the present exemplary embodiment is to start to operate when the user pushes down the switch 20a of the measurement instructing means 20, and to perform repeatedly the process comprising the steps of measuring an ambient temperature by the sensor temperature measuring means 22, measuring infrared rays by the infrared ray measuring means 23, deriving by calculation a functional value from those two measurement values by using the functional value calculating means 24 and selecting the maximum value of the functional values by the functional value selecting means 25 during the time period when the switch 20a is being pushed down. When the switch 20a is released from the state of being pushed down, the body temperature calculating means 27 derives by calculation a body temperature based on the value selected by the functional value selecting means 25 and then the body temperature displaying means 28 displays the body temperature derived by calculation.

Figure 4:
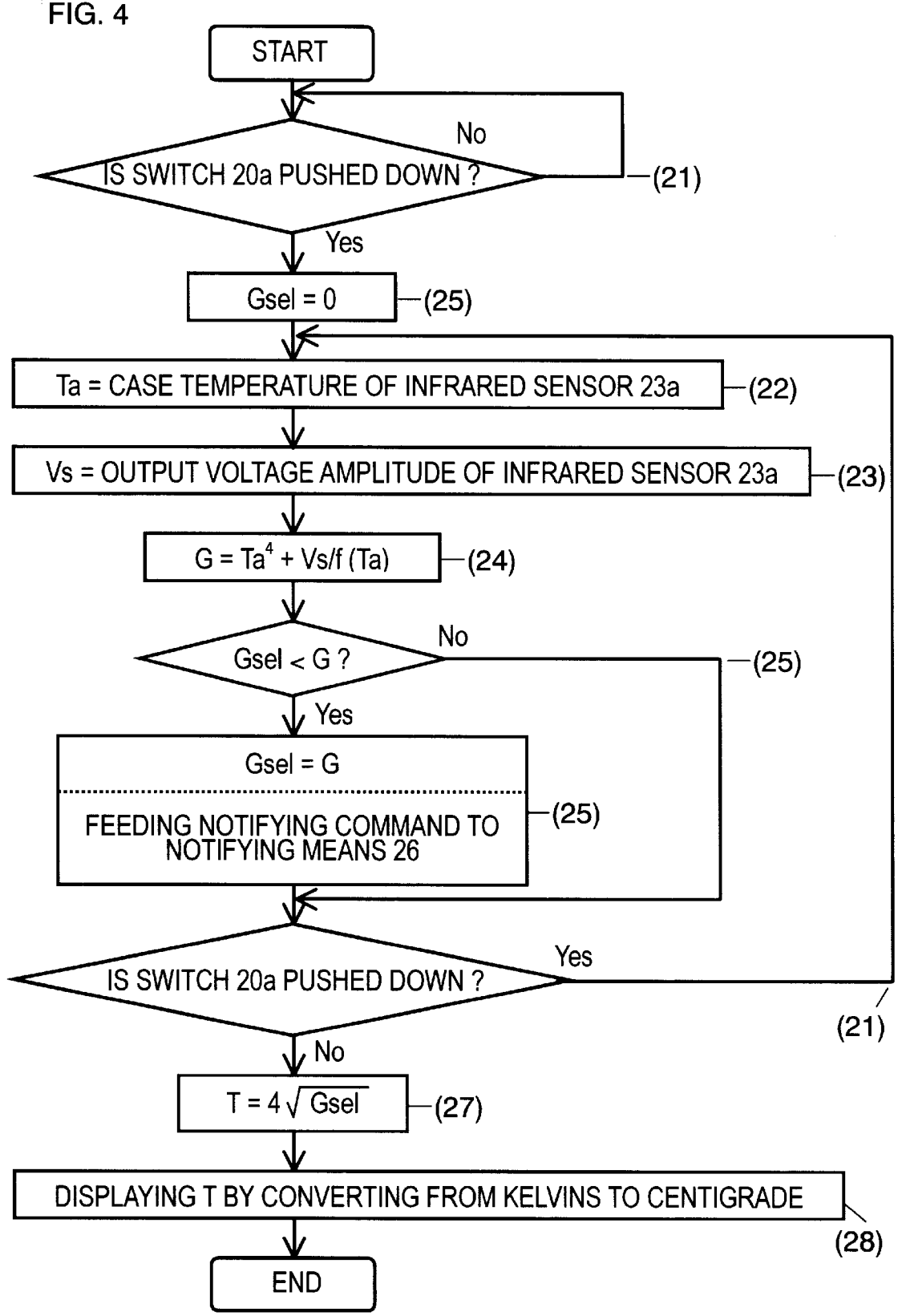
FIG. 4 is a flow chart to show how an ear type thermometer for women in a third exemplary embodiment of the present invention operates.
Figure 5:
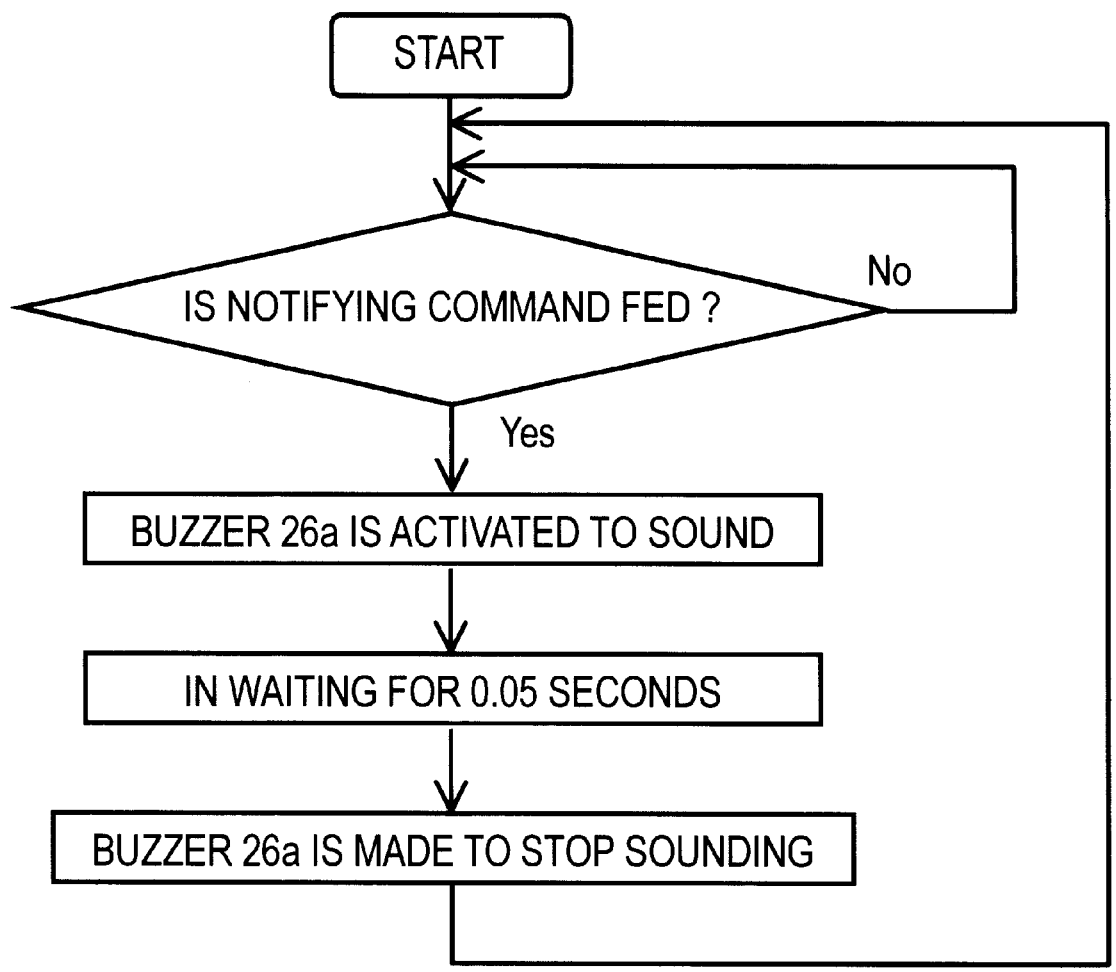
FIG. 5 is a flow chart to show how a notifying means 26 of an ear type thermometer for women operates.

FIG. 4 is a flow chart to show how the ear type thermometer for women operates and FIG. 5 is a flow chart to show how the notifying means 26 of the ear type thermometer for women operates. In FIG. 4, the reference numerals of the elements performing respective operations are indicated in parentheses.

Next, at description is made on how the ear type thermometer for women operates and performs with reference to FIG. 4.

The controlling means 21 waits for the switch 20a inside the measurement instructing means 20 to be pushed down.

When the switch 20a is pushed down, a control signal is generated from the controlling means 21 and the functional value selecting means 25 initializes the value Gsel stored in the selected value storing means 25a to 0.

Then, the sensor temperature measuring means 22 measures the temperature of the case of infrared sensor 23a as an ambient temperature by using the thermister 22a and feeds the temperature expressed as a temperature Ta in kelvins (K) to the functional value calculating means 24.

Subsequent to that, the infrared ray measuring means 23 measures the intensity of infrared rays incident on the infrared sensor 23a to obtain an output voltage Vs, which is then fed to the functional value calculating means 24.

By using the ambient temperature Ta derived from the sensor temperature measuring means 22 and the infrared measurement value Vs fed from the infrared ray measuring means 23, the functional value calculating means 24 derives by calculation a functional value G corresponding to the fourth power of the body temperature expressed in kelvins (K) and determined by an equation (10).

$$G = T_a^4 + \frac{V_s}{f(T_a)} \quad (10)$$

where f(Ta) is a polynomial expression determined according to the equation (2) described relative to the conventional technology. The constants A, B and C corresponding to the coefficients in the polynomial expression are determined in advance according to the characteristics of the infrared sensor 23a. The functional value G thus derived by calculation is in a simple increasing relation with body temperatures.

After the functional value G is derived by calculation in the functional value calculating means 24, the functional value selecting means 25 makes a comparison between the value Gsel stored in the selected value storing means 25a and the functional value G. As a result of the comparison, when the value Gsel is smaller than the functional value G, the value Gsel is renewed to the same value as the functional value G and also finishes the notifying means 26 with a notifying order. When the value Gsel is equal to or larger than the functional value G, the value Gsel is not renewed and no notifying order is furnished. As a result, the value Gsel ends up storing the maximum value of the functional values G derived by calculation in the functional value calculating means 24.

Subsequent to that, the status of the switch 20a is checked by the controlling means 21. When the switch 20a is found to be pushed down, a series of processes from a measurement of the ambient temperature carried out by the sensor temperature measuring means 22 to a determination of the status of the switch 20a made by the controlling means 21 are repeated again. On the other hand, when the switch 20a is not pushed down, the foregoing series of processes are not repeated and the body temperature calculating means 27 starts to operate as described later.

The notifying means 26 operates concurrently with other processing units and, immediately upon finishing a notifying order as FIG. 3 shows, the buzzer 26a starts to sound and the sounding of the buzzer 26a is stopped in 50 ms. The buzzer 26a is in a waiting status until another notifying order is received. Unless another notifying order is furnished, the buzzer 26a is never activated.

Back again to FIG. 4, the body temperature calculating means 27 retrieves the value Gsel stored in the selected value storing means 25a and derives by calculation a body temperature T expressed in kelvins (K) according to an equation (11) as follows:

$$T = \sqrt[4]{G_{sel}} \quad (11)$$

The body temperature displaying means 28 displays the absolute temperature T converted to a temperature expressed in Celsius.

According to the present exemplary embodiment, every time when the ambient temperature and infrared rays radiated from the eardrum are measured, a functional value G corresponding to the fourth power of a body temperature is derived by calculation in the functional value calculating mean 24, and after the maximum value of the functional values is selected as Gsel by the functional value selecting means 25, a bi-quadric root of the selected value Gsel is calculated only once by the body temperature calculating means 27 and the time period spent in deriving by calculation a functional value in the functional value calculating means 24 is allowed to be reduced from the time period required by numerical computations to derive by calculation a bi-quadric root each time, when compared with the case where a body temperature itself is derived by calculation every time as with a conventional ear type thermometer for women.

Since the buzzer 26 is made to sound every time the selected value Gsel is renewed, the user is allowed to learn to know by the sound of the buzzer 26 whether the measurement result of body temperatures is changing to a higher value or not during the time period when the switch 20a is being pushed down and the direction of a probe is being changed. By suspending the pushing down of the switch 20a when the buzzer 26 is no longer sounding, it is actually felt that the measurement result of body temperatures is stabilized sufficiently, thereby allowing the user to rely on the ear type thermometer for women with confidence.

Although the end of the body temperature measurement is judged only by the status of the switch 20a with the present exemplary embodiment, it does not matter if a clocking means to measure an elapsed time period after the switch 20a is pushed down is provided and the body temperature measurement is continued, even if the user stopped pushing down the switch 20a, until a predetermined time period of three seconds, for example, has passed according to the time measurement result from the clocking means. Accordingly, when the user is accustomed to operating the ear type thermometer for women and able to direct the probe correctly towards the eardrum without depending on the sounding of the buzzer 26a, the user is allowed to display the temperature of the eardrum accurately as the body temperature only by changing the direction of the probe a little upon pushing down the switch 20a momentarily without spending the labor of keeping the pushing down of the switch 20a. In this case, the sounding of the buzzer 26a may be stopped when the value Gsel selected by the selected value storing means 25a is renewed or the buzzer 26a may be activated to sound when the time measurement result by the clocking means reaches a value determined in advance.

Another approach is that the functional value derived by calculation in the functional value calculating means 24 is treated as a square root of the right side of the equation (10) and the body temperature calculating means 27 may derive by calculation a square root of the value Gsel furnished from the functional value selecting means 25 to obtain a body temperature, thereby allowing the time period, which is required of the functional value calculating means 24 in deriving by calculation a functional value when a bi-quadratic root is obtained by performing two times of a square root calculation, to be reduced by one time of the time period required in numerical computations of a square root when compared with the case where a body temperature itself is derived by calculation each time as with the conventional ear type thermometer for women.

(Fourth Exemplary Embodiment)

Figure 6:
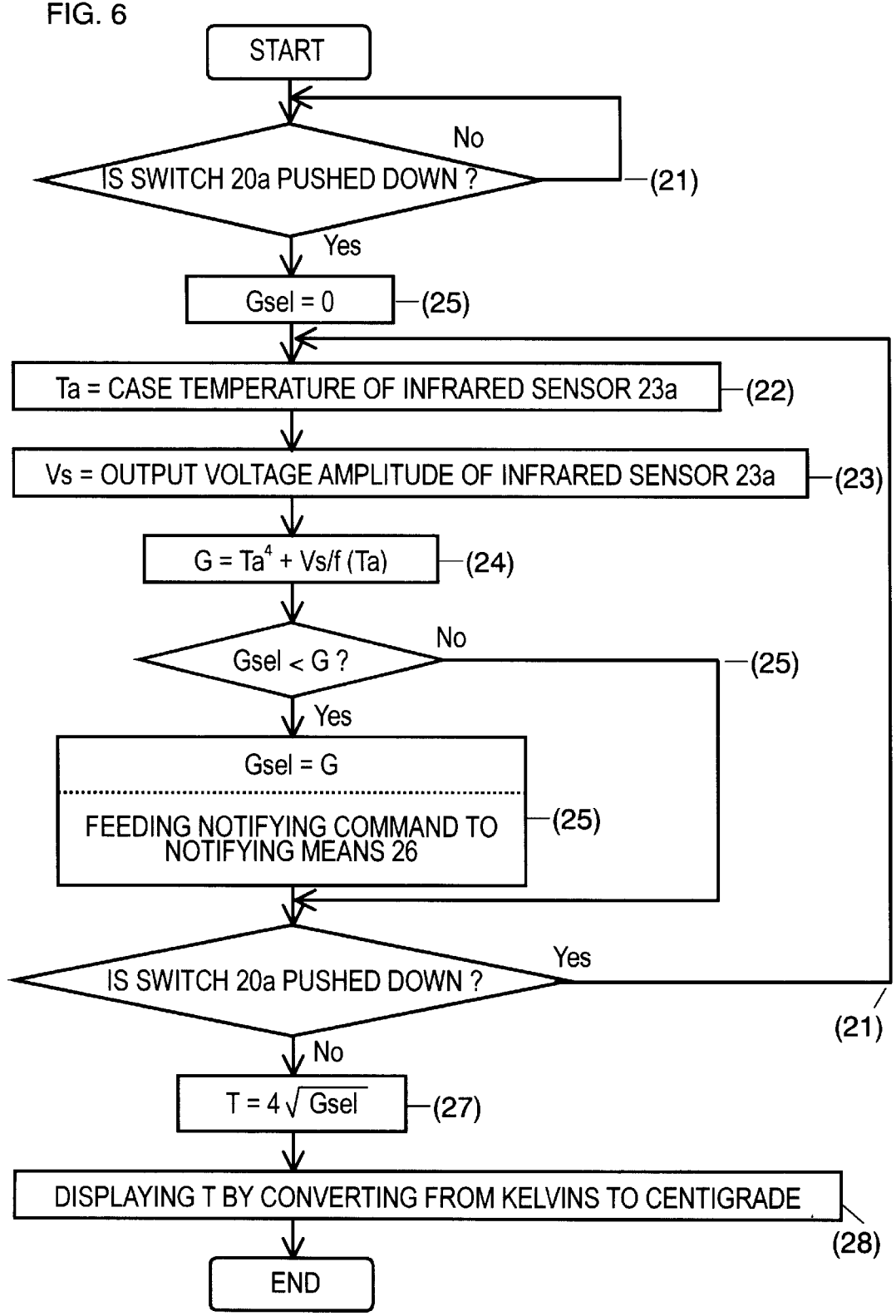
FIG. 6 is a flow chart to show how an ear type thermometer for women in a fourth exemplary embodiment of the present invention operates.

An ear type thermometer for women can be configured to operate as described in a flow chart of FIG. 6. What is different between the present exemplary embodiment and the third exemplary embodiment in terms of operation of an ear type thermometer for women is in the measurement of ambient temperature Ta at the sensor temperature measuring means 22 to be performed only once with the present exemplary embodiment.

Next, a description is given to how an ear type thermometer for women in a fourth exemplary embodiment of the present invention operates and performs with reference to FIG. 6. When the switch 20a is pushed down, the controlling means 21 generates a control signal and the functional value selecting means 25 initializes the value Gsel stored in the selected value storing means 25a to 0.

Then, the sensor temperature measuring means 22 measures the temperature of the case of the infrared sensor 23a as an ambient temperature by using the thermister 22a and feeds the temperature Ta expressed in kelvins (K) to the functional value calculating means 24.

Subsequent to that, the infrared ray measuring means 23 measures the intensity of infrared rays incident on the infrared sensor 23a to obtain an output voltage Vs, which is then fed to the functional value calculating means 24.

By using the ambient temperature Ta derived from the sensor temperature measuring means 22 and the infrared measurement value Vs fed from the infrared ray measuring means 23, the functional value calculating means 24 derives by calculation a functional value G corresponding to the fourth power of the body temperature expressed in kelvins (K) and determined by an equation (12).

$$G = T_a^4 + \frac{V_s}{f(T_a)} \quad (12)$$

where f(Ta) is a polynomial expression determined according to the equation (2) described relative to the conventional technology. The constants A, B and C corresponding to the coefficients in the polynomial expression are determined in advance according to the characteristics of the infrared sensor 23a. The functional value G thus derived by calculation is in a simple increasing relation with body temperatures.

After the functional value G is derived by calculation in the functional value calculating means 24, the functional value selecting means 25 makes a comparison between the value Gsel stored in the selected value storing means 25a and the functional value G. As a result of the comparison, when the value Gsel is smaller than the functional value G, the value Gsel is renewed to the same value as the functional value G and also furnishes the notifying means 26 with a notifying order. When the value Gsel is equal to or larger than the functional value G, the value Gsel is not renewed and no notifying order is furnished. As a result, the value Gsel ends up storing the maximum value of the functional values G derived by calculation in the functional value calculating means 24.

Subsequent to that, the status of the switch 20a is checked by the controlling means 21. When the switch 20a is found to be pushed down, a series of processes from an infrared measurement carried out by the infrared ray measuring means 23 to a determination of the status of the switch 20a made by the controlling means 21 are repeated again. While the foregoing processes are being repeated, the sensor temperature measuring means 22 continues feeding the ambient temperature Ta measured in the beginning as is. On the other hand, when the switch 20a is not pushed down, the foregoing series of processes are not repeated and the body temperature calculating means 27 starts to operate.

How the notifying means 26, body temperature calculating means 27 and body temperature displaying means 28 are operated is entirely the same as described in the third exemplary embodiment and a detailed description thereof is omitted.

Next, a description is made on how the value of the ambient temperature Ta finished by the sensor temperature measuring means 22 is different between the third exemplary embodiment and the present exemplary embodiment. A working prototype of the ear type thermometer for women as described in the third exemplary embodiment is prepared and used to carry out various measurements. The value Ta furnished as an output from the sensor temperature measuring means 22 increases bit by bit when a body temperature continues to be measured by having the probe inserted in the ear hole and the magnitude of the temperature increase is around 0.03° C. at the maximum when the body temperature continues to be measured for 10 seconds. This increment of temperature increase is not reflected to the output Ta of the sensor temperature measuring means 22 in the present exemplary embodiment and, therefore, when a body temperature continues to be measured for 10 seconds, an error ranging approximately from 0.02° C. to 0.03° C. at the maximum in magnitude is contained therein.

The effect of this error brought about to the equation (1) is most prominently on the term (13) as follows:

$$T_a^4 \quad (13)$$

Since the term involving f(Ta) can be almost neglected, an error of 0.02° C. to 0.03° C. is known to be contained even in the body temperature of eardrum ultimately derived by calculation. However, this much error is not considered to make a significant problem as the accuracy of a thermometer.

According to the present exemplary embodiment, when a functional value G corresponding to the fourth power of a body temperature is derived by calculation in the functional value calculating means 24, an infrared measurement value Vs only is measured again each time by the infrared ray measuring means 23 and the ambient temperature Ta uses repeatedly the value measured in the beginning, thereby allowing the time period, which is required to derive by calculation each respective functional value, to be reduced further by the amount corresponding to the time period required of the sensor temperature measuring means 22 to measure the resistance value of the thermister 22a and the computation time required of the equation (3) to derive by calculation the ambient temperature based on the resistance value of the thermister 22a.

(Fifth Exemplary Embodiment)

Figure 7:
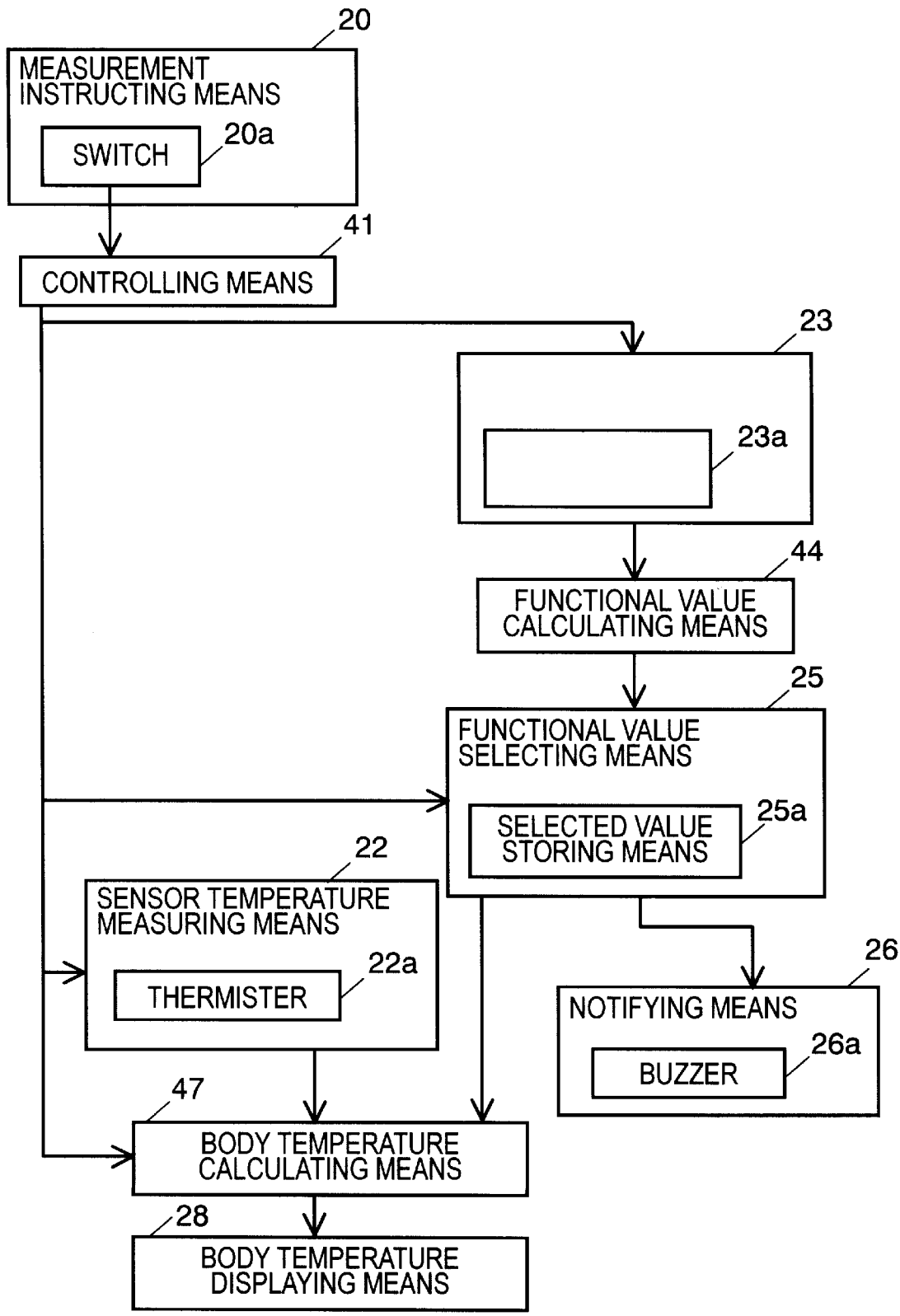
FIG. 7 is a block diagram of an ear type thermometer for women in a fifth exemplary embodiment of the present invention.
Figure 8:
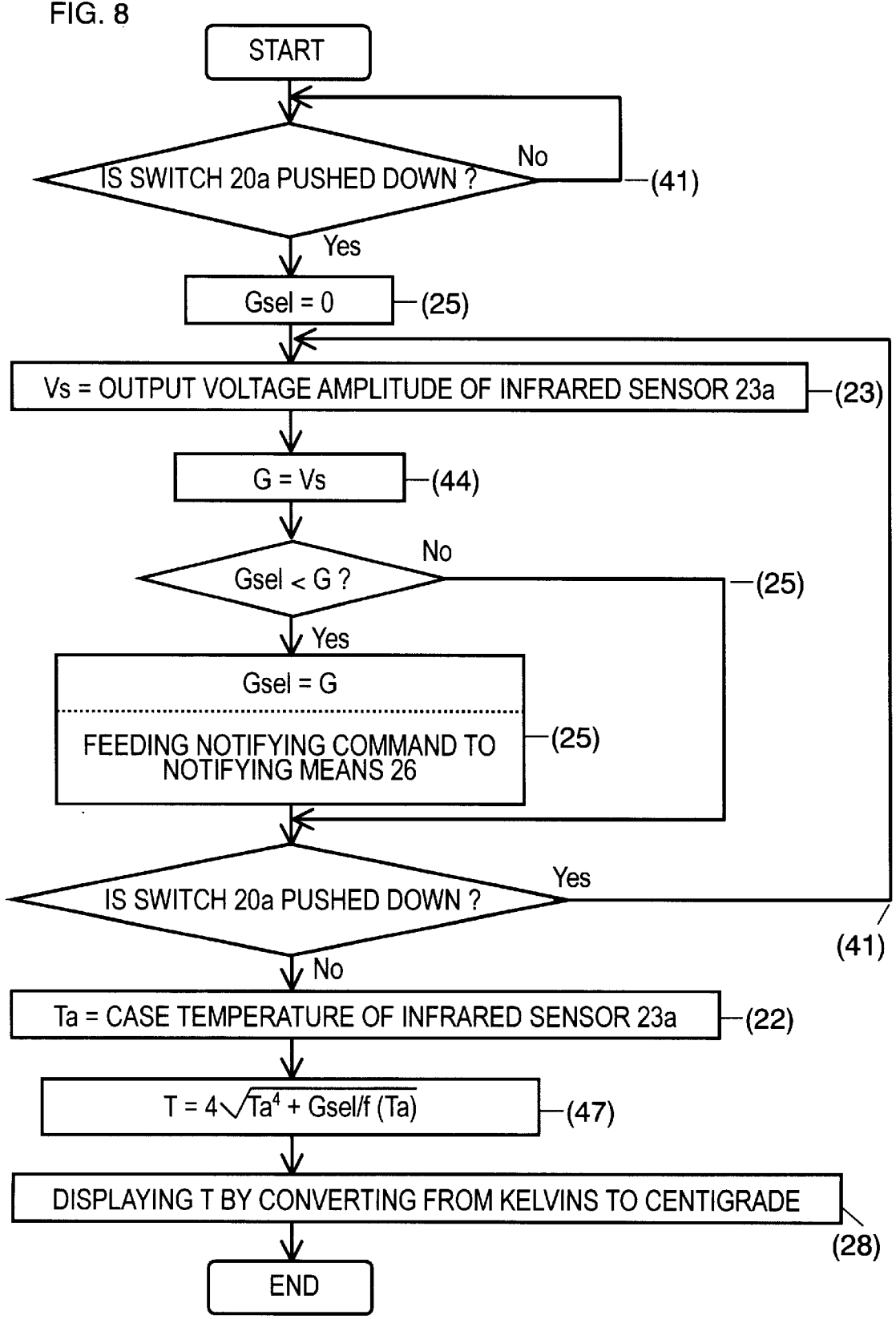
FIG. 8 is a flow chart to show how the ear type thermometer in the fifth exemplary embodiment of the present invention operates.

FIG. 7 is a block diagram of an ear type thermometer for women in a fifth exemplary embodiment of the present invention. In FIG. 7, the reference numeral 41 is a controlling means, 44 is a functional value calculating means and 47 is a body temperature calculating means. With respect to other elements that have the same structure as in the third exemplary embodiment, the same reference numerals are assigned thereto. FIG. 8 is a flow chart to show how the ear type thermometer in the present exemplary embodiment operates. In FIG. 8, the reference numerals of the elements performing respective operations are indicated in parentheses.

Next, a description is made on how the ear type thermometer for women operates and performs with reference to FIG. 8. The controlling means 41 waits for the switch 20a inside the measurement instructing means 20 to be pushed down. When the switch 20a is pushed down, a control signal is generated from the controlling means 41 and the functional value selecting means 25 initializes the value Gsel stored in the selected value storing means 25a to 0.

Then, the infrared ray measuring means 23 measures the intensity of infrared rays incident on the infrared sensor 23a to obtain an output voltage Vs, which is then fed to the functional value calculating means 44. The value of the output voltage Vs is adjusted in advance so as to be made positive when the temperature of an area of the eardrum radiating the infrared rays, which are incident on the infrared sensor 23a, is higher than the temperature of the case of infrared sensor 23a, and negative when the temperature of the area of the eardrum is lower than the temperature of the case of infrared sensor 23a.

The functional value calculating means 44 feeds the infrared measurement value Vs furnished from the infrared ray measuring means 23, as is, to the functional value selecting means 25 as a functional value G.

The functional value selecting means 25 makes a comparison between the value Gsel stored in the selected value storing means 25a and the functional value G fed from the functional value calculating means 44. As a result of the comparison, when the value Gsel turns out smaller than the functional value G, the value Gsel is renewed to a value that is equal to the functional value G and also a notifying order is given to the notifying means 26. When the result of comparison reveals that the value Gsel is equal to or higher than the functional value G, the value Gsel is not renewed and the notifying order is not issued. As a result, the value Gsel ends up storing the magnum value of the functional values G derived by calculation in the functional value calculating means 44.

Subsequent to that, the status of the switch 20a is checked by the controlling means 41. When the switch 20a is found to be pushed down, a series of processes from an infrared measurement carried out by the infrared ray measuring means 23 to a determination of the status of the switch 20a made by the controlling means 41 are repeated again. On the other hand, when the switch 20a is not pushed down, the foregoing series of processes are not repeated and the sensor temperature measuring means 22 starts to operate.

The sensor temperature measuring means 22 measures the temperature of the case of infrared sensor 23a as an ambient temperature by using the thermister 22a and feeds the temperature expressed as a value Ta in kelvins (K) to the body temperature calculating means 47.

Then, the body temperature calculating means 47 derives by calculation a body temperature expressed in kelvins (K) according to an equation (14) by using the value Gsel stored in the selected value storing means 25a and the ambient temperature Ta furnished from the sensor temperature measuring means 22 as follows:

$$T = \sqrt[4]{T_a^4 + \frac{G_{sel}}{f(T_a)}} \quad (14)$$

where f(Ta) is a polynomial expression determined according to the equation (2) described relative to the conventional technology. The constants A, B and C corresponding to the coefficients in the polynomial expression are determined in advance according to the characteristics of the infrared sensor 23a and are always positive regardless of the value of Ta.

Here, the body temperature T derived by calculation according to an equation (15), which is derived by replacing Gsel in the equation (14) with each respective functional value G used by the functional value selecting means 25 to select the value Gsel, is in a simple increasing relation with the functional value G.

$$T = \sqrt[4]{T_a^4 + \frac{G}{f(T_a)}} \quad (15)$$

Therefore, it is learned to know that the body temperature T derived by calculation according to the equation (14) against the value Gsel, which is the maximum value of the functional value G, is equal to the maximum value of body temperatures derived by calculation individually according to the equation (15) against each respective functional value G obtained each time when a body temperature measurement is carried out.

The body temperature displaying means 28 displays the absolute temperature T converted to a temperature expressed in Celsius. According to the present exemplary embodiment, since the functional value calculating means 44 uses the infrared measurement value Vs obtained via the infrared ray measuring means 23, as is, to obtain a functional value, the time period spent in deriving by calculation respective functional values is allowed to be further reduced in comparison with the case in the fourth exemplified embodiment.

(Sixth Exemplary Embodiment)

Figure 9:
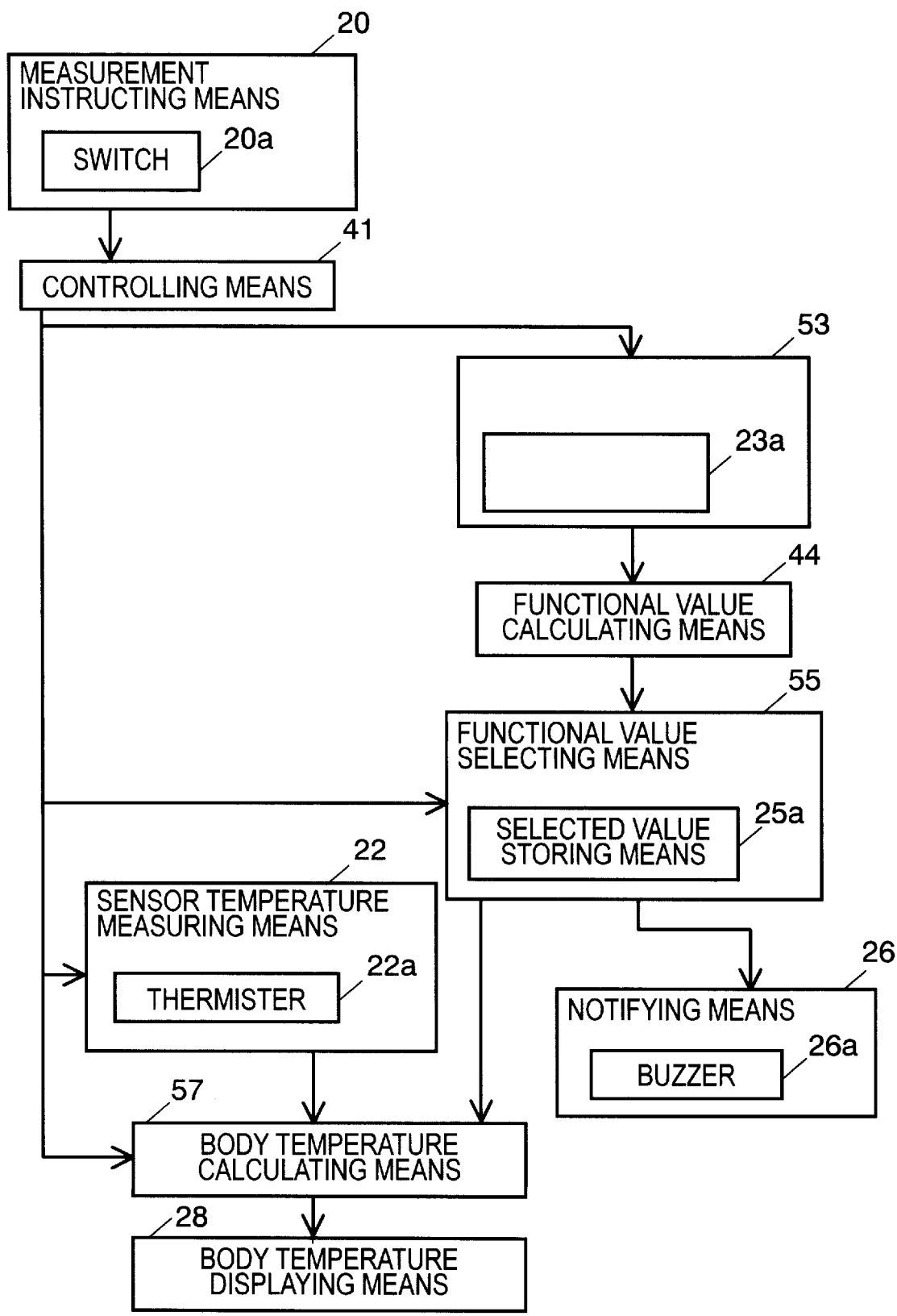
FIG. 9 is a block diagram of an ear type thermometer for women in a sixth exemplary embodiment of the present invention.

FIG. 9 is a block diagram of an ear type thermometer for women in a sixth exemplary embodiment of the present invention. The ear type thermometer for women in the present exemplary embodiment differs from the one in the fifth exemplary embodiment in having an infrared ray measuring means 53, in which the polarity of the output voltage from the infrared sensor 23a is reversed between the positive and negative directions, having a functional value selecting means 55 to select the minimum value out of the functional values derived by calculation from the functional value calculating means 44 in place of the functional value selecting means 25 and having a body temperature calculating means 57 to derive by calculation a body temperature according to a computing formula different from the one used by the body temperature calculating means 47 in place of the body temperature calculating means 47. With regard to other elements that are the same as used in the fifth exemplary embodiment, the same reference numerals are assigned thereto.

Figure 10:
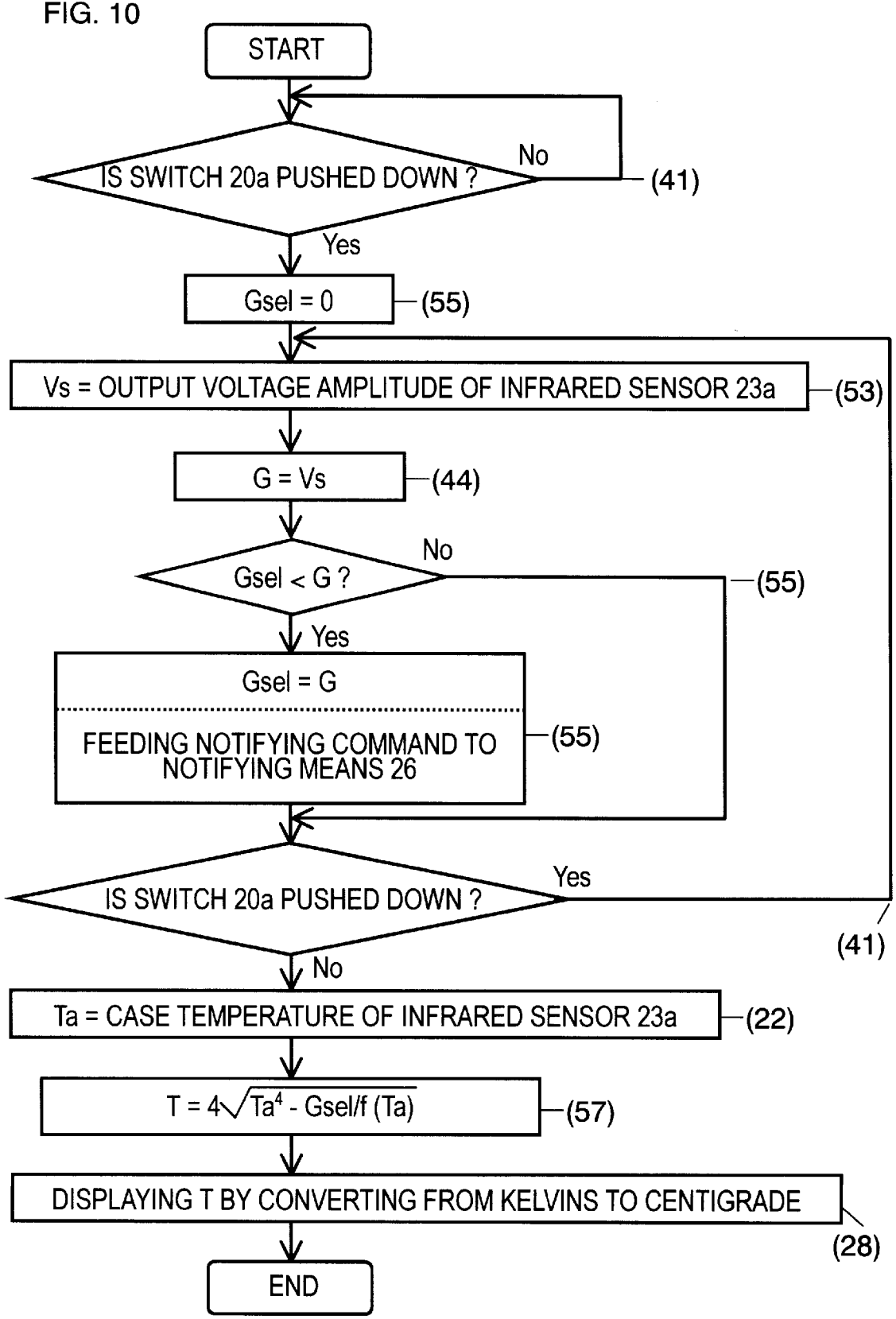
FIG. 10 is a flow chart to show how the ear type thermometer in the sixth exemplary embodiment of the present invention operates.

FIG. 10 is a flow chart to show how the ear type thermometer in the present exemplary embodiment operates. In FIG. 10, the reference numerals of the elements that perform respective operations are indicated in parentheses.

Next, a description is given to how the ear type thermometer for women in the present exemplary embodiment operates and performs with reference to FIG. 10.

The controlling means 41 waits for the switch 20 of the measurement instructing means 20a to be pushed down.

When the switch 20a is pushed down, a controlling signal is generated by the controlling means 41 and the functional value selecting means 55 initializes the value Gsel stored in the selected value storing means 25a to 0.

Subsequent to that, the infrared ray measuring means 53 measures the intensity of infrared rays incident on the infrared sensor 23a to obtain an output voltage Vs, which is then fed to the functional value calculating means 44. An adjustment is made in advance so as to make the value of output voltage Vs negative when the temperature of an area of the eardrum is higher than the case temperature of the infrared sensor 23a and positive when the temperature of the area of the eardrum is lower than the case temperature of the infrared sensor 23a. In other words, a product of the output value of the infrared ray measuring means 23 in the fifth exemplary embodiment times "−1" becomes the output Vs of the infrared ray measuring means 53 in the present exemplary embodiment.

The functional value calculating means 44 furnishes the infrared measurement value Vs from the infrared ray measuring means 53, as is, to the functional value selecting means 55 as a functional value G.

The functional value selecting means 55 makes a comparison between the value Gsel stored in the selected value storing means 25a and the functional value G furnished from the functional value calculating means 44. As a result of the comparison, when the value Gsel is larger than the functional value G, the value Gsel is renewed to the same value as the functional value G and also furnishes the notifying means 26 with a notifying order. When the value Gsel is equal to or smaller than the functional value G, the value Gsel is not renewed and no notifying order is furnished. As a result, the value Gsel ends up storing the minimum value of the functional values G derived by calculation in the functional value calculating means 44. The value Gsel, which the functional value selecting means 55 has stored in the selected value storing means 25a, corresponds to a product of the value, which is made to be stored in the selected value storing means 25a by the functional value selecting means 25 in the fifth exemplary embodiment as described before, times "−1".

Subsequent to that, the status of the switch 20a is checked by the controlling means 41. When the switch 20a is found to be pushed down, a series of processes from an infrared measurement carried out by the infrared ray measuring means 53 to a determination of the status of the switch 20a made by the controlling means 41 are repeated, again. On the other hand, when the switch 20a is not pushed down, the foregoing series of processes are not repeated and the sensor temperature measuring means 22 starts to operate.

The sensor temperature measuring means 22 measures the case temperature of the infrared sensor 23a as the ambient temperature by the use of the thermister 22a and furnishes the temperature expressed in kelvins (K) to gain a value Ta to the body temperature calculating means 57.

Then, the body temperature calculating means 57 derives by calculation a body temperature T expressed in kelvins (K) according to an equation (16) by using the value Gsel stored in the selected value storing means 25a and the ambient temperature Ta furnished from the sensor temperature measuring means 22 as follows:

$$T = \sqrt[4]{T_a^4 - \frac{G_{sel}}{f(T_a)}} \quad (16)$$

where f(Ta) is a polynomial expression, which is the same as used in the fifth exemplary embodiment and is always positive regardless of the value of Ta.

Here, the body temperature T derived by calculation according to an equation (17), which is derived by replacing Gsel in the equation (16) with each respective functional value G used by the functional value selecting means 55 to select the value Gsel, is in a simple increasing relation with the functional value G.

$$T = \sqrt[4]{T_a^4 + \frac{G}{f(T_a)}} \quad (17)$$

Therefore, it is learned to know that the body temperature T derived by calculation according to the equation (16) against the value Gsel, which is the minimum value of the functional value G, is equal to the maximum value of body temperatures derived by calculation individually according to the equation (17) against each respective functional value G.

According to the present exemplary embodiment, since the functional value calculating means 44 uses the infrared measurement value Vs obtained via the infrared ray measuring means 53, as is, to obtain a functional value, the time period spent in deriving by calculation respective functional values is allowed in the same way as in the fifth exemplary embodiment to be further reduced in comparison with the case in the fourth exemplified embodiment.

(Seventh Exemplary Embodiment)

Figure 11:
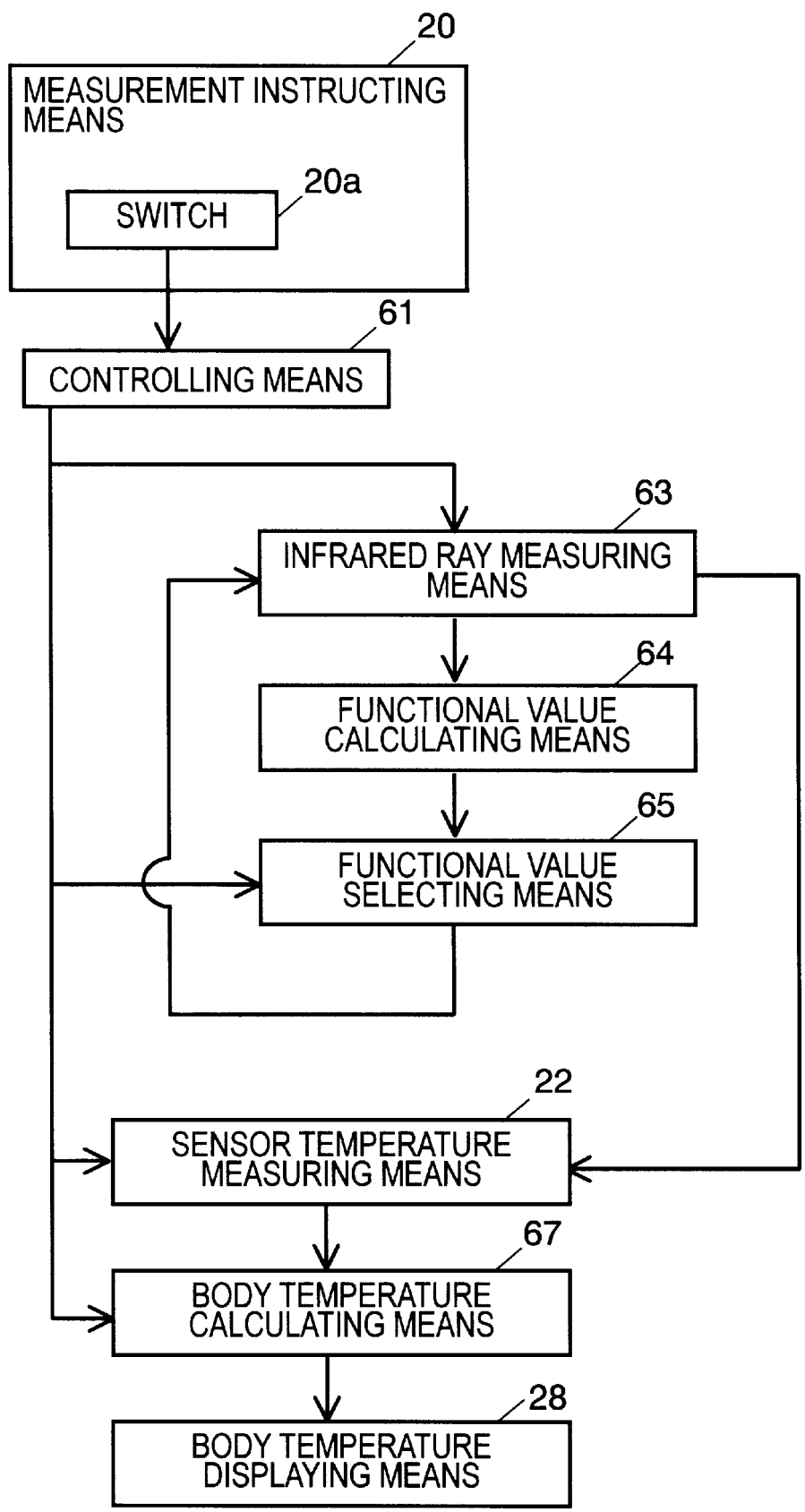
FIG. 11 is a block diagram of an ear type thermometer for women in a seventh exemplary embodiment of the present invention.
Figure 12:
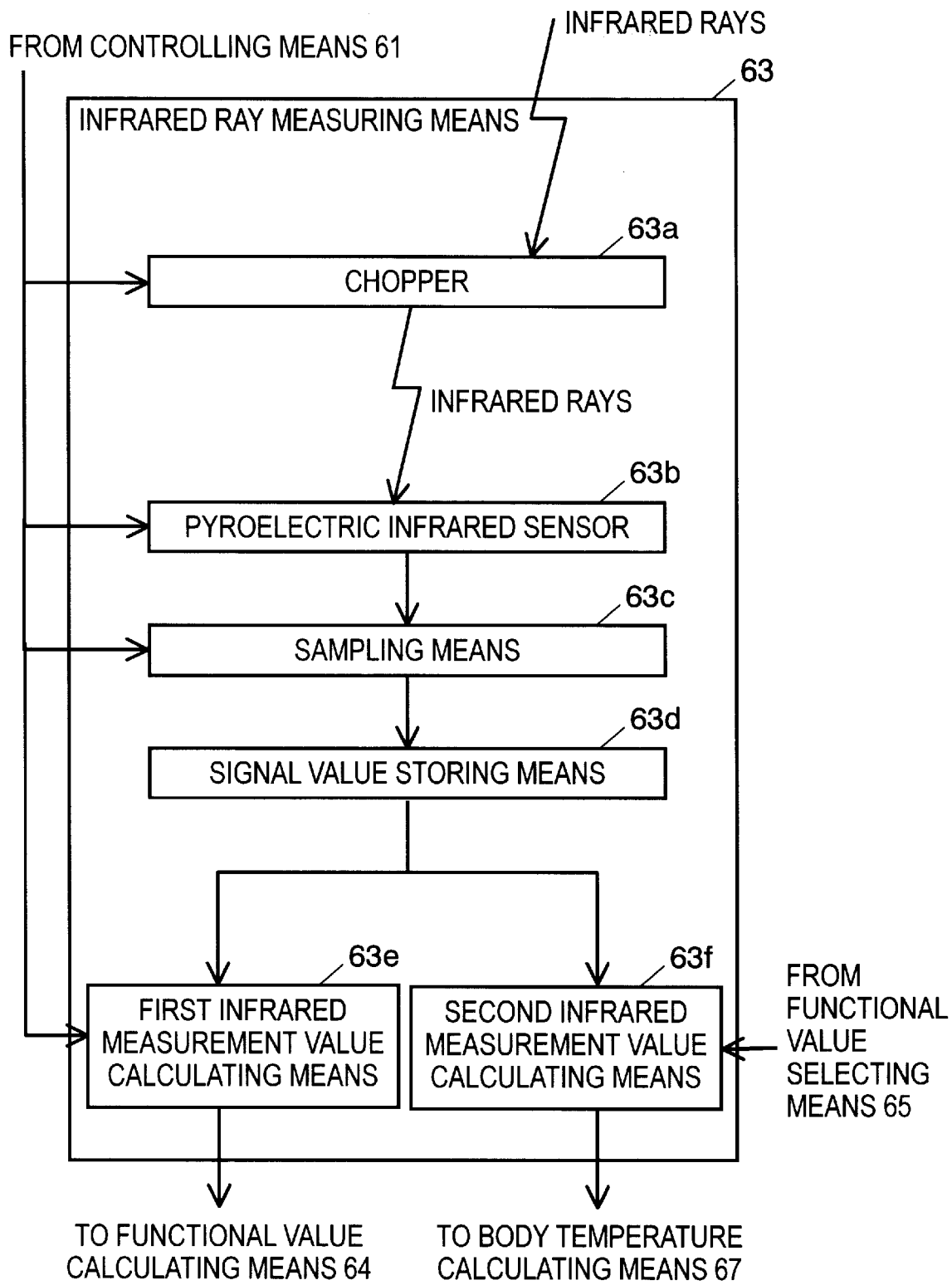
FIG. 12 is a block diagram of an infrared ray measuring means 63 of the ear type thermometer for women in the seventh exemplary embodiment of the present invention.

FIG. 11 is a block diagram of an ear type thermometer for women in a seventh exemplary embodiment of the present invention. In FIG. 11, the reference numeral 61 is a controlling means, 63 is an infrared ray measuring means, 64 is a functional value calculating means and 67 is a body temperature calculating means. With respect to other elements that have the same structure and function as in the fifth exemplary embodiment, the same reference numerals are assigned thereto. FIG. 12 is a block diagram of an infrared ray measuring means 63 of the ear type thermometer for women in the seventh exemplary embodiment of the present invention.

In FIG. 12, the reference symbol 63a is a chopper to interrupts at intervals the infrared rays radiated from an eardrum and 63b is a pyroelectric infrared sensor, which is a kind of thermal infrared sensors to convert the infrared rays interrupted at intervals to an electrical signal. The reference symbol 63c is a sampling means to sample the output signal of the infrared sensor 63b, 63d is a signal value storing means to store a plurality of the signal values sampled by the sampling means 63c, 63e is a first infrared measurement value calculating means to derive by calculation the intensity of infrared rays radiated from an eardrum based on the signal values sampled by the sampling means 63c and 63f is a second infrared measurement value calculating means to derive by calculation the intensity of infrared rays radiated from an eardrum based on the signal values sampled by the sampling means 63c. The second infrared measurement value calculating means is intended for performing calculations that require a longer computation time than the first infrared measurement time calculating means.

Next, a description is given to how the ear type thermometer for women in the present exemplary embodiment operates and performs.

The ear type thermometer for women in the present exemplary embodiment is used only in an environment where the ambient temperature is lower than the body temperatures of an eardrum.

The controlling means 61 waits for the switch 20a of the measurement instructing means 20 to be pushed down.

When the switch 20a is pushed down, a control signal is generated from the controlling means 61 and the chopper 63a of the infrared ray measuring means 63 starts operations of switching at a predetermined period between passing and blocking the infrared rays radiated from an eardrum and incident on the infrared sensor 63b. A description is given here the case where both the passing and blocking time periods are 50 ms, for example. More specifically, the infrared rays radiated from an eardrum are made incident on the infrared sensor 63b for 50 ms and then blocked for 50 ms following thereafter and again made incident for another 50 ms, thus repeating this process on and on. As a result, an alternating voltage signal with a period of 100 ms, which rises during the period of 50 ms when the infrared rays radiated from the eardrum are passed and falls during the period of 50 ms when the infrared rays are blocked, is generated as the output of the infrared sensor 63b.

Subsequent to that, the controlling means 61 waits for a predetermined period until the output voltage signal of the infrared sensor 63b becomes small enough for the influence of the starting up response accompanying the start of operations of the chopper 63a to be allowed to be neglected and an almost stabilized and repetition signal with a period of 100 ms. It is preferable to set this waiting period to about four to five times of the operating period of the chopper 63a. In the case of the present exemplary embodiment, since the operating period of the chopper 63a is 100 ms, the waiting period is set to 500 ms.

After a lapse of the waiting period, the output signal of the infrared sensor 63b becomes an almost stabilized repetition signal with a period of 100 ms but the amplitude of the output signal varies according to the body temperatures of the eardrum, which are covered by the optical field of view of the ear type thermometer for women in question. In other words, the amplitude of the output signal varies in accordance to the intensity of infrared rays radiated from the eardrum and incident on the infrared ray measuring means 63.

After a lapse of the waiting period, the sampling means 63c samples repeatedly the output voltage signal from the infrared sensor 63b at a sampling frequency of 640 Hz that corresponds to 64 times of the repetitive frequency of 10 Hz of the operation of the chopper 63a and sends the sampled signals to the signal value storing means 63d in succession. More specifically, the output signal with a period of 100 ms from the infrared sensor 63b is sampled at a time interval corresponding to one sixty fourth of the foregoing one period and the sampled signal values are fed to the signal value storing means 63d in the order sampled.

The signal value storing means 63d is a memory device to store a plurality of signal values. For the convenience of description the value stored in the ith area of the memory device is expressed as S (i), where i is a natural number such as 1, 2, 3, . . . in the following. The signal value storing means 63d stores the signal, which is fed from the sampling means 63c at the k'th in the ordinal position, as S (K).

On the other hand, the controlling means 61 checks the status of the switch 20a every time when the sampling by the sampling means 63c finishes the 64th sampling, i.e., at every 100 ms of a time interval equaling to the operational period of the chopper 63a, and when the switch 20a is found not to have pushed down, each respective operation of the chopper 63a, sampling means 63c and signal value storing means 63d are brought into suspension. When the switch 20a is found to have been pushed down, each respective operation of the chopper 63a, sampling means 63c and signal value storing means 63d are continued, as is, until the status of the switch 20a is again checked in 100 ms.

Next, a description is given to a case, for example, where the controlling means 61 tries to determine whether each respective operation of the chopper 63a, sampling means 63c and signal value storing means 63d are to be continued or not, and the switch 20a is found to have been pushed down at the first, second, . . . , (N−1)th trials and found not to have been pushed down at the Nth trial. At this time, as many as 64×N signal values are being stored in the signal value storing means 63d.

The first infrared measurement value calculating means 63e and, second infrared measurement value calculating means 63f handle the signal values stored in the signal value storing means 63d by dividing into N groups in total, comprising a first group of S(1) to S(64), a second group of S(65) to S(128), . . . , and an Nth group of S(64×(N−1)+1) to S(64×N), and derives by calculation from a group of signals belonging to each respective group of the foregoing the magnitude of a signal having a frequency component of 10 Hz, which is equal to the operating frequency of the chopper 63a, out of the output signal of the infrared sensor 63b containing various frequency components by utilizing the concept of discrete Fourier transform. A group of 64 signal values, each belonging to respective groups, are a group of signals formed by sampling the output signal of the infrared sensor 63b having a period of 100 ms at a time interval of dividing the one period into 64 equal parts and, therefore, the magnitude of the output signal of the infrared sensor 63b derived by calculation from the signal value belonging to each respective group shows a value representing the intensity of the infrared rays radiated from the eardrum measured by splitting every 100 ms.

After the switch 20a is no longer pushed down and each respective operation of the chopper 63a, sampling means 63c and signal value storing means 63d is suspended, the first infrared measurement value calculating means 63e uses only 16 values picked up every fourth value out of signal values belonging to the nth group stored in the signal value storing means 63d, where the n is an integer corresponding to any number of 1 to N, and derives by calculation a value E(n) proportionate to the energy of a signal component, which has a frequency of 10 Hz equaling to the operating frequency of the chopper 63a, out of the signals with various frequency components contained in the output signal from the infrared sensor 63b when the foregoing signal values are sampled.

The foregoing computation is performed as follows:

First, the following values are derived by calculation according to equations (18) and (19) for an integer n=0, 1, 2, . . . , N−1.

$$V_{\sin}(n) = \sum_{j=1}^{16} \left( S(64 \times n + 4 \times j) \times \sin\left(\frac{2\pi \times 4 \times j}{64}\right) \right) \quad (18)$$

$$V_{\cos}(n) = \sum_{j=1}^{16} \left( S(64 \times n + 4 \times j) \times \cos\left(\frac{2\pi \times 4 \times j}{64}\right) \right) \quad (19)$$

Then, E(n) is allowed to be derived by calculation according to an equation (20).

$$E(n) = V_{sin}(n)^2 + V_{cos}(n)^2 \quad (20)$$

The first infrared measurement value calculating means 63e feeds the E(n) thus derived to the functional value calculating means 64 by bringing the E(n) into correspondence with the integer n.

The functional value calculating means 64 furnishes the value E(n) a fed from the first infrared measurement value calculating means 63e, as is, to the functional value selecting means 65 as a functional value G(n) by bringing the functional value G(n) into correspondence with the integer n.

The functional value selecting means 65 selects the maximum value out of the functional value G(n) furnished from the functional value calculating means 64. For the convenience of description, the integer brought into correspondence with the selected functional value is expressed as m. In other words, the maximum value of G(1), G(2), . . . , G(N) is made as G(m). The functional value selecting means 65 feeds this integer m to the second infrared measurement value calculating means 63f.

Against the integer m fed from the functional value selecting means 65, the second infrared measurement value calculating means 63f derives by calculation a value Vs, which is proportionate to the voltage amplitude of a signal having the same frequency component of 10 Hz equaling to the operating frequency of the chopper 63a, out of the signals with various frequency components that are made to be contained in the output signal of the infrared sensor 63b at the time, when 64 signal values of the mth group out of the groups of signals stored in the signal value storing means 63d are sampled, by using all the 64 signal values belonging to the mth group and furnishes the value Vs to the body temperature calculating means 67.

The aforementioned calculation is carried out as follows: First, values of V2sin and V2cos are derived against the integer m according to equations (21) and (22).

$$V_{2\sin}(n) = \sum_{j=1}^{16} \left( S(64 \times m + j) \times \sin\left(\frac{2\pi \times j}{64}\right) \right) \quad (21)$$

$$V_{2\cos}(n) = \sum_{j=1}^{16} \left( S(64 \times m + j) \times \cos\left(\frac{2\pi \times j}{64}\right) \right) \quad (22)$$

Then, the Vs is allowed to be derived by calculation according to an equation (23).

$$V_s = \sqrt{V_{2\sin}^2 + V_{2\cos}^2} \quad (23)$$

Here, a comparison is made between a square root of the value E(m) derived by calculation from the first infrared measurement value calculating means 63e against the integer m and the value Vs derived by calculation from the second infrared measurement value calculating means 63f. Both values are the values proportionate to the amplitude voltage of the signal component having a frequency of 10 Hz, which is derived by calculation from the signal value obtained by sampling the output signal of the infrared sensor 63b at the same timing. However, since the value derived by a discrete Fourier transform tends to have the influences of noises such as thermal noises and the like contained in each respective sampled value canceled with one another as the number of sampled values is increased, it can be duly expected that the value Vs derived by using all of the 64 sampled values is affected by the noises at a less degree than the value of the square root of E(m) derived by using only 16 sampled values out of the 64 sampled values, thereby ending up gaining a more accurate value. On the other hand, the number of multiplications required of the discrete Fourier transform ends up with a less number required of deriving the E(m) than required of deriving the Vs. More specifically, the value Vs derived by calculation from the second infrared measurement value calculating means 63f shows a higher degree of accuracy but requires a longer computing time period to derive the value and the value E(m) derived by calculation from the first infrared measurement value calculating means 63e shows a little lower degree of accuracy but requires a shorter computing time period to derive the value, thus presenting features different from each other. All in all, the value Vs can be said to have been derived by recalculating the square root of E(m) more accurately. Furthermore, since the functional value G(n) derived by calculation from the functional value calculating means 64 equals to the value E(n) derived by calculation from the first infrared measurement value calculating means 63e, it also can be said that the value Vs is a value obtained by recalculating the square root of the maximum value G(m) of G(n) more accurately.

The sensor temperature measuring means 22 measures the temperature of the case of infrared sensor 63b regarded as an ambient temperature. The measured case temperature expressed in kelvins (K) is referred to as Ta hereafter.

The body temperature calculating means 67 derives by calculation body temperatures expressed in kelvins (K) according to an equation (24) by using the ambient temperature Ta measured by the sensor temperature measuring means 22 and the value Vs furnished from the second infrared measurement value calculating means 63f as follows:

$$T = \sqrt[4]{T_a^4 + \frac{V_s}{f(T_a)}} \quad (24)$$

where f(Ta) is a polynomial expression determined according to the equation (2), the constants A, B and C corresponding to the coefficients in the polynomial expression are determined in advance according to the characteristics of the infrared ray measuring means 63a and f(Ta) is always positive regardless of the value of Ta.

Here, the body temperature T derived by calculation according to an equation (25), which is derived by replacing Vs in the equation (14) with a root square of each respective functional value G(n) used by the functional value selecting means 65 to select the value G(m), is in a simple increasing relation with the functional value G(n).

$$T = \sqrt[4]{T_a^4 + \frac{\sqrt{G(n)}}{f(T_a)}} \quad (25)$$

As mentioned before, the value Vs is a value derived by recalculating a square root of the maximum value G(m) of the values G(n) accurately. Therefore, it is learned to know that the body temperature derived by calculation according to the equation (24) is equal to the maximum value of body temperatures derived by calculation individually according to the equation (25) against each respective functional value G(n).

The body temperature calculating means 67 shows the temperature in Celsius by converting absolute temperature T to a temperature expressed in Celsius. According to the present exemplary embodiment, as a means to derive by calculation a value of infrared rays radiated from an eardrum measured by chopping every 100 ms, both the first infrared measurement value calculating means 63e, whereby a measurement is carried out with a little lower degree of accuracy yet in a shorter computing time period, and the second infrared measurement value calculating means 63f, whereby a measurement is carried out with a higher accuracy, yet taking a longer computing time period, are provided and, when the maximum value of the infrared rays measured by being chopped up every 100 ms is selected, a measurement result of the first infrared measurement value calculating means 63e to finish the computation in a shorter time period is adopted and, thereafter, when a body temperature is derived by calculation, the second infrared measurement value calculating means 63f recalculates the selected maximum value of infrared rays with a higher degree of accuracy based on the signal value read out from the signal value storing means 63d. Therefore, the ultimately derived body temperature can be calculated with excellent accuracy while the time period required to select the maximum value of infrared rays being kept short, thereby enabling an excellent effect to be realized.

In addition, when an infrared measurement is being carried out by pushing down the switch 20a, the output signal of the infrared sensor 63b is stored in the signal value storing means 63d, and upon releasing the pushing down of the switch 20a, the signal value stored in the signal value storing means 63d is read out and a plurality of infrared intensity values measured at intervals of every 100 ms and, therefore, sampling of the output signal of the infrared sensor 63b can be performed continuously without being bothered with the cost involving the time period spent to derive by calculation the intensity of the infrared rays.

Further, since a measurement of the ambient temperature Ta is carried out only once by the sensor temperature measuring means 22, the time period required to derive by calculation each respective functional value can be further shortened by the time period spent on measuring the resistance value of the thermistor 22a via the sensor temperature measuring means 22 and also by the computing time to derive by calculation the ambient temperature based on the resistance value of the thermister 22a according to the equation (4) when compared with the case where the ambient, temperature Ta is measured every time infrared rays are measured as in the third exemplary embodiment.

Although the computing process by the first infrared measurement value calculating means 63e is started after the chopper 63a, sampling means 63c and signal value storing means 63d are suspended in operation in the foregoing description, if at least one value out of the energy values E(n) is derived by calculation via the, first infrared measurement value calculating means 63e during the time period required of the sampling means 63c to perform four times of sampling, the computing process by the first infrared measurement value calculating means 63e can be made to perform in parallel with the operation of the chopper 63a, sampling means 63c and signal value storing means 63d, thereby allowing the first infrared measurement value calculating means 63e to derive an infrared measurement value by calculation on a real-time basis. Accordingly, it becomes unnecessary for the first infrared measurement value calculating means 63e to perform a computing process after the user stopped pushing down the switch 20a, thereby enabling the time period required till body temperatures are displayed on the body temperature displaying means 28 to be further shortened.

It is needless to say that the energy E(n) is derived by calculation with the positive and negative signs reversed in deriving by calculation the intensity of infrared rays via the first infrared measurement value calculating means 63e according to an equation (26) and also a functional value selecting means to select the minimum value out of the functional values G(n) is provided in place of the functional value selecting means 65, thereby allowing the same effect to be achieved.

$$E(n)=-V_{sin}(n)^2-V_{cos}(n)^2 \qquad (26)$$

In the third exemplary embodiment, although the infrared ray measuring means 23 employed the infrared sensor 23a realized by the use of a thermopile as an example, the infrared sensor 23a can be replaced with the infrared sensor 63b realized by a pyroelectric sensor and the chopper 63a as in the seventh exemplary embodiment. In this case, it does not matter whether a peak hold circuit is used in measuring the output voltage amplitude of the infrared sensor 63b, the output signal of which changes like an alternating current, or the first infrared measurement value calculating means 63e is used if the first infrared measurement value calculating means 63e can derive an infrared measurement value by calculation on a real-time basis.

(Eighth Exemplary Embodiment)

Figure 13:
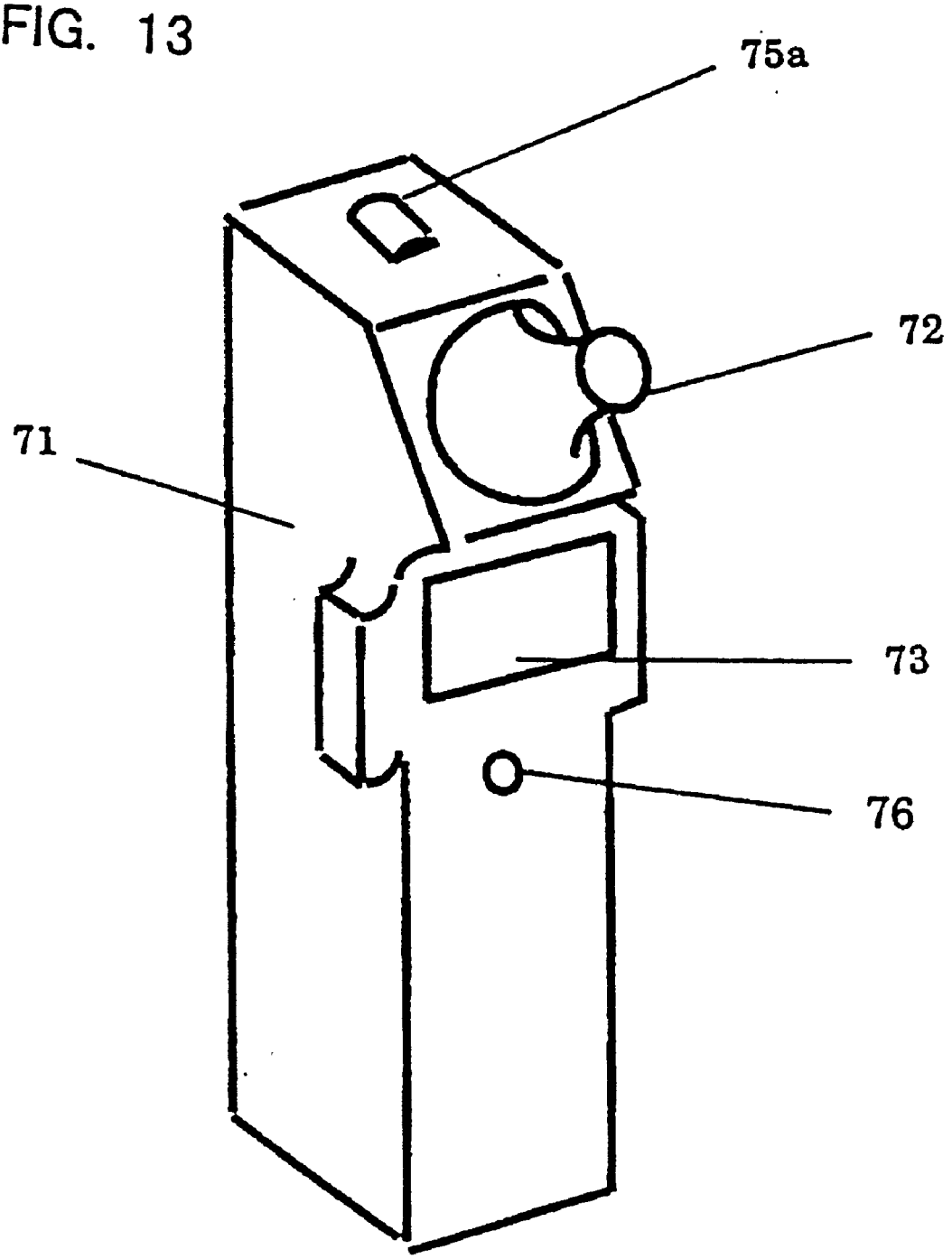
FIG. 13 is a perspective view to show an outward appearance of an ear type thermometer for women in an eighth exemplary embodiment of the present invention.
Figure 14:
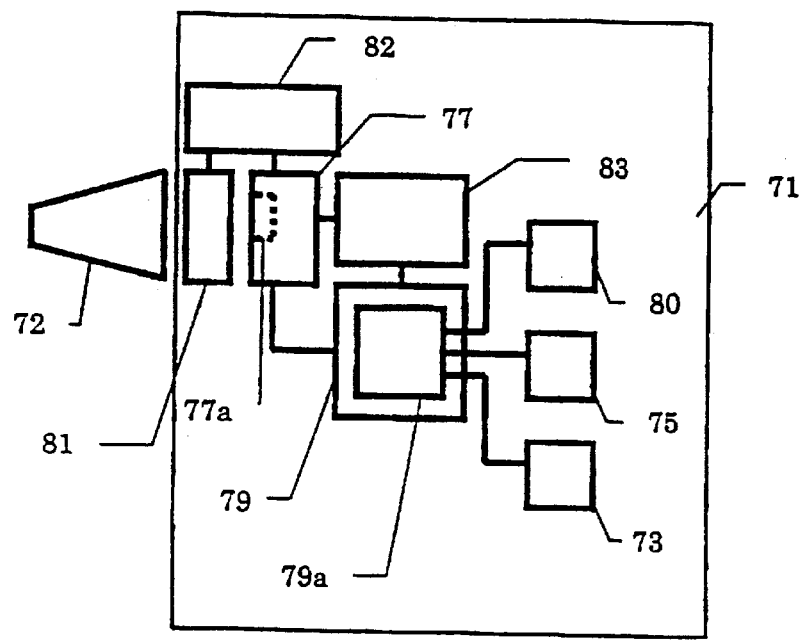
FIG. 14 is a block diagram to show electrical connections of the ear type thermometer for women of FIG. 13.

Next, a description is given to an eighth exemplary embodiment of the present invention. FIG. 13 is a perspective view to show an outward appearance of an ear type thermometer for women in the present exemplary embodiment. The ear type thermometer for women in the present exemplary embodiment comprises a main body 71 of ear type thermometer for women containing a body temperature measuring means and the like and a probe 72 provided as an attachment to the main body 71 of ear type thermometer for women and intended for being inserted in an ear hole. FIG. 14 is a block diagram to show the structure of the body temperature measuring means. The main body 71 of ear type thermometer for women comprises a pyroelectric infrared sensor 77 to receive infrared rays guided via the probe 72, a light-receptive window 77a provided in the pyroelectric infrared sensor 77, a chopper 81 to shield the front surface of the light-receptive window 77a, a chopper driving means 82 to drive the chopper 81 into up-and-down movements, a sensor temperature measuring means 83 to measure the temperature of the pyroelectric infrared sensor 77 and a body temperature calculating means 79 to measure body temperatures upon receiving signals from the pyroelectric infrared sensor 77 and sensor temperature measuring means 83. The body temperature calculating means 79 has a microcomputer 79a and is connected to a buzzer 80, a body temperature displaying means 73, a measurement instructing means 75 and a power switch 76 as FIG. 13 shows.

Figure 15:
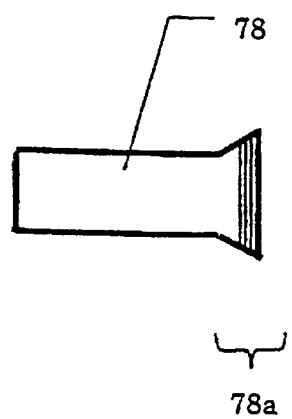
FIG. 15 is a side view to show an outward appearance of an auxiliary probe of the ear type thermometer for women of FIG. 13.
Figure 16:
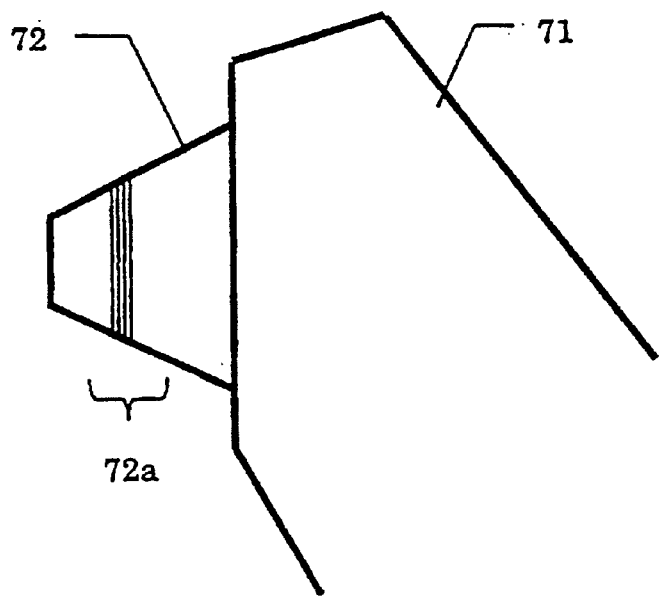
FIG. 16 is a perspective view to show the structure of a probe of the ear type thermometer for women of FIG. 13.
Figure 17:
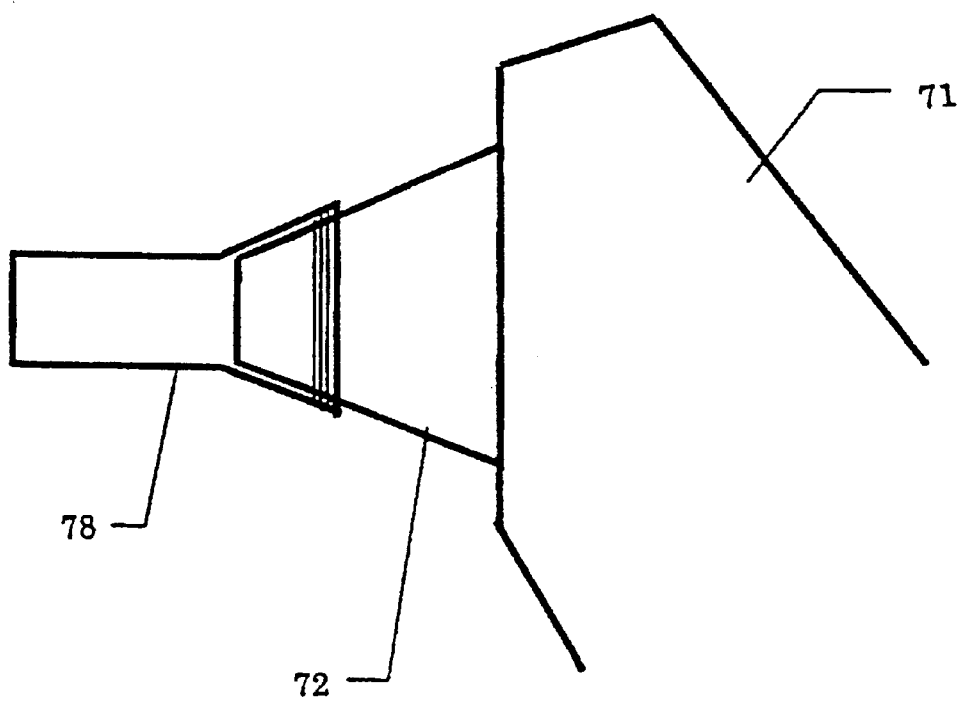
FIG. 17 is a perspective view to illustrate the coupling condition between the probe and the auxiliary probe of the ear type thermometer for women of FIG. 13.

The user of the ear type thermometer for women in the present exemplary embodiment uses the probe 72 covered with an auxiliary probe 78 that FIG. 15 shows. The auxiliary probe 78 is formed by molding such a resin as polypropylene and the like in the present exemplary embodiment but actually there is no specific limitation imposed on the material used. A variety of sizes and configurations are made available for the auxiliary probe 78 to meet the requirements of many people of children and adults. A step-like processed section 78a serving as an auxiliary probe coupling means is provided to an end of the probe 78 as FIG. 15 shows. The step-like processed section 78a fits with another step-like processed section 72a provided to the probe 72 as FIG. 16 shows. When the auxiliary probe 78 is coupled to the probe 72, the step-like processed sections 78a and 72a serve as coupling means to establish a good linkage between both the auxiliary probe 78 and the probe 72. FIG. 17 is a perspective view to illustrate the coupling condition between the probe 72 and the auxiliary probe 78. The user couples the auxiliary probe 78 and the probe 72 together by having the step-like processed section 78a of the auxiliary probe 78 fitted to the step-like processed section 72a of the probe 72.

Next, a description is given to how the ear type thermometer for women in the present exemplary embodiment operates. The user pushes the power switch 76, holds the main body 71 of ear type thermometer for women and inserts probe 72 in an ear hole and then pushes a switch 75a of the measurement instructing means 75, thereby initiating the operation of the ear type thermometer for women in the present exemplary embodiment. More specifically, upon having the switch 75a of the measurement instructing means 75 pushed, a drive pulse signal is generated, thereby driving a motor constituting the chopper driving means 82. The chopper driving means 82 continues operating for a predetermined time period after the switch 75a of the measurement instructing means 75 is pushed. Upon having the chopper driving means 82 been operated, the copper 81 to open and close the light-receptive window 77a of the pyroelectric infrared sensor 77 operates, thereby allowing the infrared rays entering through the light-receptive window 77a to be received by the pyroelectric infrared sensor 77. After receiving the infrared rays, the pyroelectric infrared sensor 77 transmits a temperature signal corresponding to the intensity of the received infrared rays to the body temperature calculating means 79. At this time when the pyroelectric infrared sensor 77 receives the infrared rays radiated from the inner ear, the temperature of the sensor thereof is increased, thereby causing the temperature signal transmitted to the body temperature calculating means 79 to contain an increment of this temperature increase. In order to correct the increment of the temperature increase, the sensor temperature measuring means 83 is adopted. The sensor temperature measuring means 83 measures the temperature of the pyroelectric infrared sensor 77 and transmits the signal of the measured temperature to the body temperature calculating means 79. The microcomputer 79a constituting the body temperature calculating means 79 derives by computing a body temperature based on the signal from the pyroelectric infrared sensor 77 and the signal from the sensor temperature measuring means 83 and has the result of computing displayed on the body temperature displaying means 73. Accordingly, the user can recognize the end of measurement when the buzzer 80 is activated after a lapse of a predetermined time period and learn to know the body temperature by looking at what is displayed on the body temperature displaying means 73.

In the case of the present exemplary embodiment, a time period of 3 seconds is set as the predetermined time period to keep the chopper driving means 82 in driving. Also, a pyroelectric infrared sensor is used as the infrared sensor. Therefore, the light-receptive window 77 a is opened and closed by the chopper 81 and the chopper driving means 82 as described in above. In other words, when other types of infrared sensors than the pyroelectric type are used, it is not necessary for the light-receptive window 77a to be opened and closed. Also, in the case of the present exemplary embodiment, the temperature of the pyroelectric infrared sensor 77 is detected by the sensor temperature measuring means 83 but the sensor temperature measuring means 83 may not needed sometimes when other types of infrared sensors than the pyroelectric infrared sensor are used.

With the ear type thermometer for women in the present exemplary embodiment, when the probe 72 furnished from the beginning together with the thermometer causes the user to feel uncomfortable due to an unfitting size and the like, the auxiliary probe 78 is used. As described before, there are a variety of auxiliary probes 78 prepared with a variety of sizes. When the dimensions of the probe 72 furnished originally measure 15 mm in diameter at the side of coupling with the main body 71 of ear type thermometer for women, 8 mm in diameter at the side of inserting in the ear hole and 25 mm in length, the auxiliary probes 78 prepared in the present exemplary embodiment measure 8 mm in diameter commonly, and 2 mm, 4 mm and 8 mm in length of the extended parts. Therefore, when the user feels uncomfortable with the probe 72 inserted in the ear hole before the measurement is started, a suitable auxiliary probe 78 is allowed to be selected for use. When the selected auxiliary probe 78 and the probe 72 are coupled together, the predetermined dimensions are allowed to be maintained by having the step-like processed section 78a of the auxiliary probe 78 fitted to the step-like processed section 72a of the probe 72.

As a result, the ear type thermometer for women in the present exemplary embodiment allows the user to carry out an accurate measurement of body temperatures by using an auxiliary probe 78 that matches the configuration of the user's ear hole.

(Ninth Exemplary Embodiment)

Figure 18:
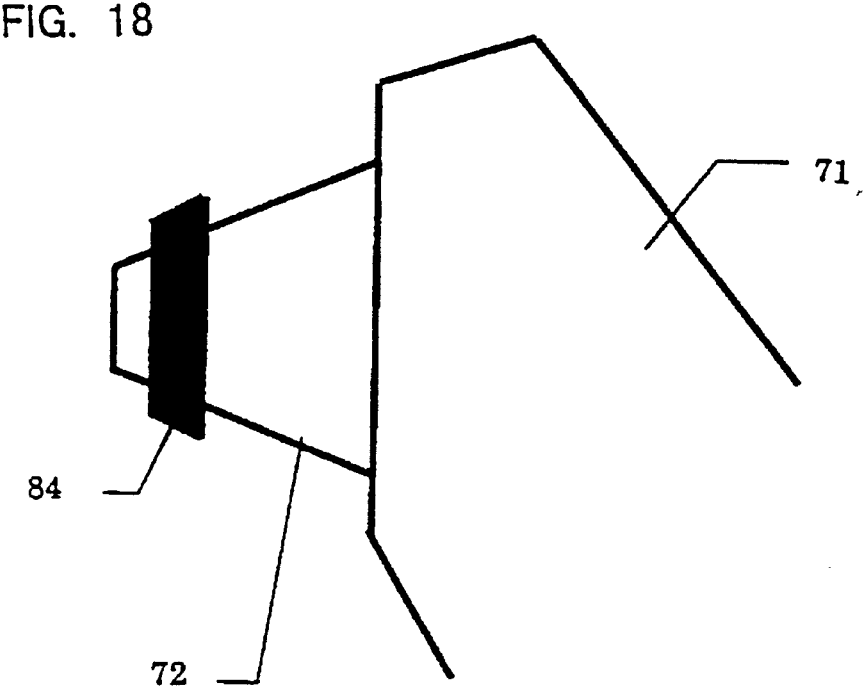
FIG. 18 is a perspective view to show the structure of a probe of an ear type thermometer for women in a ninth exemplary embodiment of the present invention.

Next, a description is given to an ear type thermometer for women in a ninth exemplary embodiment. FIG. 18 is a perspective view to show the structure of a probe of the ear type thermometer for women in the ninth exemplary embodiment of the present invention. According to the present exemplary embodiment, the probe 72 is provided with a ring 84 formed of a friction material such as rubber and the like. In other words, the ring 84 constitutes a coupling means for determining the position of the auxiliary probe 78, thereby further facilitating the coupling of the auxiliary probe 78 as described in the eighth exemplary embodiment. In addition, since the position of the ring 84 is adjustable freely, the auxiliary probes to be prepared can be reduced in the number of kinds when compared with the case in the eighth exemplary embodiment.

Therefore, according to the present exemplary embodiment, the ring 84 serving as a position determining means for the auxiliary probe 78 is attached to the probe 72 furnished with the main body 71 of ear type thermometer for women to allow the fixing position of the auxiliary probe 78 to be kept constant, thereby enabling the realization of an ear type thermometer for women capable of carrying out an accurate measurement of body temperatures.

(Tenth Exemplary Embodiment)

Figure 19:
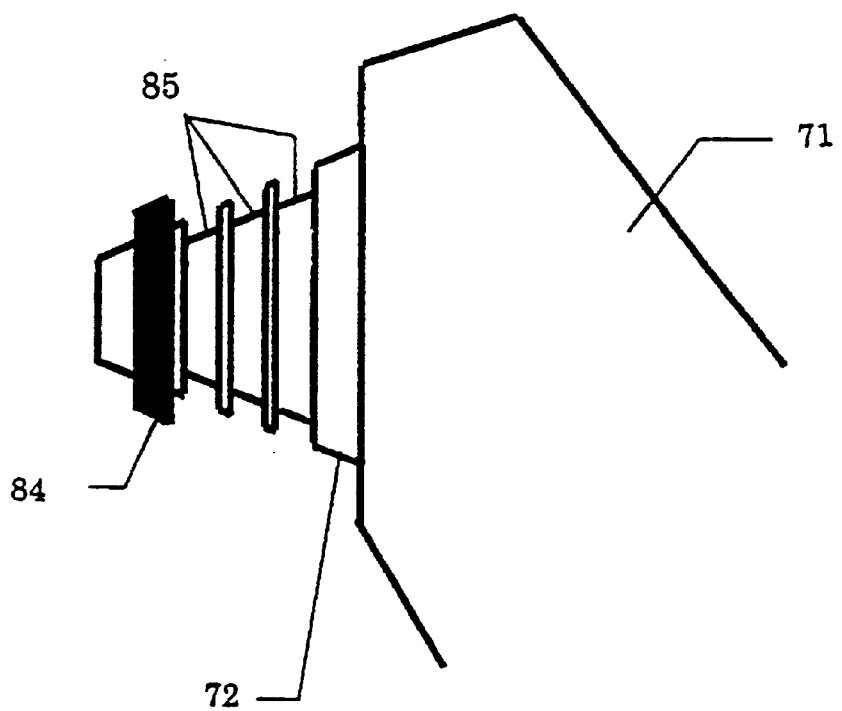
FIG. 19 is a perspective view to show the structure of a probe of an ear type thermometer for women in a tenth exemplary embodiment of the present invention.

Next, a description is made on an ear type thermometer for women in a tenth exemplary embodiment of the present invention. FIG. 19 is a perspective view to show the structure of a probe of the ear type thermometer for women in the present exemplary embodiment. The structure employed in the ninth exemplary embodiment is improved with the present exemplary embodiment by having a plurality of grooves formed on the probe 72. Each respective groove 85 has the ring 84 as described in the ninth exemplary embodiment disposed therein.

In other words, what is described in the ninth exemplary embodiment has a structure liable to have the position of the ring 84 misaligned when the user takes the probe 72 out of the ear hole. In this respect, since the ring 84 is disposed inside of the groove 85 with the present exemplary embodiment, there is no possibility of the misalignment in position of the ring 84.

Accordingly, the ear type thermometer for women in the present exemplary embodiment has a plurality of grooves 85 provided on the probe 72 furnished with the main body 71 of ear type thermometer for women and the ring 84 is disposed in each respective groove 85 for determining the position of the auxiliary probe 78 to keep the fixing position of auxiliary probe 78 constant, thereby allowing the temperature measurement to be carried out accurately.

(Eleventh Exemplary Embodiment)

Figure 20:
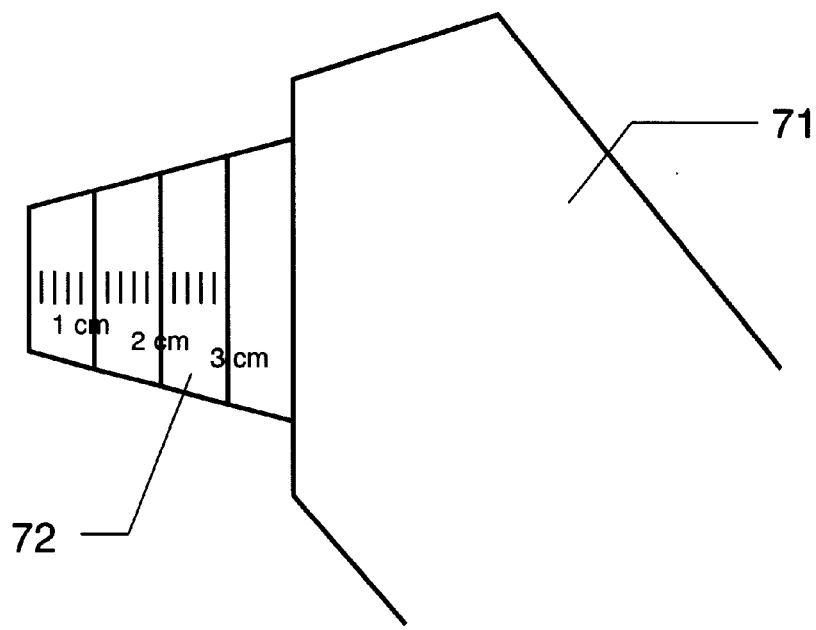
FIG. 20 is a perspective view to show the structure of a probe of an ear type thermometer for women in an eleventh exemplary embodiment of the present invention.
Figure 21:
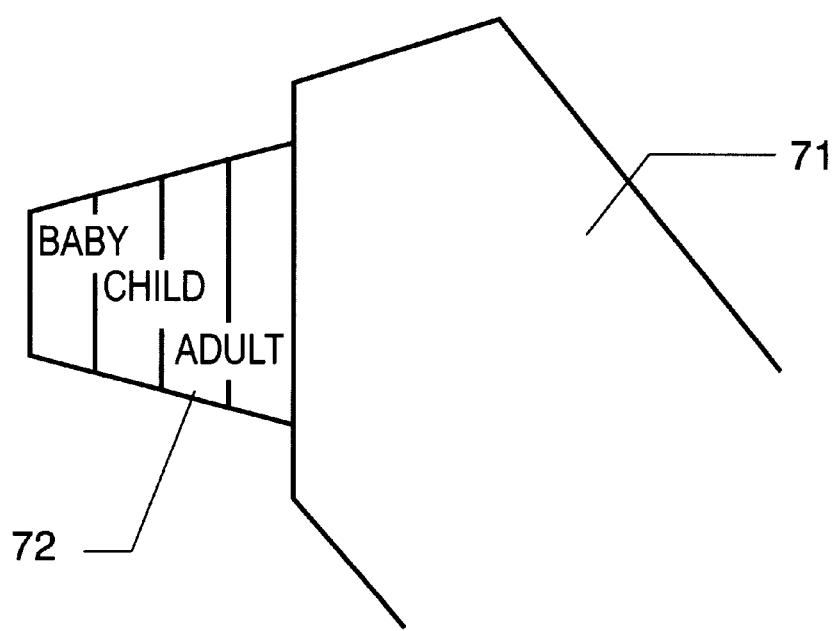
FIG. 21 is a perspective view to show the structure of another probe of the ear type thermometer for women in the eleventh exemplary embodiment of the present invention.

Next a description is given to an ear type thermometer for women in an eleventh exemplary embodiment of the present invention. FIG. 20 is a perspective view to show the structure of a probe of the ear type thermometer for women the present exemplary embodiment and FIG. 21 is a perspective view to show the structure of another probe of the ear type thermometer for women in the present exemplary embodiment. The probe. 72 has scales drawn on the surface thereof in the present exemplary embodiment. As FIG. 20 shows, a scale drawing from 0 mm to 30 mm is applied for every 2 mm on the surface of the probe 72 from the end thereof over the distance of 30 mm. Further, what FIG. 21 carries is markings of "Baby", "Child" and "Adult" instead of the numerical scale markings in FIG. 20.

Accordingly, since the ear type thermometer for women in the present exemplary embodiment has scales drawn on the probe 72, the depth of insertion of the probe 72 in the ear hole is allowed to be controlled from outside, thereby enabling the user to carry out an accurate measurement of body temperatures.

(Twelfth Exemplary Embodiment)

Figure 29:
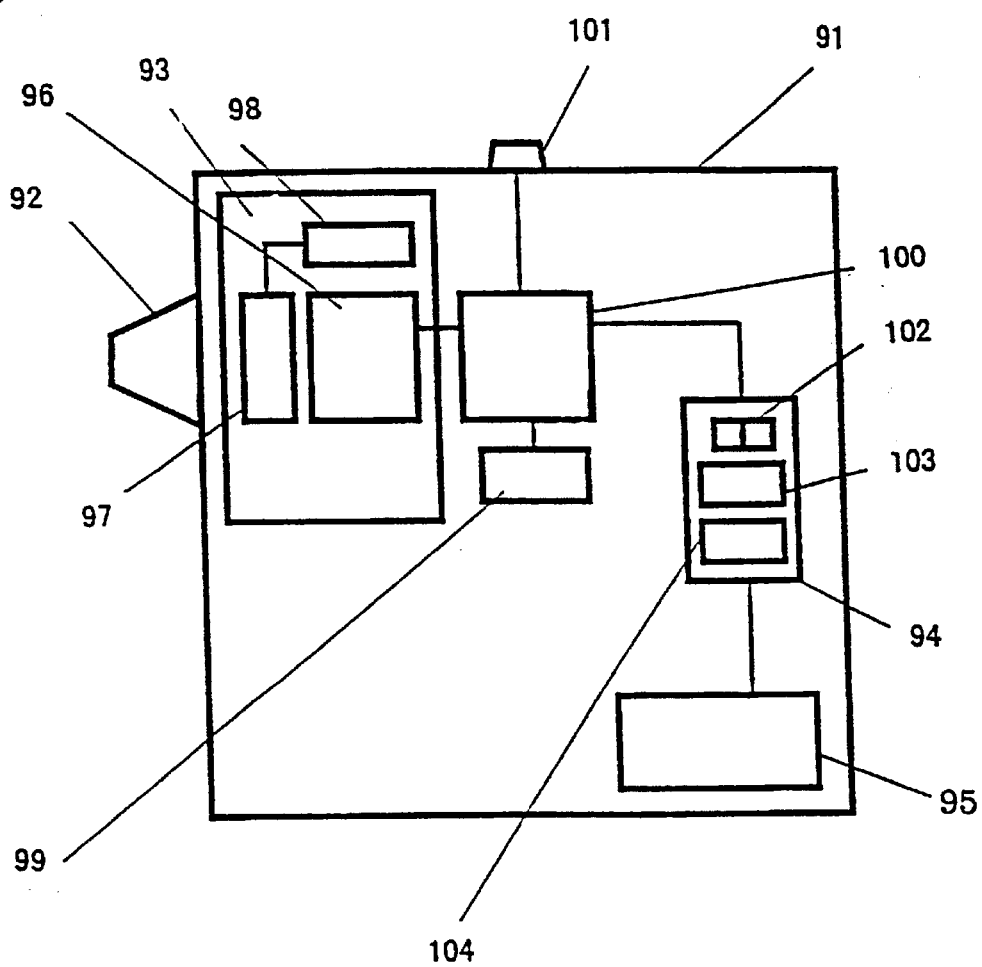
FIG. 29 is a block diagram to show the structure of an ear type thermometer for women in a twelfth exemplary embodiment of the present invention.

Next, a description is given to an ear type thermometer for women in a twelfth exemplary embodiment of the present invention. FIG. 29 is a block diagram to show the structure of the ear type thermometer for women in the present exemplary embodiment and FIG. 30 is a flow chart to show how the ear type thermometer for women in the present exemplary embodiment operates.

First, a description is made on the structure of the ear type thermometer for women in the present exemplary embodiment with reference to FIG. 29. The main body 91 of ear type thermometer for women comprises a probe 92 to guide the infrared rays radiated from a human body upon having the probe 92 inserted in an ear hole to the main body 91 of ear type thermometer for women, an infrared ray measuring means 93 to measure a temperature inside of the ear hole based on the intensity of the infrared rays guided via the probe 92, a probe adaptability determining means 94 and a notifying means 95. The infrared ray measuring means 93 is formed of a pyroelectric infrared sensor 96, a chopper 97 to open and close the light receptive window of the pyroelectric infrared sensor 96, a chopper driving means 98 to drive the chopper 97, a sensor temperature measuring means 99, a body temperature calculating means 100 to perform computations for deriving the temperatures inside of the ear hole based on a signal from the pyroelectric infrared sensor 96 and detected temperatures from the sensor temperature measuring means 99, and a measurement instructing means 101. Since the output signal from the pyroelectric infrared sensor 96 disappears when infrared rays are always incident thereon, the output signal is made available only by repeating periodically the process of blocking and passing the infrared rays by the use of the chopper 97. The probe adaptability determining means 94 Is formed of a mode shifting switch 102, a body temperature comparing means 103, and a body temperature variation determining means 104. The notifying means is formed of a liquid crystal display device and a buzzer sounding unit.

Now, a description is given to how the ear type thermometer for women in the present exemplary embodiment operates with reference to FIG. 29 and FIG. 30. The probe adaptability determining means 94 checks the mode shifting switch 102 to find whether the mode shifting switch 102 is turned to the side of probe selecting mode or not, and when found in the side of probe selecting mode, an action of determining the adaptability of the probe 92 and notifying the result of determination is started. (Step 1) More specifically, the probe adaptability determining means 94 has an identifying number of the probe 92 for the user to attach to the main body 91 of ear type thermometer for women and the number of measurements carried out by the user about the probe 92 displayed on the liquid crystal display device constituting the noting means 95. (Step 2 and Step 3) According to the present exemplary embodiment, a probe number is engraved in advance on each respective probe of the five probes prepared so as to allow the user to identify respective probes and the number of measurements performed is set to 5 times for each respective probe. Then, the probe adaptability determining means 94 measures the body temperature inside of the ear hole and has the measurement value displayed upon having the measurement instructing means 101 pushed.(Step 4 and Step 5) More specifically, when the user inserts the probe 92 in the ear hole and pushes the measurement instructing means 101, the chopper driving means 98 drives the chopper 97, thereby opening and closing the, receptive window of the pyroelectric infrared sensor 96.The infrared rays radiated from the inside of the ear hole and guided by the probe 92 are detected at the pyroelectric infrared sensor 96 by the passing and blocking of the infrared rays performed by the chopper 97.

Since the output signal of the pyroelectric infrared sensor 96 varies according to the temperature of the pyroelectric infrared sensor element itself, the body temperature calculating means 100 computes the temperature inside of the ear hole based on the magnitude of the output of the pyroelectric infrared sensor 96 and the temperature of the pyroelectric infrared sensor element detected by the sensor temperature measuring means 99. When the measurement of the body temperature inside of the ear hole is finished, the chopper driving means 98 stops operating after having the chopper 97 brought into the state of closing, a beep is sounded from the buzzer sounding unit that constitutes the notifying means 95 and the body temperature inside of the ear hole is displayed on the liquid crystal display device. The maximum value retained by peak-holding during the measurement time period is treated as the measurement value at each time when the measurement is carried out.

Next, the probe adaptability determining means 94 repeats the measurement of the body temperature inside of the ear hole until the number of measurement times reaches five for all the five probes, (Step 6 to Step 9) and upon having finished the repeated measurements, an average value of the measurements carried out five times for each respective probe and the value derived by subtracting the minimum value from the maximum value (referred to as a width hereafter) within the measurement values obtained by performing the measurements five times are computed. (Step 10) As a result of the computations, the body temperature comparing means 103 constituting the probe adaptability determining means 94 first makes a comparison among the five time average values with respect to the five probes and selects the probe with the highest value and the body temperature variation determining means 104 constituting the probe adaptability determining means 94 checks the width of the five time measurement values with respect to the probe selected by the body temperature comparing means 103 to find whether the width is within 0.2° C. or not. (Step 11) As a result, if the width of the five time measurement values of the probe that shows the highest average value is found to fall within 0.2° C., then the probe adaptability determining means 94 picks this probe as the most suitable probe and a short and continuous beep is sounded from the buzzer sounding unit that constitutes the notifying means 95 and the probe number is displayed on the liquid crystal display device, followed thereafter with the number of the probe of the highest average value and the remaining numbers of the probes in this order, average values and widths. (Step 12 and Step 13) When there are a plurality of probes that have the highest average values, the probe that has the smallest width of the five time measurement values is treated as the most suitable probe. If the width of the five time measurement values of the probes showing the highest average values is found to exceed 0.2° C., a chopped and yet continuous beep is sounded from the buzzer sounding unit that constitutes the notifying means 95 and the number of the probe of the highest average value and the remaining numbers of the probes in this order, average values and widths are displayed on the liquid crystal display device. (Step 13)

Then, the user attaches the notified probe with the probe number designated as the most suitable to the main body 91 of ear type thermometer for women, switches the mode shifting switch 102 to the normal measurement side and measures the body temperature inside of the ear hole. (Step 15 and Step 16) When the most suitable probe number is not notified, the foregoing process is repeated until the most suitable probe number is notified or the first ranking probe is allowed to be selected based on the information of the notified probe numbers starting from the probe number of the highest average value in sequence, average values and widths. Although the number of the most suitable probe is notified, if the probe does not fit the ear well and a subjective symptom such as an ache and the like shows up, it is recommendable to select a probe that does not cause an ache and ranks high in evaluation based on the information of the notified probe numbers starting from the probe number of the highest average value in sequence, average values and widths.

According to the present exemplified embodiment, five units of probes are prepared and all the probes are checked one after another, but it does not matter whether any numbers of probes are prepared and without checking all the probes the user is allowed to pick up some of the probes. Further, although the number of measurement times is set to five for each respective probe, an arbitrary number for the measurement times is allowed to be selected. Furthermore, although the body temperature comparing means 103 for determining the adaptability of probes is expected to make a comparison of average values five times for each respective probe, the highest value of the five time measurements performed with each respective probe is allowed to be compared with the other highest values. Although the body temperature variation determining means 104 is expected to check the width of the five time measurement values, it does not matter whether the standard deviation of the five time measurements is checked. In addition, when the state of the mode shifting switch 102 is changed, i.e., when the mode shifting switch 102 is switched to the other side, it is allowed to notify the adaptability that was notified already in the beginning or by providing another switch separately and when the switch is pushed it does not matter if the adaptability already notified is to be notified again. Although the methods of notifying are made via the beeping of a buzzer and the displaying on a liquid crystal display device, it does not matter whether the notifying carried out via a voice.

Accordingly, the ear type thermometer for women in the present exemplary embodiment allows the user to select readily the probe that facilitates a correct measurement of eardrum temperatures to be carried out based on the individual differences in the external auditory miatus.

(Thirteenth Exemplary Embodiment)

Figure 31:
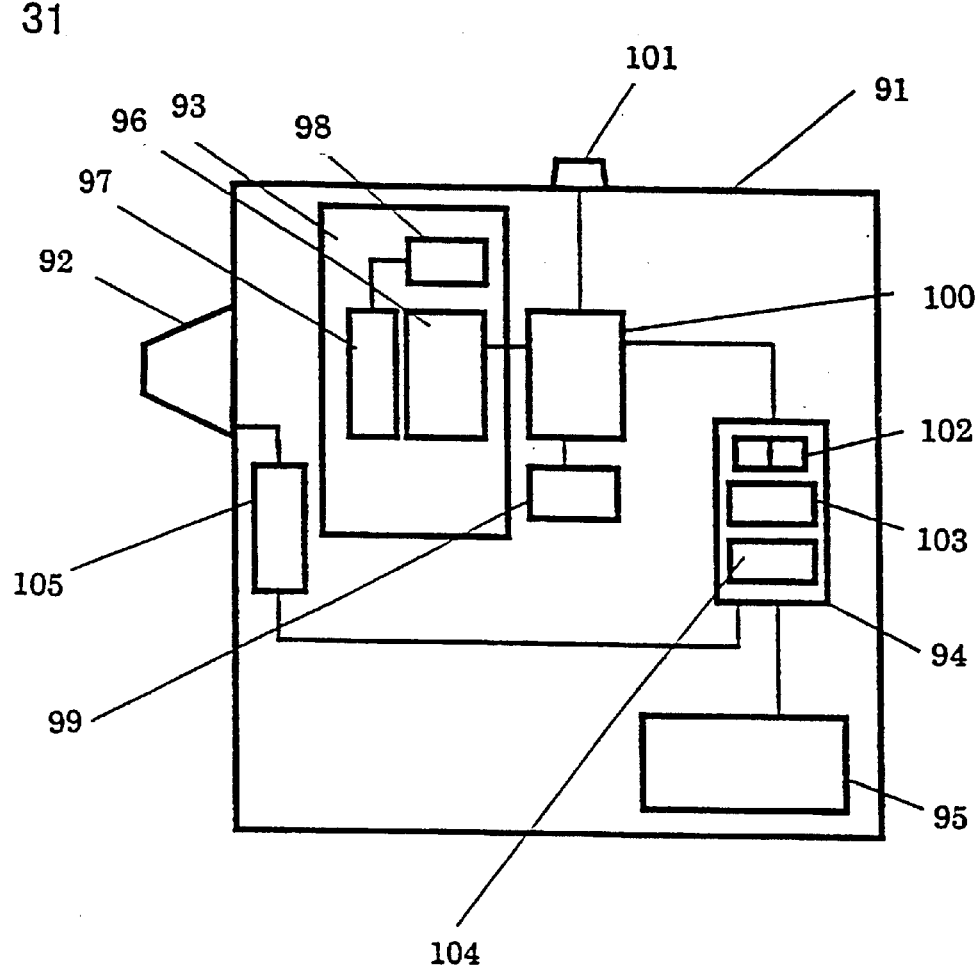
FIG. 31 is a block diagram to show the structure of an ear type thermometer for women in a thirteenth exemplary embodiment of the present invention.

Next, a description is given to an ear type thermometer for women in a thirteenth exemplary embodiment of the present invention. FIG. 31 is a block diagram to show the structure of the ear type thermometer for women in the present exemplary embodiment. The ear type thermometer for women in the present exemplary embodiment further comprises a probe identifying means 105 in addition to the structure of the ear type thermometer for women in the twelfth exemplary embodiment. The probe identifying means 105 identifies a probe automatically based on the position whereby the probe 92 is fitted with the main body 91 of ear type thermometer for women and transmits the information to the probe adaptability determining means 94.

Now, a description is made on how the ear type thermometer for women in the present exemplary embodiment operates. The probe adaptability determining means 94 checks the mode shifting switch 102 to find whether the mode shifting switch 102 is turned to the side of probe selecting mode or not, and when found in the side of probe selecting mode, an action of determining the adaptability of the probe 92 and notifying the result of determination is started. More specifically, the probe adaptability determining means 94 feeds the information of the probe in use furnished from the probe identifying means 105 and displays the identifying number of the probe in use and the number of measurements carried out by using the probe on the liquid crystal display device constituting the notifying means 95. When no probe is found in use, an instruction to the effect that any one of the probes is to be used appears on the display screen of the liquid crystal display device. According to the present exemplary embodiment, a probe number is engraved in advance on each respective probe of the five probes prepared so as to allow the user to identify respective probes and the number of measurements performed is set to 5 times for each respective probe. Then, the probe adaptability determining means 94 measures the body temperature inside of the ear hole and has the measurement value displayed upon having the measurement instructing means 101 pushed. More specifically, when the user inserts the probe 92 in the ear hole and pushes the measurement instructing means 101, the chopper driving means 98 drives the chopper 97, thereby opening and closing the light receptive window of the pyroelectric infrared sensor 96. The infrared rays radiated from the inside of the ear hole and guided by the probe 92 are detected at the pyroelectric infrared sensor 96 by the passing and blocking of the infrared rays performed by the chopper 97. Since the output signal of the pyroelectric infrared sensor 96 varies according to the temperature of the pyroelectric infrared sensor element itself, the body temperature calculating means 100 computes the temperature inside of the ear hole based on the output of the pyroelectric infrared sensor 96 and the temperature of the pyroelectric infrared sensor element detected by the sensor temperature measuring means 99. When the measurement of the body temperature inside of the ear hole is finished, the chopper driving means 98 stops operating after having the chopper 97 brought into the state of closing, a beep is sounded from the buzzer sounding unit that constitutes the notifying means 95 and the body temperature inside of the ear hole is displayed on the liquid crystal display device. The maximum value retained by peak-holding during the measurement time period is treated as the measurement value at each time when the measurement is carried out.

Next, the probe adaptability determining means 94 repeats the measurement of the body temperature inside of the ear hole until the number of measurement times reaches five with respect to the probe and, upon having finished the repeated measurements, another instruction to the effect that a different probe is to be attached is displayed on the liquid crystal display device. When the different probe is attached as instructed, the same operation as performed with the previous probe is carried out. Then, the probe adaptability determining means 94 displays an instruction that another probe is to be attached. When still another probe is no longer attached within a predetermined time period and there are two or more kinds of probes already attached, an average value of the measurement values obtained by carrying out five times in measurement for each respective probe and a width within the five measurements performed, respectively, are derived by computations. As a result of the computations, the body temperature comparing means 103 constituting the probe adaptability determining means 94 first makes a comparison among the five time average values for each respective probe already in use and selects the probe with the highest value and the body temperature variation determining means 104 constituting the probe adaptability determining means 94 checks the width of the five time measurement values with respect to the probe selected by the body temperature comparing means 103 to find whether the width is within 0.2° C. or not. As a result, if the width of the five time measurement values of the probe that shows the highest average value is found to fall within 0.2° C., then the probe adaptability determining means 94 picks this probe as the most suitable probe and a chopped and yet continuous beep is sounded from the buzzer sounding unit that constitutes the notifying means 95 and the probe number is displayed on the liquid crystal display device, followed thereafter with the number of the probe of the highest average value and the remaining numbers of the probes in this order, average values and widths. When there are a plurality of probes that have the highest average values, the probe that has the smallest width of the five time measurement values is treated as the most suitable probe. If the width of the five time measurement values of the probes showing the highest average values is found to exceed 0.2° C., a chopped and yet continuous beep is sounded from the buzzer sounding unit that constitutes the notifying means 95 and the number of the probe of the highest average value and the remaining numbers of the probes in this order, average values and widths are displayed on the liquid crystal display device.

Then, the user attaches the notified probe with the probe number designated as the most suitable to the main body 91 of ear type thermometer for women, switches the mode shifting switch 102 to the normal measurement side and measures the body temperature inside of the ear hole. When the most suitable probe number is not notified, the foregoing process is repeated until the most suitable probe number is notified or the first ranking probe is allowed to be selected based on the information of the notified probe numbers starting from the probe number of the highest average value in sequence, average values and widths. Although the number of the most suitable probe is notified, if the probe does not fit the ear well and a subjective symptom such as an ache and the like shows up, it is recommendable to select a probe that does not cause an ache and ranks high in evaluation based on the information of the notified probe numbers starting from the probe number of the highest average value in sequence, average values and widths.

If another different probe is used after the adaptability of a probe being notified, the adaptability, which is derived from the average values and width of the probe used this time and based on the average values and width of the probe already in use, is notified again.

Although, with the present exemplary embodiment, the timing of notifying the adaptability is set to the time when it is found that still another probe is not used within a predetermined time period and also the number of kinds of the probes already in use counts two or more, the number of kinds of the probes already in use is allowed to be an arbitrary number or the timing is set to the time when the user pushes a switch after having the switch provided. Alternatively, when a measurement of the temperature inside of the ear hole carried out with a probe different from the probes with the most suitable probe numbers notified attached to the main body 91 of ear type thermometer for women and with the mode shifting switch 102 switched to the normal measurement side, it does not matter if an arrangement is made to provide an alarming notification.

Accordingly, the ear type thermometer for women in the present exemplary embodiment allows the user to select the most suitable probe with added easiness.

(Fourteenth Exemplary Embodiment)

Figure 32:
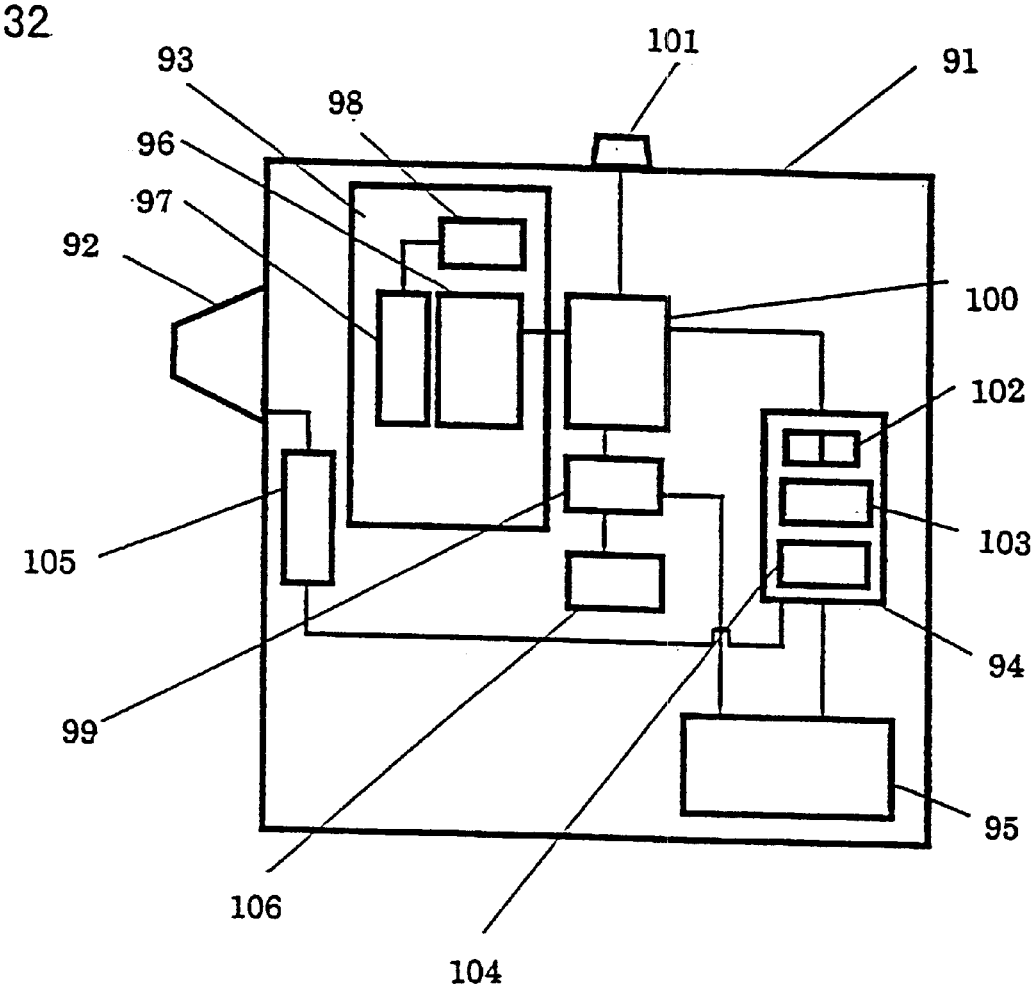
FIG. 32 is a block diagram to show the structure of an ear type thermometer for women in a fourteenth exemplary embodiment of the present invention.

Subsequently, a description is given to an ear type thermometer for women in a fourteenth exemplary embodiment of the present invention. FIG. 32 is a block diagram to show the structure of the ear type thermometer for women in the present exemplary embodiment. The ear type thermometer for women m the present exemplary embodiment further comprises a room temperature storing means 106 in addition to the structure of the ear type thermometer for women in the thirteenth exemplary embodiment. The sensor temperature measuring means 99 detects the temperature of the element itself of the pyroelectric infrared sensor 96 and serves also as a room temperature measuring means by being located at a place with little influence exerted thereon in temperature by the user's hand that holds the sensor temperature measuring means 99 at the time of carrying out a temperature measurement.

Next, a description is made on how the ear type thermometer for women in the present exemplary embodiment operates. The probe adaptability determining means 94 checks the mode shifting switch 102 to find whether the mode shifting switch 102 is turned to the side of probe selecting mode or not, and when found in the side of probe selecting mode, an action of determining the adaptability of the probe and notifying the result of determination is taken as in the thirteenth exemplary embodiment. When the mode shifting switch 102 is turned to the normal measurement side, the room temperature is measured by the use of the sensor temperature measuring means 99. Before the user takes the thermometer for women in a hand to start to use the thermometer for women, the temperature of the thermometer for women is achieving a state of equilibrium with the ambient temperature of the room, thereby allowing the sensor temperature measuring means 99 to measure the room temperature by measuring the temperature of the pyroelectric infrared sensor 96. Only when the present room temperature is lower than the room temperature already stored, the measured room temperature is stored newly in the room temperature storing means 106 and compared with a predetermined value. In the present exemplary embodiment, the predetermined value to compare with is 15° C. When the room temperature is found to have fallen below 15° C. for the first time, the sensor temperature measuring means 99 makes the buzzer sounding unit sound a chopped and yet continuous beep and has a message to urge determining again the probe's adaptability, i.e., an instruction to turn the mode shifting switch 102 to the side of probe selecting mode displayed on the liquid crystal display device. When the, probe adaptability has never been notified, a chopped and yet continuous beep is sounded by the buzzer sounding unit and a message to urge determining again the probe's adaptability is displayed on the liquid crystal display device, provided that the mode shifting switch is turned in the normal measurement side. The user follows this instruction and has the probe's adaptability notified by turning the mode shifting switch 102 to the side of probe selecting mode, thereby using a probe according to the new adaptability determination and carrying out a measurement of the body temperature inside of the ear hole after the mode shifting switch 102 is turned to the normal measurement side.

Although the sensor temperature measuring means 99 is used also as the room temperature measuring means in the present exemplary embodiment, it does not matter whether the room temperature measuring means is provided separately. Also, the sensor temperature measuring means 99 serving as the room temperature measuring means at the same time feeds as an input the room temperature when the mode shifting switch 102 is turned to the normal measurement side, but the feeding as the input is allowed to be notified via the buzzer regardless of the state of the mode shifting switch 102 or the room temperature is allowed to be fed only when a power switch is switched from OFF to ON by providing the power switch separately.

Accordingly, the ear type thermometer for women in the present exemplary embodiment allows the user to select the most suitable probe for a correct measurement of the eardrum temperatures even when the room temperature is low.

(Fifteenth Exemplary Embodiment)

Figure 33:
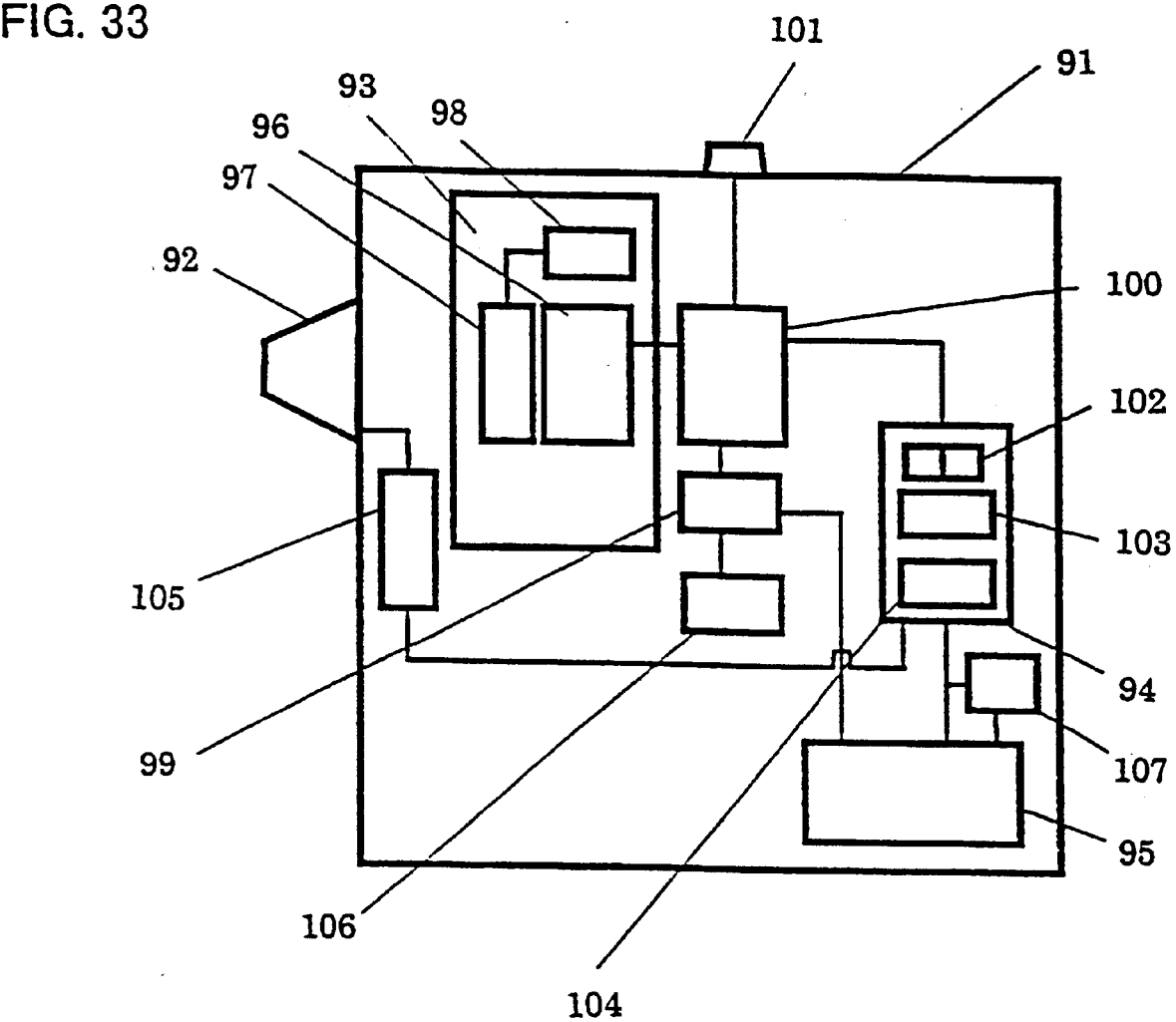
FIG. 33 is, a block diagram to show the structure of an ear type thermometer for women in a fifteenth exemplary embodiment of the present invention.

Subsequently, a description is given to an ear type thermometer for women in a fifteenth exemplary embodiment of the present invention. FIG. 33 is a block diagram to show the structure of the ear type thermometer for women in the present exemplary embodiment. The ear type thermometer for women in the present exemplary embodiment further comprises a clocking means 107 in addition to the structure of the ear type thermometer for women in the fourteenth exemplary embodiment.

Next, a description is made on how the ear type thermometer for women in the present exemplary embodiment operates. The probe adaptability determining means 94 checks the mode shifting switch 102 to find whether the mode shifting switch 102 is turned to the side of probe selecting mode or not, and when found in the side of probe selecting mode, an action of determining the adaptability of the probe and notifying the result of determination is taken as in the thirteenth exemplary embodiment. Here, the clocking means 107 resets the clocking and starts to clock at the time when the notification is provided. At the time when one year has elapsed after the start of clocking, the buzzer sounding unit sounds a chopped and yet continuous beep and a message to urge determining again the probe's adaptability, i.e., an instruction to turn the mode shifting switch 102 to the side of probe selecting mode is displayed on the liquid crystal display device. When the probe adaptability has never been notified, a chopped and yet continuous beep is sounded by the buzzer sounding unit and a message to urge determining again the probe's adaptability is displayed on the liquid crystal display device, provided that the mode shifting switch is turned to the normal measurement side. The user follows this instruction and has the probe's adaptability notified by turning the mode shifting switch 102 to the side of probe selecting mode, thereby using a probe according to the new adaptability determination and carrying out a measurement of the body temperature inside of the ear hole after the mode shifting switch 102 is turned to the normal measurement side.

Although the elapsed time period after providing the notification is made as one year in the present exemplary embodiment, an arbitrary length of time is also allowed to be adopted depending on the extent of aging of the external auditory miatus.

Accordingly, the ear type thermometer for women in the present exemplary embodiment allows the user to select the most suitable probe for a correct measurement of the eardrum temperatures in accordance with the aging of the external auditory miatus.

(Sixteenth Exemplary Embodiment)

Figure 34:
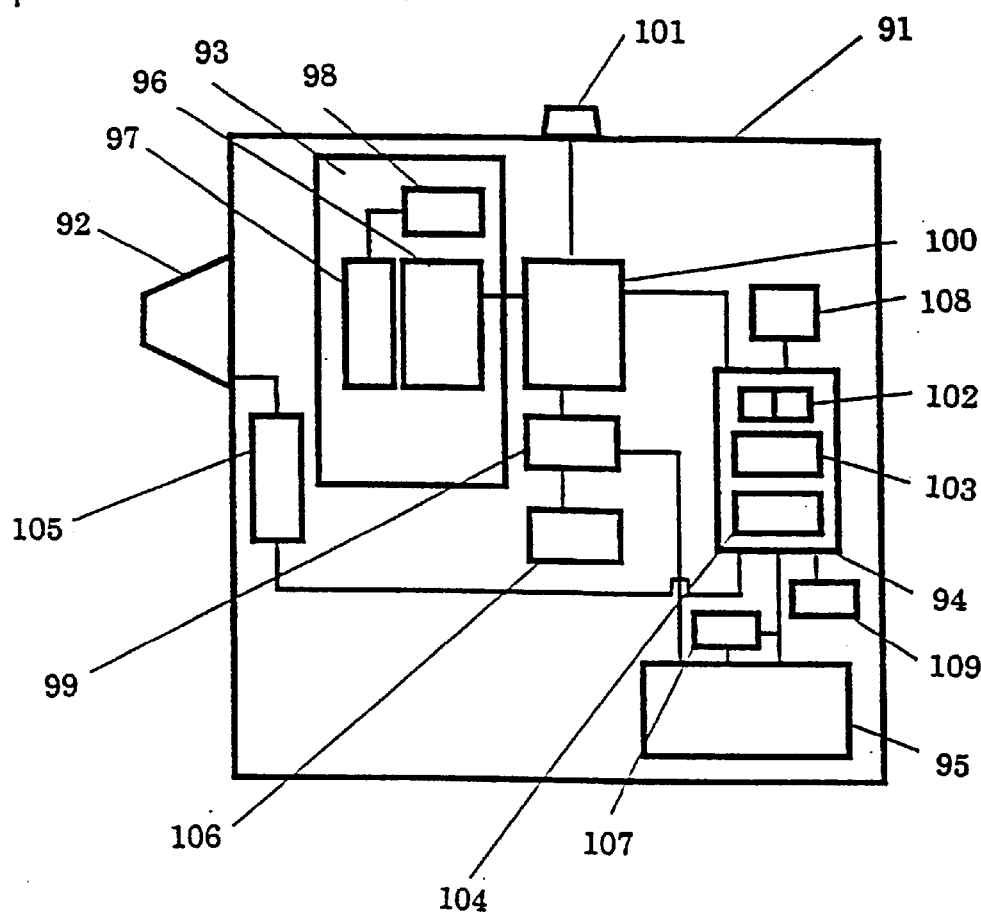
FIG. 34 is a block diagram to show the structure of an ear type thermometer for women in a sixteenth exemplary embodiment of the present invention.

Subsequently, a description is given to an ear type thermometer for women in a sixteenth exemplary embodiment of the present invention. FIG. 34 is a block diagram to show the structure of the ear type thermometer for women in the present exemplary embodiment. The ear type thermometer for women in the present exemplary embodiment further comprises an individuals switching means 108 and an adaptability storing means 109 in addition to the structure of the ear type thermometer for women in the fifteenth exemplary embodiment. In the present exemplary embodiment, the individuals switching means 108 has the capability of selecting five positions of A to E by switching from one to another.

Next, a description is made on how the ear type thermometer for women in the present exemplary embodiment operates. First, the user has the individuals switching means 108 adjusted to her own position. (Position A, for example) The actions of determining probe's adaptability and notifying the result of determination taken by the probe adaptability determining 94 are the same as described in the thirteenth exemplary embodiment. The probe adaptability determining means 94 has the notified message stored in the adaptability storing means 109 according to the position in the individuals switching means 108. In other words, the notified message is stored in the adaptability storing means 109 as the adaptability for the position A.

When the mode shifting switch 102 is switched to the other side or the individuals switching means 108 is switched to other positions, an applicable individual is identified by the state of the individuals switching means at that time and the adaptability of the particular individual stored in the adaptability storing means 109 is notified.

Although the number of switching positions of the individuals switching means 108 is made five of A to E in the present exemplary embodiment, any arbitrary number is also allowed to be adopted.

Accordingly, the ear type thermometer for women in the present exemplary embodiment allows the user to know the adaptability of her own probe by just having the individuals switching means 108 adjusted to her position and select the most suitable probe for a correct measurement of the eardrum temperatures even when the same thermometer is shared by the family of the user.

(Seventeenth Exemplary Embodiment)

Figure 35:
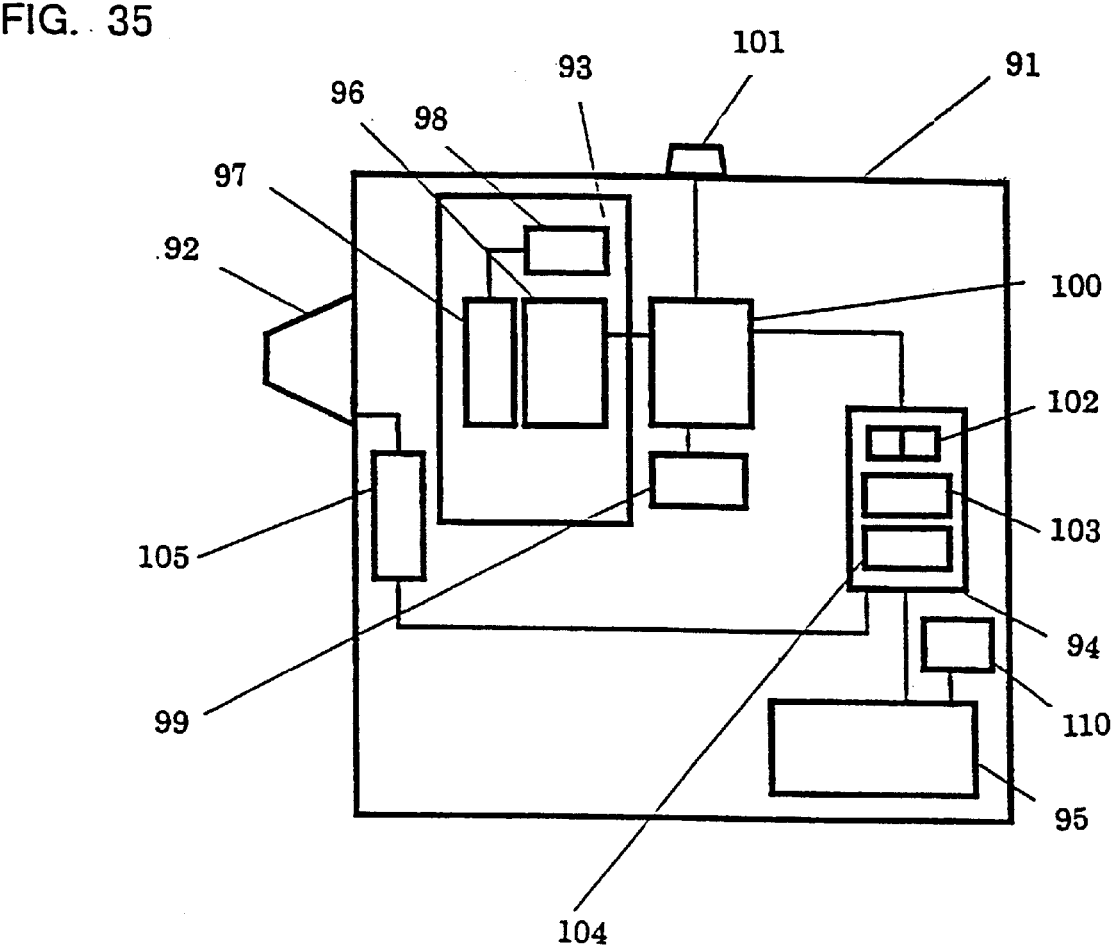
FIG. 35 is a block diagram to show the structure of an ear type thermometer for women in a seventeenth exemplary embodiment of the present invention.

Subsequently, a description is given to an ear type thermometer for women in a seventeenth exemplary embodiment of the present invention. FIG. 35 is a block diagram to show the structure of the ear type thermometer for women in the present exemplary embodiment. The ear type thermometer for women in the present exemplary embodiment further comprises a menstruation start date entering means 110 in addition to the structure of the ear type thermometer for women in the thirteenth exemplary embodiment.

Next, a description is made on how the ear type thermometer for women in the present exemplary embodiment operates. The actions of determining probe's adaptability and notifying the result of determination taken by the probe adaptability determining means 94 are the same as described in the thirteenth exemplary embodiment. The user pushes a switch constituting the menstruation start date entering means 110. When the switch of the menstruation start date entering means 110 is pushed, the probe adaptability determining means 94 has a chopped and yet continuous beep sounded at the buzzer sounding unit and a message to urge determining again the probe's adaptability, i.e., an instruction to turn the mode shifting switch 102 to the side of probe selecting mode displayed on the liquid crystal display device. When the probe adaptability has never been notified, a chopped and yet continuous beep is sounded by the buzzer sounding unit and a message to urge determining again the probe's adaptability is displayed on the liquid crystal display device, provided that the mode shifting switch is turned in the normal measurement side. The user follows this instruction and has the probe's adaptability notified by turning the mode shifting switch 102 to the side of probe selecting mode, thereby using a probe according to the new adaptability determination and carrying out a measurement of the body temperature inside of the ear hole after the mode shifting switch 102 is turned to the normal measurement side.

Thus, with the ear type thermometer for women in the present exemplary embodiment, an influence of the room temperature exerted on a variation of the body temperatures inside of the ear hole is minimal during one menstrual period, thereby allowing the user to select the most suitable probe to carry out a measurement of the basal body temperatures of women correctly and with stability for each respective menstrual period through the use of a probe picked up according to the probe's adaptability notified on every menstruation start date, i.e., on the first day of each respective menstrual period.

(Eighteenth Exemplary Embodiment)

Figure 22:
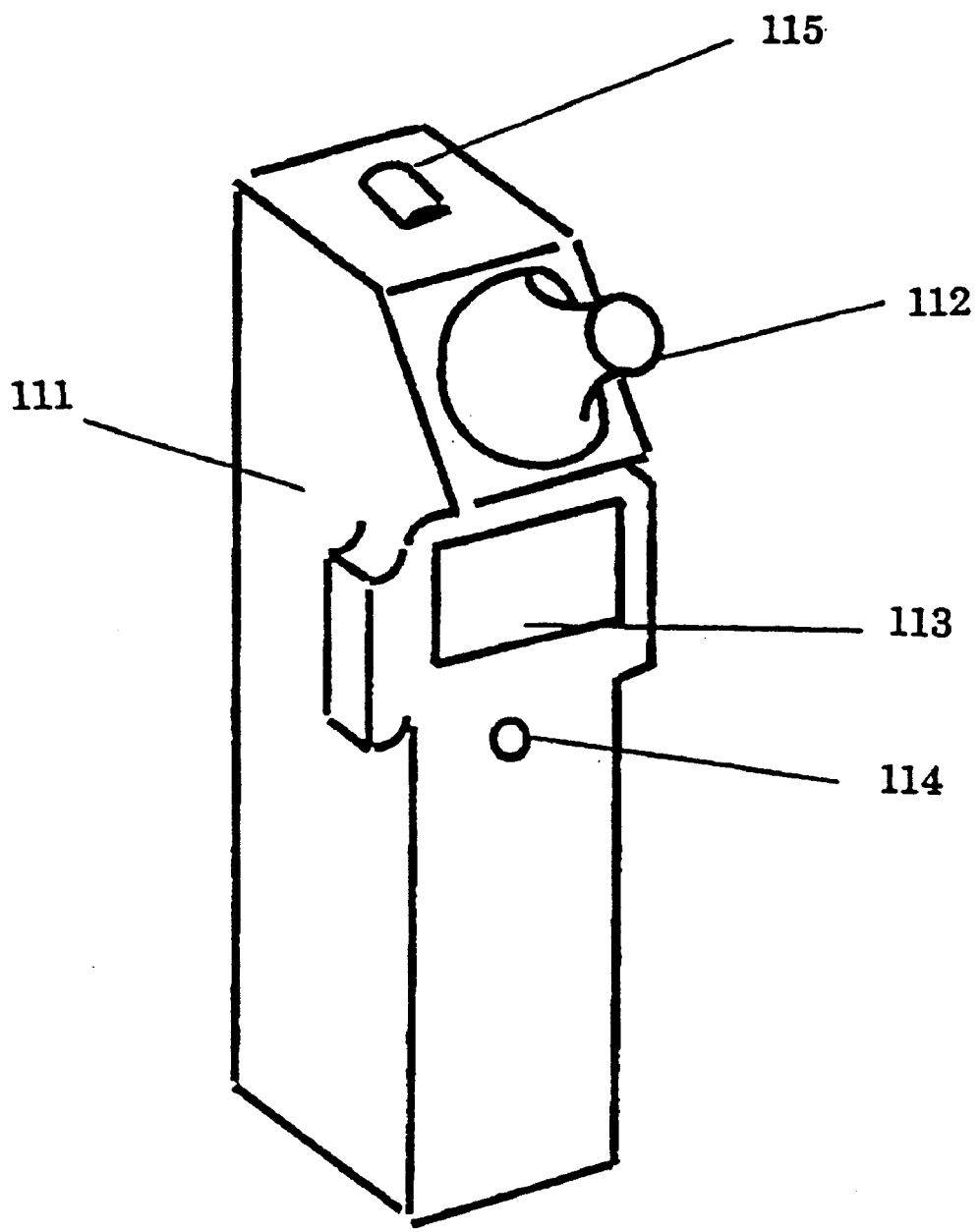
FIG. 22 is a perspective view to show an outward appearance of ear type thermometers for women in eighteenth, nineteenth, twentieth and twenty first exemplary embodiments of the present invention.
Figure 23:
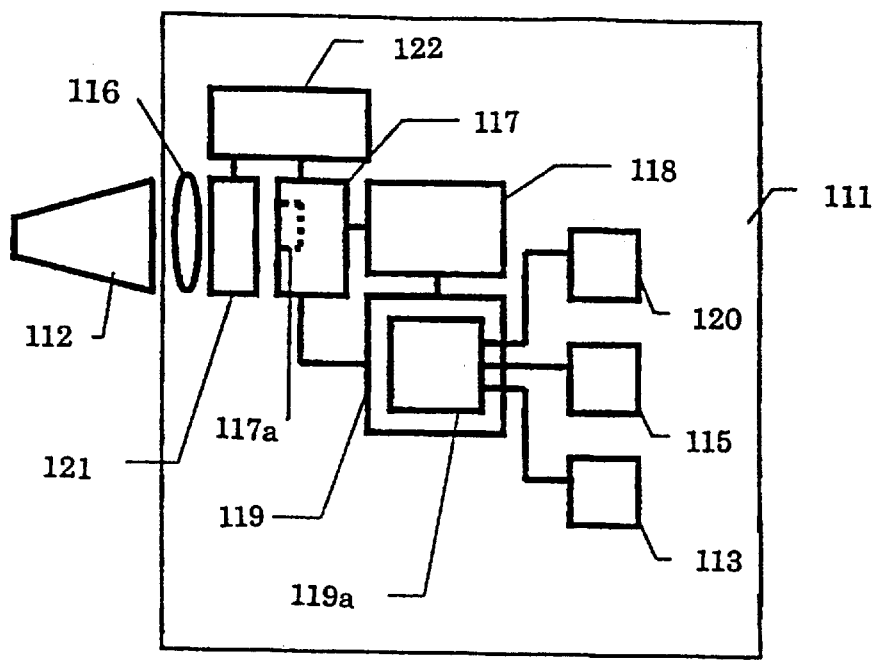
FIG. 23 is a block diagram of a sensor temperature measuring means of the ear type thermometers for women in the eighteenth, nineteenth, twentieth and twenty first exemplary embodiments of the present invention.

Next, a description is given to an ear type thermometer for women in an eighteenth exemplary embodiment of the present invention. FIG. 22 is a perspective view to show an outward appearance of the ear type thermometers for women in the present exemplary embodiment, and FIG. 23 is a block diagram to show the structure of the ear type thermometer for women in the present exemplary embodiment. A main body 111 of ear type thermometer for women has a pyroelectric infrared sensor 117 to detect infrared rays, and a sensor temperature measuring means 118 and a body temperature calculating means 119 to measure body temperatures from an output signal of the pyroelectric infrared sensor 117 provided inside thereof, and a body temperature displaying means 113 to display body temperatures, a probe 112 to be used by inserting in an ear and to guide infrared rays radiated from the human body to the pyroelectric infrared sensor 117, a power switch 114 and a measurement start switch 115 provided on the surface thereof. The main body 111 of ear type thermometer for women has a thin structure for the convenience of portability and the probe 112 is disposed on the upper part thereof.

The main body 111 of ear type thermometer for women comprises a light gathering means 116 focuses the infrared rays guided by the probe 112, the pyroelectric infrared sensor 117 to receive the focused infrared rays,: a light-receptive window 117a provided on the pyroelectric infrared sensor 117, a chopper 121 to block the front surface of the light-receptive window 117a, a chopper driving means 122 to drive the chopper 121 up and down, a sensor temperature measuring means 118 to measure the temperature of the pyroelectric infrared sensor 117 and a body temperature calculating means 119 to derive body temperatures by calculation based on the signals received from the pyroelectric infrared sensor 117 and sensor temperature measuring means 118. The light gathering means 116 is formed of a lens to prevent the probe 112 with a low temperature from entering into the field of view of the pyroelectric infrared sensor 117. The body temperature calculating means 119 comprises a microcomputer 119a, which is connected to a buzzer 120 and the body temperature displaying means 113 and also to the power switch 114 and measurement start switch 115 as FIG. 22 shows.

Figure 24:
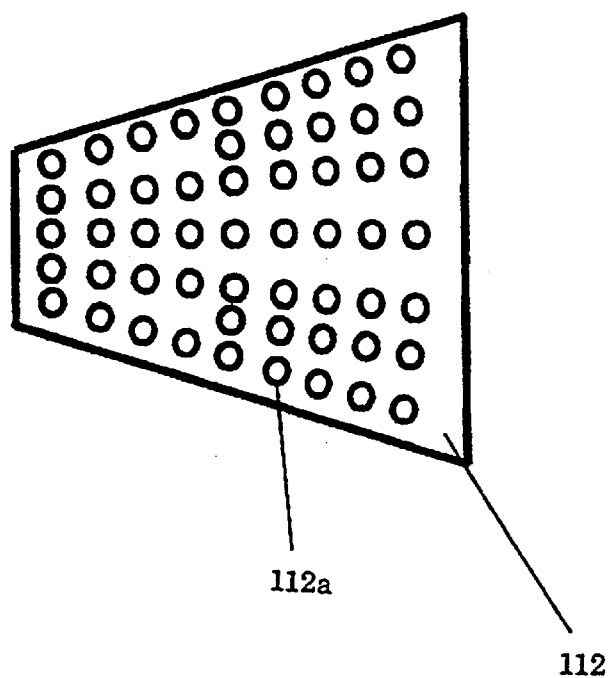
FIG. 24 is a side view to show the configuration of a probe of the ear type thermometer for women in the eighteenth exemplary embodiment of the present invention.

FIG. 24 is a side view to show the structure of the probe 112 used in the ear type thermometer for women in the present exemplary embodiment. The probe 112 in the present exemplary embodiment has many holes 112a disposed thereon.

Next, a description is made on how the ear type thermometer for women in the present exemplary embodiment operates. When the user pushes the power switch 114, holds the main body 111 of ear type thermometer for women, inserts the probe 112 into an ear hole and then pushes the measurement start switch 115, thereby starting the operation of the ear type thermometer for women in the present exemplary embodiment. More specifically, when the measurement start switch 115 is pushed, the body temperature calculating means 119 sends out a driving pulse signal to drive a motor constituting the chopper driving means 122. The chopper driving means 122 continues to operate during a predetermined time period after the measurement start switch is pushed. When the chopper driving means 122 is in operation, the chopper 121 operates, thereby performing the operation of opening and closing the light-receptive window 117a of the pyroelectric infrared sensor 117. Thus, the infrared rays entering through the light-receptive window 117a are incident on the pyroelectric infrared sensor 117. Upon receiving the infrared rays, the pyroelectric infrared sensor 117 transmits a temperature signal corresponding to the intensity of incident infrared rays to the body temperature calculating means 119. Since the temperature of the pyroelectric infrared sensor 117 itself is raised when the infrared rays radiated from the inner ear are incident thereon, the temperature signal transmitted to the body temperature calculating means 119 contains this temperature rise increment. In order to compensate for the temperature rise increment, the sensor temperature measuring means 118 is used. The sensor temperature measuring means 118 measures the temperature of the pyroelectric infrared sensor and transmits the temperature signal obtained to the body temperature calculating means 119. The microcomputer 119a constituting the body temperature calculating means 119 computes body temperatures based on the signals from the pyroelectric infrared sensor 117 and sensor temperature measuring means 118, thereby having the result of computations displayed on the body temperature displaying means 113. After a predetermined time period elapses, the buzzer 120 is activated, thereby allowing the user to learn to know that the measurement is finished and tell the body temperature by looking at the screen of the body temperature displaying means 113.

The predetermined time period, during which the chopper driving means 122 is driven, is set to 3 seconds in the present exemplary embodiment. Also, a pyroelectric infrared sensor is used as the infrared sensor in the present exemplary embodiment. Therefore, the light-receptive window 117a is opened and closed by the chopper 121 and chopper driving means 122 as described before. In other words, when an infrared sensor other than the pyroelectric infrared sensor is used, it is no longer necessary for the light-receptive window 117a to be opened and closed. Although the temperature of the pyroelectric infrared sensor 117 is detected by the sensor temperature measuring means 118 in the present exemplary embodiment, the sensor temperature measuring means 118 may not be needed sometimes provided an infrared sensor other than the pyroelectric type sensor is used.

As the probe 112, a probe with the many holes 112a as FIG. 24 illustrates is used in the present exemplary embodiment, resulting in a reduction of the surface area of the probe 112 that is brought into contact with the external auditory miatus, and the amount of thermal energy transferred from the external auditory miatus to the probe 112 is kept relatively small.

Accordingly, the ear type thermometer for women in the present exemplary embodiment allows the user to carry out an accurate body temperature measurement even under the environment of a low room temperature since the ear type thermometer for women uses the probe 112 creating many holes in the interfacing surface between the probe 112 and the external auditory miatus.

(Nineteenth Exemplary Embodiment)

Figure 25:
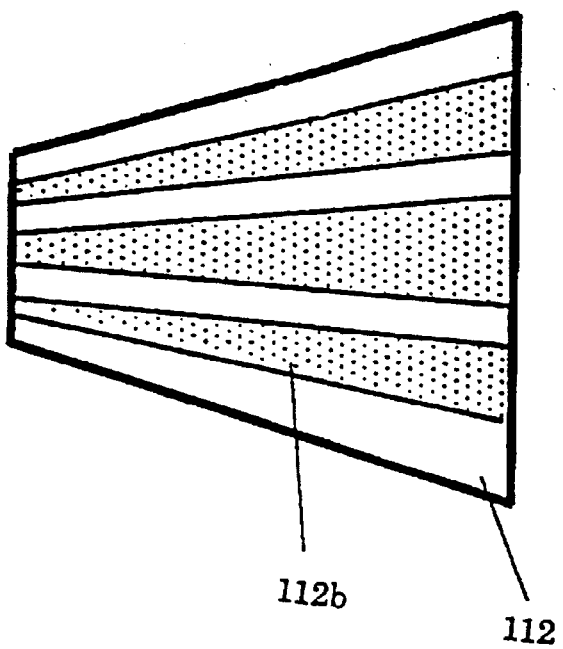
FIG. 25 is a side view to show the configuration of a probe of the ear type thermometer for women in the nineteenth exemplary embodiment of the present invention.
Figure 26:
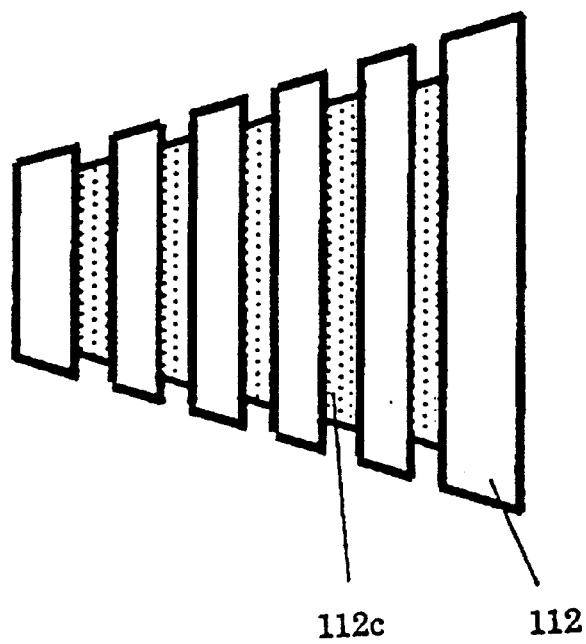
FIG. 26 is a side view to show the configuration of another probe of the ear type thermometer for women in the nineteenth exemplary embodiment of the present invention.

Now, a description is given to an ear type thermometer for women in a nineteenth exemplary embodiment of the present invention. FIG. 25 and FIG. 26 are side views of probes as used together with the ear type thermometer for women in the present exemplary embodiment. In the present exemplary embodiment, the probe 112 is furnished with many grooves on the surface thereof. More specifically, the probe 112 with the structure of FIG. 25 has grooves 112b running lengthwise and the probe with the structure of FIG. 26 has grooves 112c running across. Whichever structure the probe 112 may adopt, the area of the probe 112 that comes into contact with the external auditory miatus is reduced, resulting in a relatively small amount of thermal energy transferred from the external auditory miatus to the probe 112.

Accordingly, the ear type thermometer for women in the present exemplary embodiment allows the user to measure body temperatures accurately even in an environment of a low room temperature by having the probe 112 with many grooves 112b or 112c.

(Twentieth Exemplary Embodiment)

Figure 27:
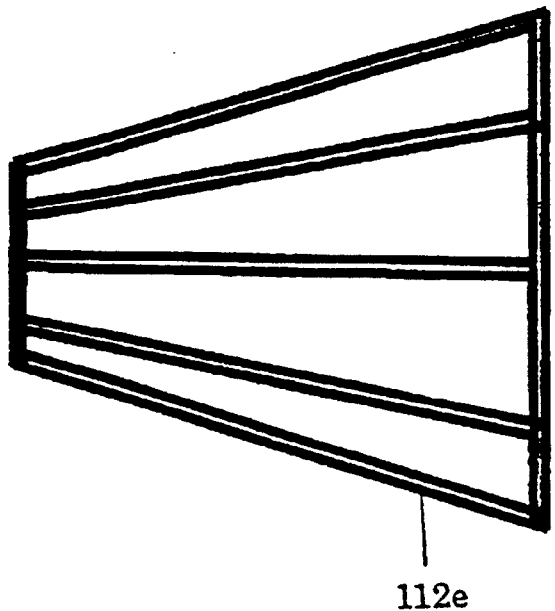
FIG. 27 is a side view to show the configuration of another probe of the ear type thermometer for women in the twentieth exemplary embodiment of the present invention.

Next, a description is given to an ear type thermometer for women in a twentieth exemplary embodiment. FIG. 27 is a side view of the probe 112 as used with the ear type thermometer for women in the present exemplary embodiment. The probe 112 in the present exemplary embodiment is formed of an outer frame 112e.

With the ear type thermometer for women in the present exemplary embodiment, the main body 111 of ear type thermometer for women has a lens as the light gathering means 116 provided therein and the infrared rays radiated from the human body are transferred through the lens to reach the pyroelectric infrared sensor 117 as FIG. 23 shows. At this time, what is inserted in the ear hole is the outer frame 112e and the contact area between the outer frame 112e and the external auditory miatus is made extremely small, thereby allowing the user to measure body temperatures accurately even in an environment of a low room temperature.

(Twenty First Exemplary Embodiment)

Figure 28:
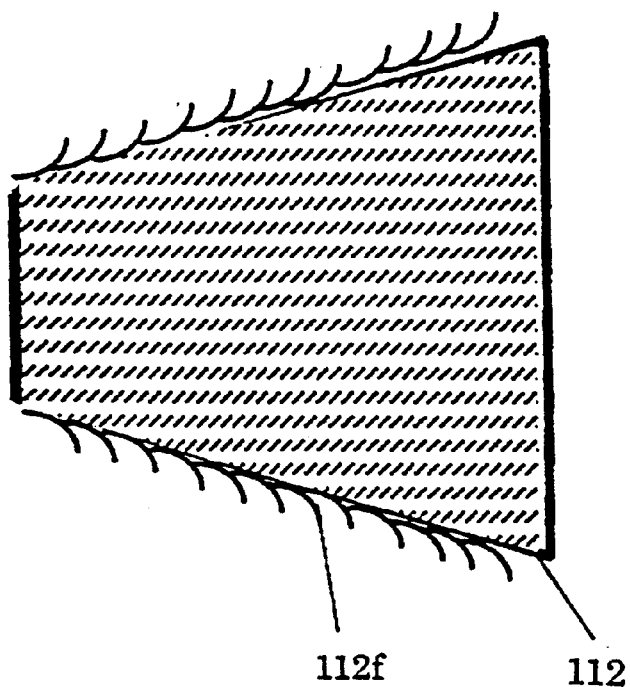
FIG. 28 is a side view to show the configuration of a probe of the ear type thermometer for women in the twenty first exemplary embodiment of the present invention.

Subsequently, a description is given to an ear type thermometer for women in a twenty first exemplary embodiment of the present invention. FIG. 28 is a side view of the probe 112 as used with the ear type thermometer for women in the present exemplary embodiment. The probe 112 in the present exemplary embodiment is provided with a raising material 112f. Although boa or velvet is used as the raising material 112f in the present exemplary embodiment there is no particular restriction required to be imposed on what materials are used.

With the use of the raising material 112f in the probe 112 accordingly, an accurate measurement of body temperatures is allowed to be carried out even in an environment of a low room temperature.

(Twenty Second Exemplary Embodiment)

Figure 36:
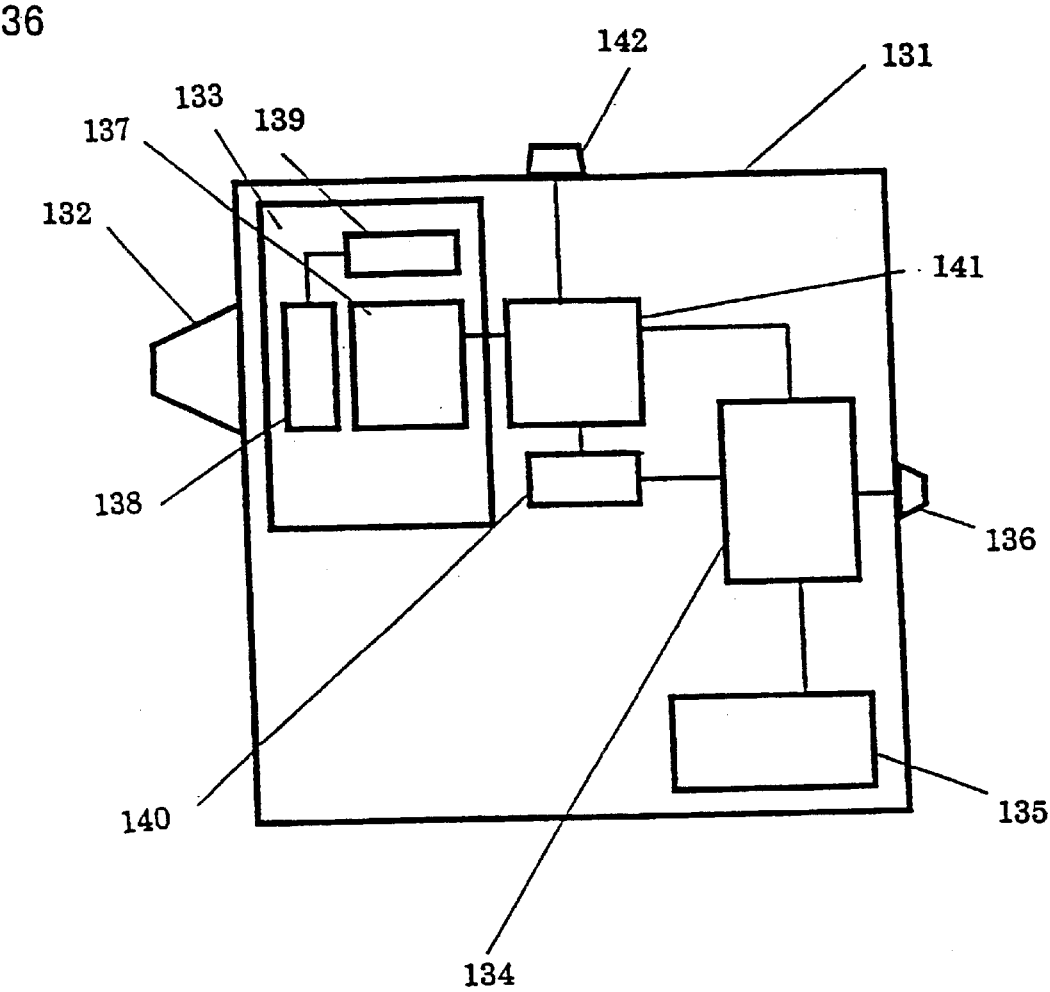
FIG. 36 is a block diagram to show the structure of an ear type thermometer for women in a twenty second exemplary embodiment of the present invention.

Next, a description is given to an ear type thermometer for women in a twenty second exemplary embodiment of the present invention. FIG. 36 is a block diagram to show the structure of the ear type thermometer for women in the present exemplary embodiment. A main body 131 of ear type thermometer for women of the ear type thermometer for women in the present exemplary embodiment (referred to simply as the main body 131 of ear type thermometer for women hereafter) comprises a probe 132 to guide the infrared rays radiated by a human body to the main body 131 of ear type thermometer for women by having the probe 132 inserted in an ear hole, an infrared ray measuring means 133 to measure temperatures inside of the ear hole based on the amount of infrared rays guided by the probe 132, a continuous measurement times determining means 134, a notifying means 135 and a power on/off switch 136. Every time the power on/off switch 136 is pushed, a process of turning on or turning off a power supply to the infrared ray measuring means 133, continuous measurement times determining means 134 and notifying means 135 is repeated. The infrared ray measuring means 133 comprises a pyroelectric infrared sensor 137, a chopper 138 to open or close the light-receptive window of the pyroelectric infrared sensor 137 and a chopper driving means 139 to drive the chopper 138. Further, the main body 131 of ear type thermometer for women comprises a sensor temperature measuring means 140, a body temperature calculating means 141 to compute temperatures inside of the ear hole based on a signal from the pyroelectric infrared sensor 137 and a temperature detected by the sensor temperature measuring means 140 and a measurement instructing means 142. When the pyroelectric infrared sensor 137 remains in the state of always receiving infrared rays, no output signals are generated therein and, therefore, a process of passing or blocking infrared rays needs to be repeated periodically to obtain output signals. The sensor temperature measuring means 140 is intended for measuring the temperature of an element itself of the pyroelectric infrared sensor 137 and also acts as a room temperature measuring means by locating at a place where the influence of the temperature of a user's hand holding the main body 131 of ear type thermometer for women at the time of temperature measurement is hard to be exerted. The continuous measurement times determining means 134 is supplied with information on the status of the power on/off switch 136. The notifying means 135 comprises a liquid crystal display device and a buzzer sounding unit.

Now, a description is made on how the ear type thermometer for women in the present exemplary embodiment operates. When the power of the main body 131 of ear type thermometer for women is turned on by pushing the power on/off switch 136, the continuous measurement times first determining means 134 detects that the status of power is changed from the state of power off to the state of power on when the power on/off switch 136 is pushed. Then, an input signal of the detected temperature is fed to the continuous measurement times determining means 134 from the sensor temperature measuring means 140. Since the sensor temperature measuring means 140 located at a place where the influence of the temperature of a user's hand holding the main body 131 of ear type thermometer for women at the time of temperature measurement is hard to be exerted, the detected temperature is almost the same as the room temperature immediately after the power is turned on. The continuous measurement times determining means 134 treats the detected temperature as the room temperature, determines the number of continuous measurement times based on the room temperature and display the number on the liquid crystal display device constituting the notifying means 135. For example, if the room temperature is 30° C., the number of the measurement times is 1, if the room temperature is 10° C., the number of the measurement times is 3 and the like, thereby displaying on the liquid crystal display device accordingly. The number of continuous measurement times indicates the number, whereby the measurement result for each respective room temperature is not affected by the room temperature after having performed that number of continuous measurement times, and the number is already confirmed through experiments and the like involving many users. In addition, the aforementioned number coincides with the number of continuous measurement times needed in exploring the direction of the eardrum. Upon finding the number on the display screen, the user confirms the number of continuous measurement times to gain sufficient reliability in the measurement values, and then inserts the probe 132 in the ear hole and pushes the measurement instructing means 142. When the measurement instructing means 142 is pushed, the infrared ray measuring means 133 measures the body temperatures inside of the ear hole. More specifically, when the measurement instructing means 142 is pushed, the chopper driving means 139 drives the chopper 138, thereby having the light-receptive window of the pyroelectric infrared sensor 137 opened and closed. The infrared rays, which are radiated from the inside of the ear hole and guided by the probe 132, are chopped by the opening and closing operation of the chopper 138 and detected by the pyroelectric infrared sensor 137. Since the output signal from the pyroelectric infrared sensor 137 fluctuates due to the temperature of the infrared sensor element itself, the body temperature calculating means 141 computes the temperature inside of the ear hole based on the amount of the output signal from the pyroelectric infrared sensor 137 and the temperature of the pyroelectric infrared sensor element detected by the sensor temperature measuring means 140. When the measurement of the body temperature inside of the ear hole is finished, the chopper driving means 139 stops the operation thereof after bringing the chopper 138 to the state of closing, the buzzer sounding unit constituting the notifying means 135 sounds a beep and the liquid crystal display device displays the body temperature inside of the ear hole and also the number of measurement times so far spent in the present measurement. As each respective measurement value of this time is taken the maximum value peak held during the measurement time period.

Similarly, the user pushes the measurement instructing means 142 and repeats the process of measuring body temperatures inside of the ear hole by changing the direction of the probe 132 while exploring the direction of the eardrum until the number of continuous measurement times is reached. When the measurement performed by the number of continuous measurement times is finished, the continuous measurement times determining means 134 has a beep sounded from the buzzer sounding unit. Also, when the measurement performed by the number of continuous measurement times is finished, the user considers the maximum value within the values formed of each respective measurement value as the body temperature inside of the ear hole, brings the measurement to an end and pushes the power on/off switch 136, thereby finishing the whole measurement completely.

According to the present exemplary embodiment, a sensor temperature measuring means also acts as a room temperature measuring means for measuring room temperatures, but it does not matter whether the room temperature measuring means is provided separately. Although the notification of the number of continuous measurement times is made by displaying on the liquid crystal display device, this can be also made by sounding.

Accordingly, the ear type thermometer for women in the present exemplary embodiment allows the user to carry out a body temperature measurement a number of times until reliable repeatability is gained according to room temperatures, thereby preventing the adverse effect under a low room temperature as much as possible and also to change the direction of the probe when the probe is not aligned in the direction of the eardrum.

(Twenty Third Exemplary Embodiment)

Figure 37:
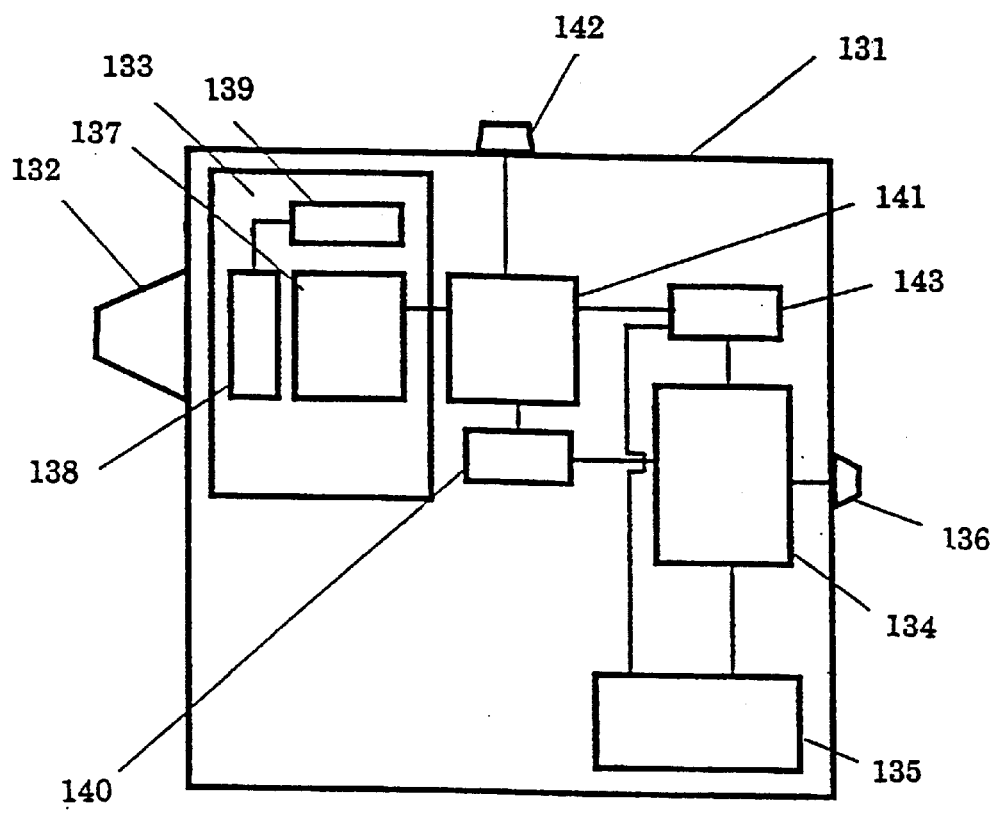
FIG. 37 is a block diagram to show the structure of an ear type thermometer for women in a twenty third exemplary embodiment of the present invention.

Next, a description is given to an ear type thermometer for women in a twenty third exemplary embodiment of the present invention. FIG. 37 is a block diagram to show the structure of the ear type thermometer for women in the present exemplary embodiment. The ear type thermometer for women in the present exemplary embodiment further comprises a storing means 143 in addition to the structure of the ear type thermometer for women, in the twenty second exemplary embodiment.

Now, a description is made on how the ear type thermometer for women in the present exemplary embodiment operates. The user pushes the power on/off switch 136 to turn on the power of the main body 131 of ear type thermometer for women, inserts the probe 132 in the ear hole after having confirmed the display of the number of continuous measurement times determined by the continuous measurement times determining means 134 and finishes one round of the body temperature measurement by pushing the measurement instructing means 142. Up to this step of the operation process, the present exemplary embodiment is the same as the twenty second exemplary embodiment. The storing means 143 stores the measurement values of each respective round of measurement, thereafter, and notifies by displaying on the liquid crystal display device the maximum value during the period of the continuous measurement times at the same time as the measurement value for each respective round of measurement is notified. Similarly, the user repeats the measurement of the body temperatures inside of the ear hole by pushing the measurement instructing means 142 until the number of the continuous measurement times is reached while exploring the direction of the eardrum by changing the direction of the probe 132.

Upon having finished the measurement of the body temperature inside of the ear hole performed the continuous measurement times, the user takes the maximum measurement value gained during the period of the continuous measurement times and displayed on the liquid crystal display device as the body temperature inside of the ear, hole, and brings the process of measurement to an end completely by turning off the power of the main body 131 of ear type themometer for women through pushing the power on/off switch 136.

Further, when the user finishes the measurement by carrying out the notified continuous measurement times or more, the user notifies the maximum measurement value, which is obtained during the period of the measurement times, as the body temperature inside of the ear hole. In other words, when the user carries out the measurement five times against the number of the continuous measurement times notified as three, the user is to notify the maximum measurement value during the period to five times.

According to the present exemplary embodiment, when the power is being turned on, the user is always expected to notify the maximum, measurement value during the period of the continuous measurement times but also allowed to notify by a sound and the like every time when respective measurements are finished.

Accordingly, the ear type thermometer for women in the present exemplary embodiment allows the user to obtain readily a measurement value with enhanced reliability without requiring the user to remember and make a judgment on each respective measurement value during the period of the continuous measurement times.

(Twenty Fourth Exemplary Embodiment)

Figure 38:
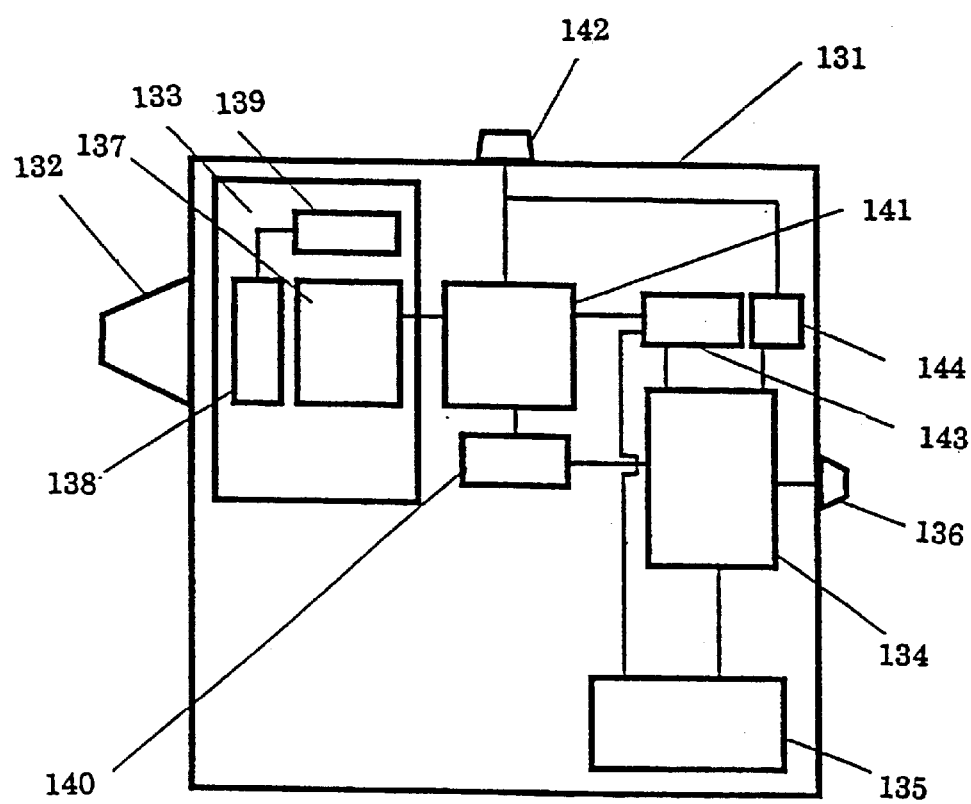
FIG. 38 is a block diagram to show the structure of an ear type thermometer for women in a twenty fourth exemplary embodiment of the present invention.

Subsequently, a description is given to an ear type thermometer for women in a twenty fourth exemplary embodiment of the present invention. FIG. 38 is a block diagram to show the structure of the ear type thermometer for women in the present exemplary embodiment. The ear type thermometer for women in the present exemplary embodiment further comprises a clocking means 144 in addition to the structure of the ear type thermometer for women in the twenty third exemplary embodiment.

Now, a description is made on how the ear type thermometer for women in the present exemplary embodiment operates. The user pushes the power on/off switch 136 to turn on the power of the main body 131 of ear type thermometer for women, inserts the probe 132 in the ear hole after having confirmed the display of the number of continuous measurement times determined by the continuous measurement times determining means 134, finishes one round of the body temperature measurement by pushing the measurement instructing means 142, the measurement value of each respective measurement round is stored in the storing means 143 and the maximum value during the period of the continuous measurement times and also the measurement value of each respective measurement round are notified on the display screen of the liquid crystal display device. Up to this step of the operation process, the present exemplary embodiment is the same as the twenty third exemplary embodiment. The clocking means 144 measures the time interval between respective operations of pushing the measurement instructing means 142. When there is a vacant time period of 10 minutes or more in the time interval measured by the clocking means 144, the continuous measurement times determining means 134 determines again the number of continuous measurement times based on the room temperature at that particular time, i.e., the detected temperature from the sensor temperature measuring means 140 at that time and performs the displaying thereof again on the liquid crystal display device constituting the notifying means 135.

According to the present exemplary embodiment, although the time interval whereby a continuous measurement times determining means gives a notification again is set to 10 minutes or more, the time interval is allowed to be set to an arbitrarily determined time period. Alternatively, the time interval may be changed according to the room temperature.

Accordingly, the ear type thermometer for women in the present exemplary embodiment allows the user to cope with changes in room temperature that may take place during a predetermined time period turned out vacant and created in the time interval between the measurements of body temperatures inside of an ear hole.

(Twenty Fifth Exemplary Embodiment)

Figure 39:
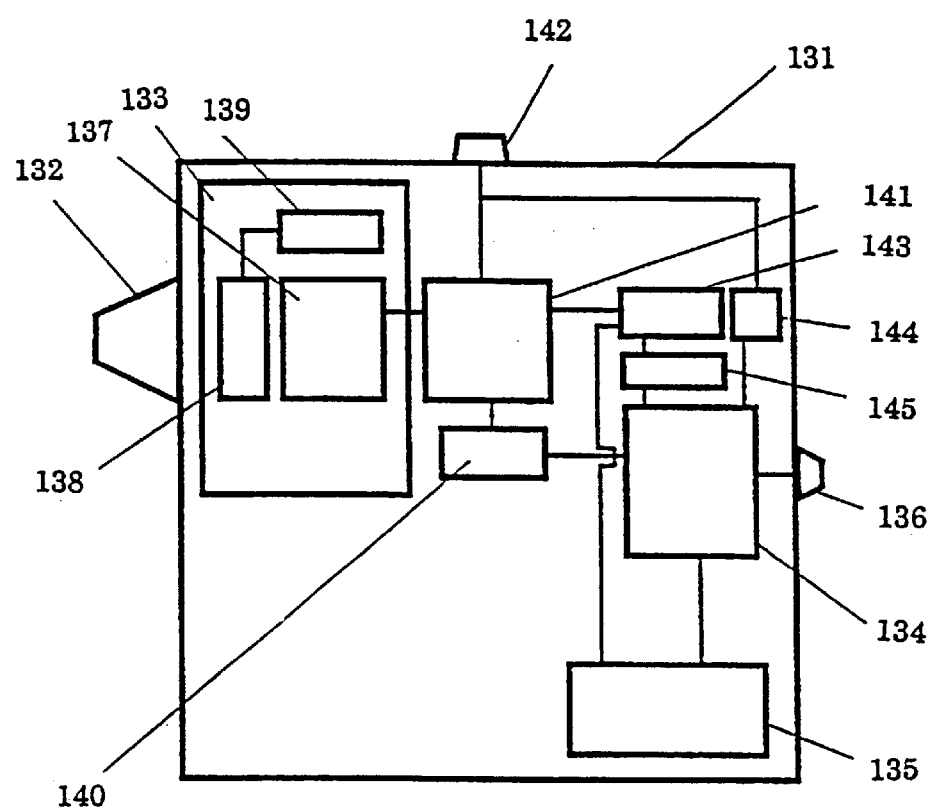
FIG. 39 is a block diagram to show the structure of ear type thermometers for women in twenty fifth, twenty sixth and twenty seventh exemplary embodiments of the present invention.

Subsequently, a description is given to an ear type thermometer for women in a twenty fifth exemplary embodiment of the present invention. FIG. 39 is a block diagram to show the structure of the ear type thermometer for women in the present exemplary embodiment. The ear type thermometer for women m the present exemplary embodiment further comprises a measurement value variation determining means 145 in addition to the structure of the ear type thermometer for women in the twenty fourth exemplary embodiment.

Now, a description is made on how the ear type thermometer for women in the present exemplary embodiment operates. The user pushes the power on/off switch 136 to turn on the power of the main body 131 of ear type thermometer for women, inserts the probe 132 in the ear hole after having confirmed the display of the number of continuous measurement times determined by the continuous measurement times determining means 134 and finishes one round of the body temperature measurement by pushing the measurement instructing means 142. Up to this step of the operation process, the present exemplary embodiment is the same as the twenty fourth exemplary embodiment. The storing means 143 stores the measurement value of each respective round of measurement, thereafter, and notifies by displaying on the liquid crystal display device the maximum value during the period of the continuous measurement times and a variation in measurement values (a value derived by subtracting the minimum value from the maximum value, 0.2° C., for example) for each respective round of measurement at the same time as the measurement value for each respective round of measurement is notified. Similarly, the user repeats the measurement of the body temperatures inside of the ear hole by pushing the measurement instructing means 142 until the number of the continuous measurement times is reached while exploring the direction of the eardrum by changing the direction of the probe 132.

Upon having finished the measurement of the body temperature inside of the ear hole performed the continuous measurement times by the user, the measurement value variation determining means 145 determines whether or not the value obtained by subtracting the minimum value from the maximum value during the period the continuous measurement times is 0.1° C. or lower. When the measurement value variation determining means 145 determines that the variation in measurement values exceeds 0.1° C., the continuous measurement times determining means 134 notifies on the liquid crystal display device to the effect that the number of the continuous measurement times is to be increased by one. Upon having finished the measurement of the body temperature inside of the ear hole performed the continuous measurement times in accordance with the foregoing instruction, the user takes the maximum measurement value gained during the period of the continuous measurement times and displayed on the liquid crystal display device as the body temperature inside of the ear hole and brings the process of measurement to an end completely by turning off the power of the main body 131 of ear type thermometer for women through pushing the power on/off switch 136.

When the user has carried out measurement more than the notified continuous measurement times, the variation of measurement values is determined by comparing with one another the measurement values failing within the notified number of measurement times after having arranged the measurement values in the order of magnitude. More specifically, even if the notified number of continuous measurement times is three, suppose the user has carried out measurements five times. Then, the measurement values obtained during the period of five measurement times are arranged in the order of magnitude and a variation in measurement values is determined from the maximum value and the minimum value picked out of the measurement values falling within the third from the top.

According to the present exemplary embodiment, the measurement variation is determined based on the maximum value and the minimum value taken during the period of continuous measurement times but a standard deviation and the like are allowed to be used instead. It does not matter whether the number of continuous measurement times is increased by the number first notified and whether the increase in the number of continuous measurement times is notified by a voice and the like.

Accordingly, the ear type thermometer for women in the present exemplary embodiment is allowed to enhance the reliability of measurement values thereof.

(Twenty Sixth Exemplary Embodiment)

Subsequently, a description is given to an ear type thermometer for women in a twenty sixth exemplary embodiment of the present invention. The block diagram of FIG. 39 also shows the structure of the ear type thermometer for women in the present exemplary embodiment as in the twenty fifth exemplary embodiment.

Next, a description is made on how the ear type thermometer for women in the present exemplary embodiment operates. The user pushes the power on/off switch 136 to turn on the power of the main body 131 of ear type thermometer for women, inserts the probe 132 in the ear hole after having confirmed the display of the number of continuous measurement times determined by the continuous measurement times determining means 134 and finishes one round of the body temperature measurement by pushing the measurement instructing means 142. Up to this step of the operation process, the present exemplary embodiment is the same as the twenty fifth exemplary embodiment. The storing means 143 stores the measurement value of each respective round of measurement, thereafter, and notifies by displaying on the liquid crystal display device the maximum value during the period of the continuous measurement times and a variation in measurement values (a value derived by subtracting the minimum value from the maximum value, 0.1° C., for example) for each respective round of measurement at the same time as the measurement value for each respective round of measurement is notified. Further, the remaining number of continuous measurement times is displayed at the same time. Similarly, the user repeats the measurement of the body temperatures inside of the ear hole by pushing the measurement instructing means 142 until the remaining number of the continuous measurement times becomes zero while exploring the direction of the eardrum by changing the direction of the probe 132.

Upon being notified that the remaining number of continuous measurement times has reached zero, the user takes the maximum measurement value gained during the period of the continuous measurement times and displayed on the liquid crystal display device as the body temperature inside of the ear hole and brings the process of measurement to an end completely by turning off the power of the main body 131 of ear type thermometer for women through pushing the power on/off switch 136.

Accordingly, the ear type thermometer for women in the present exemplary embodiment allows the user to create awareness about obtaining measurement values with enhanced reliability.

(Twenty Seventh Exemplary Embodiment)

Figure 40:
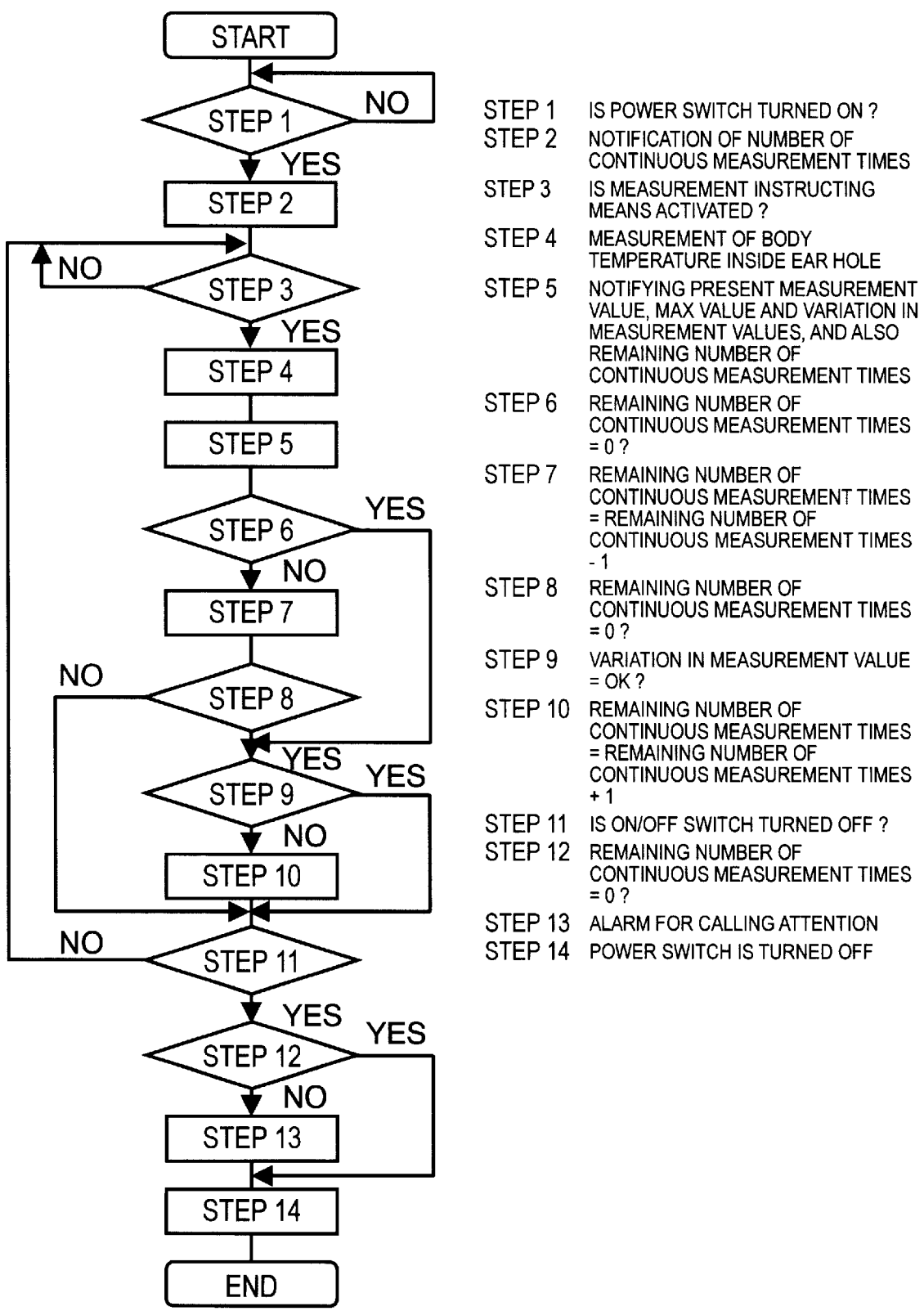
FIG. 40 is a flow chart to show how an ear type thermometer for women in a twenty seventh exemplary embodiment of the present invention operates.

Subsequently, a description is given to an ear type thermometer for women in a twenty seventh exemplary embodiment of the present invention. The block diagram of FIG. 39 also shows the structure of the ear type thermometer for women in the present exemplary embodiment in the same way as in the twenty fifth exemplary embodiment. FIG. 40 is a flow chart to show how the ear type thermometer for women in the present exemplary embodiment operates.

Next, a description is made on how the ear type thermometer for women in the present exemplary embodiment operates. The user pushes the power on/off switch 136 to turn on the power of the maim body 131 of ear type thermometer for women (Step 1), inserts the probe 132 in the ear hole after having confirmed the display of the number of continuous measurement times determined by the continuous measurement times determining means 134 and finishes one round of the body temperature measurement by pushing the measurement instructing means 142. Up to this step of the operation process, the present exemplary embodiment is the same as the twenty sixth exemplary embodiment. The storing means 143 stores the measurement value of each respective round of measurement, thereafter, and notifies by displaying on the liquid crystal display device the maximum value during the period of the continuous measurement times and a variation in measurement values (a value derived by subtracting the minimum value from the maximum value, 0.1° C., for example) for each respective round of measurement at the same time as the measurement value for each respective round of measurement is notified. Further, the remaining number of continuous measurement times is displayed at the same time. (Step 2 to Step 5) When the user tries to turn of the power of the main body of ear type thermometer for women by pushing the power on/off switch 136 before the remaining number of continuous measurement times becomes zero (Step 11 to Step 12), the continuous measurement times determining means 134 has a chopped beep sounded as the buzzer sounding unit constituting the notifying means 135 (Step 13) and then has the power of the main body 131 of ear type thermometer for women turned off. (Step 14)

Accordingly, the ear type thermometer for women in the present exemplary embodiment allows the user to create awareness about obtaining measurement values with enhanced reliability.

(Twenty Eighth Exemplary Embodiment)

Figure 41:
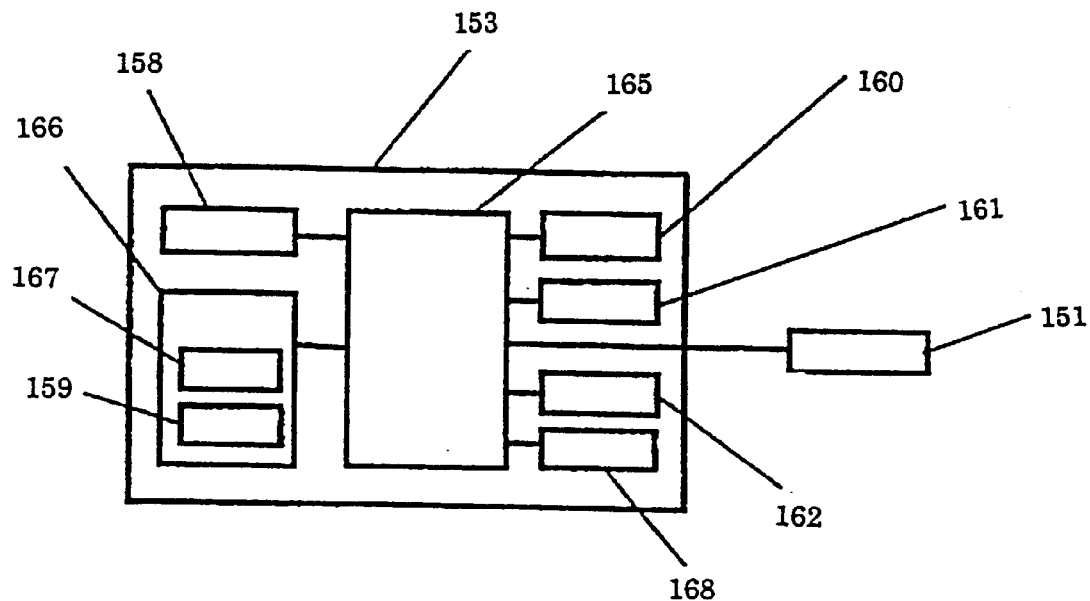
FIG. 41 is a block diagram to show the structure of an ear type thermometer for women in a twenty eighth exemplary embodiment of the present invention.

Next, a description is given to an ear type thermometer for women in a twenty eighth exemplary embodiment of the present invention. FIG. 41 is a block diagram to show the structure of electrical circuits of the ear type thermometer for women in the present exemplary embodiment. The reference numeral 151 is a body temperature measurement unit and connected to a controlling means 165 of a data processing display device 153. The controlling means 165 is connected with the body temperature measuring means 151, a menstruation start date entering means 160, a desired delivery date entering means 161, a storing means 162, a liquid crystal display device 158 constituting a notifying means to notify body temperatures measured by the body temperature measuring unit 151 and the like, an alarming sound generator 166 formed of a speaker 159 and a buzzer 167 and a clocking means 168 having a calendar function.

Figure 42:
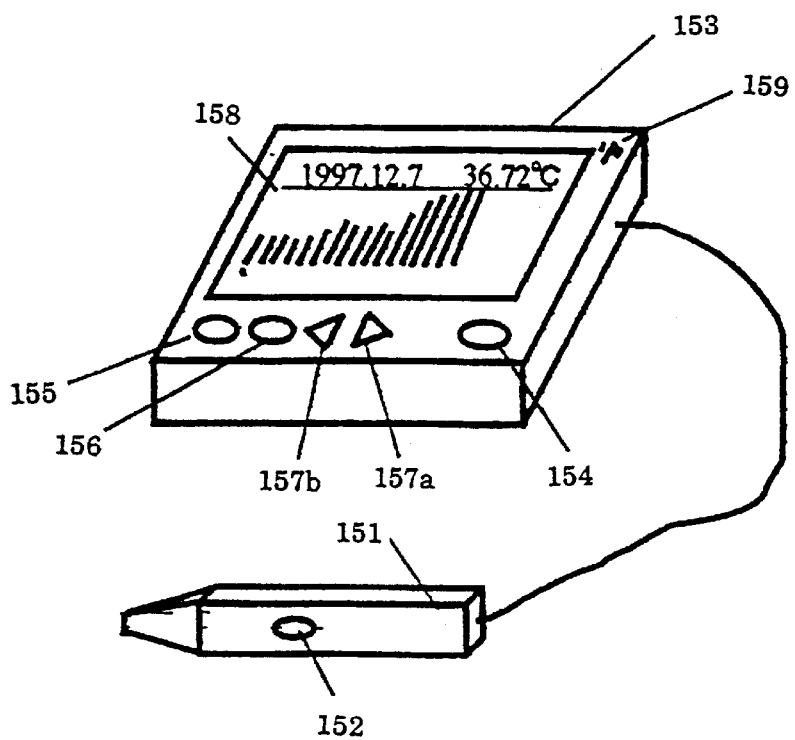
FIG. 42 is a perspective view to show the structure of the ear type thermometer for women in the twenty eighth exemplary embodiment of the present invention.

FIG. 42 is a perspective view to show the outward appearance of the ear type thermometer for women in the present exemplary embodiment. The body temperature measurement unit 151 is to measure body temperatures when the user pushes the measurement instructing means 152 and formed of a thermistor. The body temperature data obtained at the body temperature measurement unit 151 is transmitted to the date processing display device 153. The data processing display device 153 comprises the liquid crystal display device 158 constituting the notifying means, the speaker 159, a menstruation start date entry switch 155 constituting a menstruation start date entering means whereby the user enters the first day of each respective menstrual period, a desired delivery date entry switch 156 constituting a desired delivery date entering means whereby the user enters a desired delivery date, a data invoking on/off switch 154 constituting the menstruation start date entering means and desired delivery date entering means, respectively, a "+" switch 157a and a "−" switch 157b.

Figure 43:
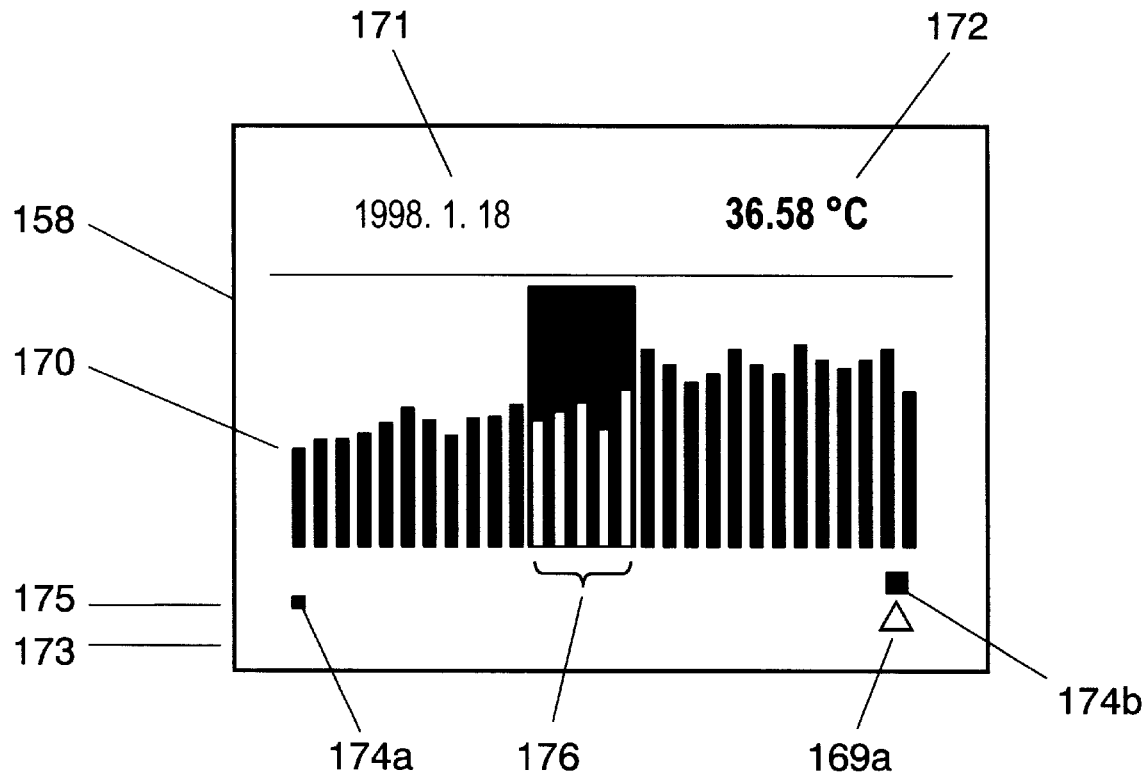
FIG. 43 is a diagram to illustrate the display picture screen as shown on a liquid crystal display device of the ear type thermometer for women in the twenty eighth exemplary embodiment of the present invention.

A description is given to FIG. 43, which is a diagram to illustrate a typical ordinary display picture of the data invoked by operating the data invoking on/off switch 154. The reference numeral 158 is a liquid crystal display device and the reference symbol 169a is a pointer to point to each respective bar of a body temperature bar graph 170. The date and basal body temperature corresponding to the bar are indicated in a date column 171 and a body temperature column 172, respectively. The pointer 169a moves horizontally on a pointer display line 173 in parallel to the X axis of the body temperature bar graph 170 to indicate each respective bar of above. The reference symbols 174a and 174b are menstruation start date marks. The bar located at the place indicated by the menstruation start date mark 174a or 174b means the bar of the corresponding menstruation start date. The menstruation start date marks 174a and 174b appear on a menstruation start date mark display line 175 located in parallel to the X axis of the body temperature graph 170 and above the pointer display line 173. The reference numeral 176 is an ovulation period indication made by estimation.

Next, a description is made on how the ear type thermometer for women in the present exemplary embodiment operates. Upon finding out that the time has reached a daily predetermined time via the clocking means 168, the controlling means 165 notifies the user by using the buzzer 167 and speaker 159 constituting the alarming sound generator 166 that the time to carry out a body temperature measurement is reached. At this time of carrying out the body temperature measurement, a basal body temperature of the user is to be measured while the user lies quietly before getting up in the morning and the time of measurement is allowed to be determined so as to suit the convenience of the user m consideration of her life pattern. Upon receiving this notification, the user carries out a basal body temperature measurement by pushing the measurement instructing means 152 of the body temperature measurement unit 151. Since the measurement dates can be known via the clocking means 168, the controlling means 165 has the measured body temperatures stored in the storing means 162 automatically so as to allow the user to tell the measurement dates associated with the body temperatures. More specifically, the controlling means 165 has the first day only out of the measurement dates stored in the storing means 162. With respect to the body temperatures, the controlling means 165 has the body temperature of the first day and one additional body temperature per day thereafter stored in the storing means 162 in succession. As a result, with respect to the measurement date corresponding to each respective body temperature, the controlling means 165 identifies the dates according to the order whereby the first day of the measurement and respective body temperatures thereafter are stored. The controlling means 165 displays a body temperature for each respective date when the body temperature measurement is performed on the liquid crystal display device 158 and also invokes the past data on body temperatures stored in the storing means 162 to display on the liquid crystal display device 158 as a graph. FIG. 43 is an ordinary display picture to show such a graph as an example.

When past body temperatures are to be checked, the "+" switch 157a or "−" switch 157b is pushed to move the pointer 169a horizontally. As the pointer 169 is moved, the date displayed in the date column 171 and the body temperature displayed in the body temperature column 172 are changed.

Further, with the present exemplary embodiment, a menstruation start date is entered while the ordinary display picture of FIG. 43 being watched. In other words, when the date displayed in the date column 171 happens to be a menstruation start date, the menstruation start date entering switch 155 is pushed under this status. Further, when the date displayed in the date column 171 is not the menstruation start date, the date of the menstruation start date itself is displayed in the date column 171 by operating the "+" switch 157a or "−" switch 157b, and then the menstruation start date entering switch 115 is pushed. It does not matter whether the menstruation start date is entered before or after measuring body temperatures and also whether on or after the menstruation start date. When the menstruation start date is thus entered, the menstruation start date mark 174b is displayed on the menstruation start date mark display line 175 at a place under the corresponding bar of the graph and stored in the storing means 162 accordingly. When the menstruation start date as indicated by the menstruation start date mark 174b happens to be wrong, the menstruation start date entering switch 155 is pushed while the pointer 169a being moved to the position of 174b, and then the menstruation start date mark 174b disappears and deleted from the storing means 162 also. Thus, the menstruation start date marks 174a and 174b are established by the user.

According to the present exemplary embodiment, an entry of the menstruation start date is thus performed three times or more and stored in the storing means 162 accordingly, thereby allowing the controlling means to predict the future menstruation start date. More specifically, the interval between menstruation start dates is taken as the number of days in a period corresponding to each respective menstrual period and the menstruation start date at the nth period in future is predicted as (the most recent menstruation start date +n × the average number of days in a menstrual period) based on the average number of days in a menstrual period and the most recent menstruation start date. At this time, the controlling means 165 derives the number of days in each respective period by recalculation every time when the menstruation start date stored in the storing means 162 is renewed, thereby always trying to have the menstruation start date in future predicted based on the most recent data available.

Also, according to the present exemplary embodiment, a future ovulation date is predicted at the same time as the menstruation start date is predicted. In other words, at the time when the future menstruation start date is determined, an ovulation date in the past is derived by estimation based on the body temperature data stored m the storing means 162. The estimated ovulation date in the past is derived by calculation from the stored body temperatures by considering the date of two days before the high temperature period as the ovulation date for each respective menstrual period. At this time, the display screen of the liquid crystal display device 158 shows the five days before the high temperature period as the ovulation period by inverting the colors in the corresponding bars as FIG. 43 shows by the reference numeral 176. Thus, when the past ovulation date is allowed to estimated, the controlling means 165 predicts the ovulation date at the nth period in future as ((the most recent menstruation start date+n×the average number of days in a menstrual period)—the average number of days in a high temperature period—2) based on the future menstruation start date already predicted and the data on the past ovulation dates.

Further, according to the present exemplary embodiment, the user pushes the desired delivery date entering switch 156, thereby allowing the user to establish a desired delivery date. In other words, when the user pushes the desired delivery date entering switch 156, the display screen of the liquid crystal display device changes to an input display for a desired delivery date. What is established on the display screen can become a desired delivery date by operating the "+" switch 157a and "−" switch 157b when the future ovulation date is allowed to have been predicted. When the future ovulation date can not be predicted due to the insufficient or irregular data stored in the storing means 162, the controlling means 165 activates the alarming sound generator 166 without changing the entry in the desired delivery date entry column 177 even if the "+" switch 157a or the "−" switch 157b is pushed. In other words, by having the buzzer 167 sounded, the user is notified that the entry of the data is not possible. The desired delivery date that can be entered in the desired delivery date entry column 177 ranges from one year in future from the entry date to two years in future from the entry date according to the present exemplary embodiment. This establishment of the desired delivery date is performed by having the time of around April, 1999, for example, entered in the desired delivery date entry column 177 with the "+" switch 157a or the "−" switch 157b, and by pushing again the desired delivery date entry switch 156 while having the foregoing state maintained, thereby having this date fixed.

Figure 44:
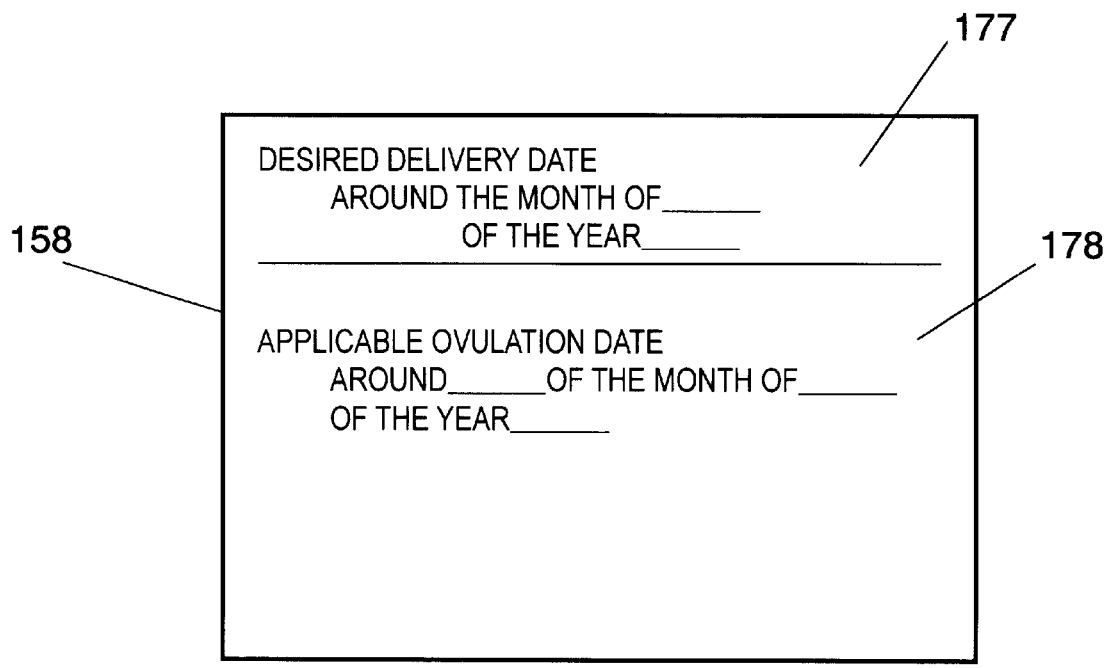
FIG. 44 is a diagram to illustrate the input picture screen of a desired delivery date as shown on the liquid crystal display device of the ear type thermometer for women in the twenty eighth exemplary embodiment of the present invention.
Figure 45:
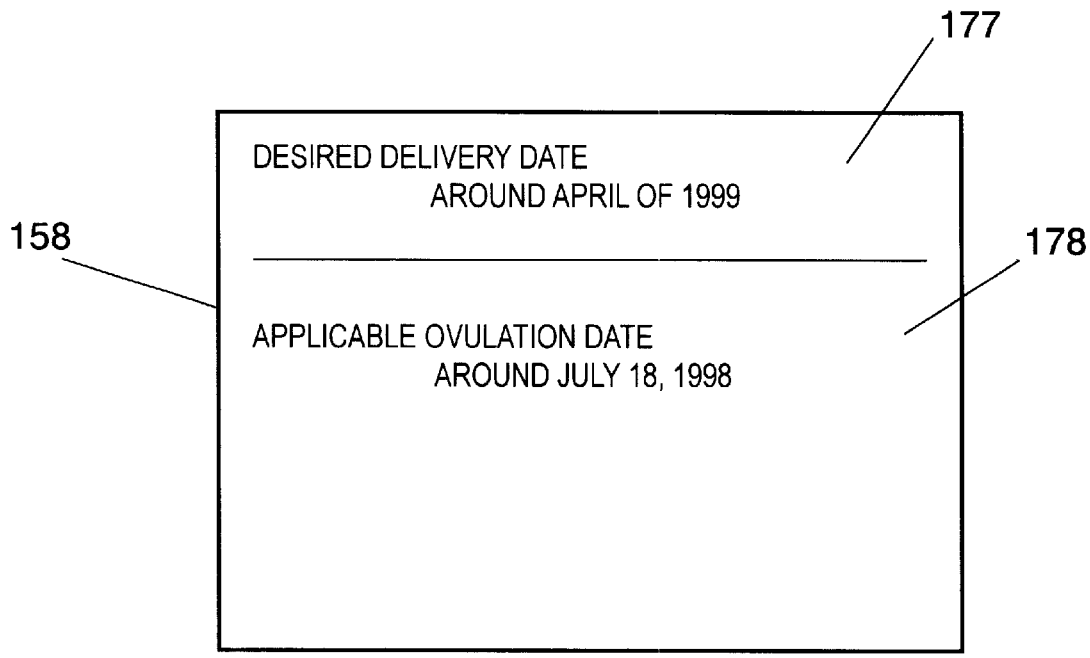
FIG. 45 is a diagram to illustrate the picture screen notifying an applicable ovulation date as shown on the liquid crystal display device of the ear type thermometer for women in the twenty eighth exemplary embodiment of the present invention.

Thus, upon having the desired delivery date fixed, the controlling means 165 displays an applicable ovulation date in an applicable ovulation date display column 178 as FIG. 44 shows. More specifically, the inverse operation is applied to the desired delivery date with the standard 40 weeks taken as the pregnancy period from the menstruation start date before pregnancy and, from the dates derived by calculation performed according to (the desired delivery date −40 weeks+(the average number of days in a menstrual period— the average number of days during a high temperature period —2), the date nearest the future ovulation date predicted by the ovulation predicting means 164 is selected and displayed as "around Jul. 18, 1998", for example, as FIG. 45 shows.

When it comes to confirming the desired delivery date thus established at a later date, the desired delivery date entry switch 156 is just pushed. In other words, when the desired delivery date entry switch 156 is pushed, the controlling means 165 has the data on the desired delivery date stored in the storing means 162 as of this time displayed as FIG. 45 shows, thereby allowing the user, to confirm the applicable ovulation date by looking at the display screen.

Therefore, according to the present exemplary embodiment, the user measures the basal body temperatures every morning and simply enters a menstruation start date by means of the menstruation start date entry switch 155 on that day with only the process of entering a desired delivery date performed thereafter, thereby enabling the user to know the pregnant period.

According to the present exemplary embodiment, the desired delivery date entry column 177 is intended for entering year and month only, but this can be changed to entering the desired delivery date expressed in terms of year, month and even day. In addition, although an applicable ovulation date is notified by means of a display screen separate from the ordinary display screen in the present exemplary embodiment, it does not matter whether the notification is made by displaying always on the ordinary display screen. Furthermore, although the body temperature measurement unit 151, which is an oral thermometer using a thermister, is connected with the main body 131 of ear type thermometer for women by wire, it does not matter whether an ear type thermometer using an infrared sensor is employed instead and also data is transmitted by wireless to the main body 131 of ear type thermometer for women via infrared rays, electromagnetic waves and the like.

(Twenty Ninth Exemplary Embodiment)

Figure 46:
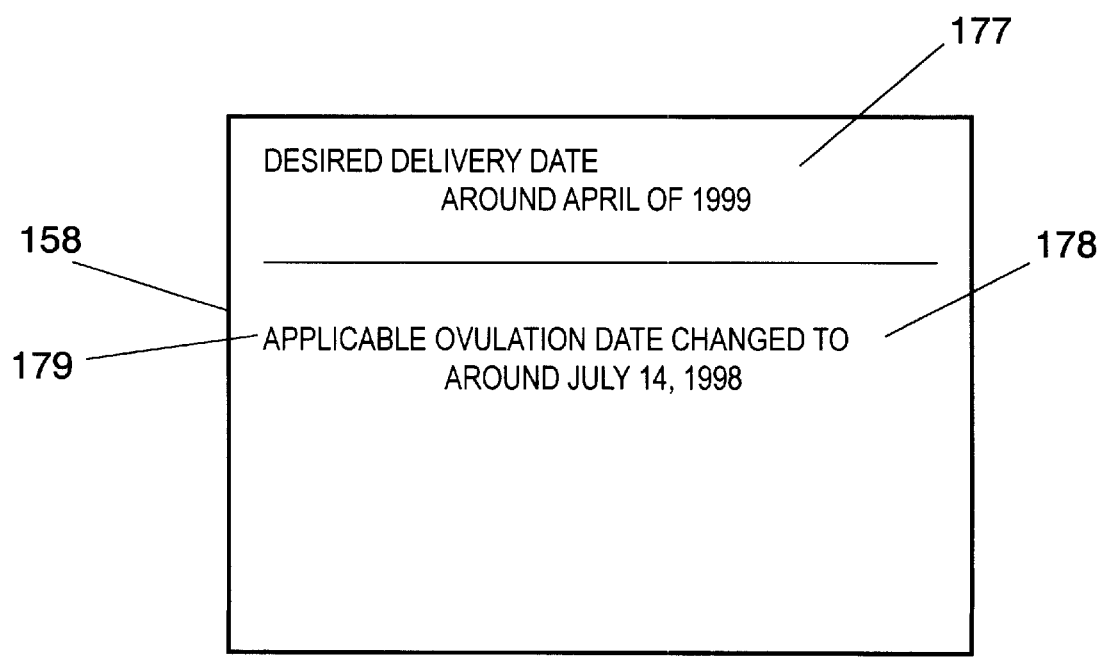
FIG. 46 is a diagram to illustrate the picture screen changing an applicable ovulation date as shown on a liquid crystal display device of an ear type thermometer for women in a twenty ninth exemplary embodiment of the present invention.

Next, a description is given to an ear type thermometer for women in a twenty ninth exemplary embodiment of the present invention. The present exemplary embodiment deals with the case where a predicted ovulation date deviates from the initially predicted ovulation date due to disturbed physical condition and the like. More specifically, the controlling means 165 predicts an ovulation date based on the most recent data stored in the storing means 162. Therefore, the ovulation date thus predicted is liable to change in accordance with the basal body temperature data, menstruation start date data and the like that the user has entered thereafter. According to the present exemplary embodiment, upon finding out that the foregoing deviation in the predicted ovulation date exists, the controlling means 165 activates the alarming sound generator 166 to generate alarming sounds and also displays a picture screen of changing the applicable ovulation date for a predetermined time period on the liquid crystal display device 158 as FIG. 46 shows. In FIG. 46, the reference numeral 177 is a desired delivery date entry column, 178 is an applicable ovulation date display column and 179 is a change indication to show clearly that there exists an alteration to the applicable ovulation date. In addition, during the aforementioned predetermined time period, the display in the applicable ovulation date display column 178 and change indication 179 blinks.

Since the applicable ovulation date is notified on a display screen set up separately from the ordinary display screen in the present exemplary embodiment, the methods as described in above is employed. However, when the same is displayed on the ordinary display screen all the time, it does not matter whether an alarming sound is generated at the alarming sound generator 166 and only the applicable ovulation date display column 178 and change indication 179 are made to blink. Further, although the notification of change is to be made for a predetermined time period in the foregoing, it may be allowed to make an arrangement that until the time when the user makes an entry one way or another after the notification of change is made.

Thus, according to the present exemplary embodiment, the change in the applicable ovulation date is notified when the basal body temperatures are measured or the menstruation start dates are entered, thereby allowing the user to find out promptly that there is a change in the applicable ovulation date and a more accurate applicable ovulation date that corresponds to the desired delivery date.

(Thirtieth Exemplary Embodiment)

Figure 47:
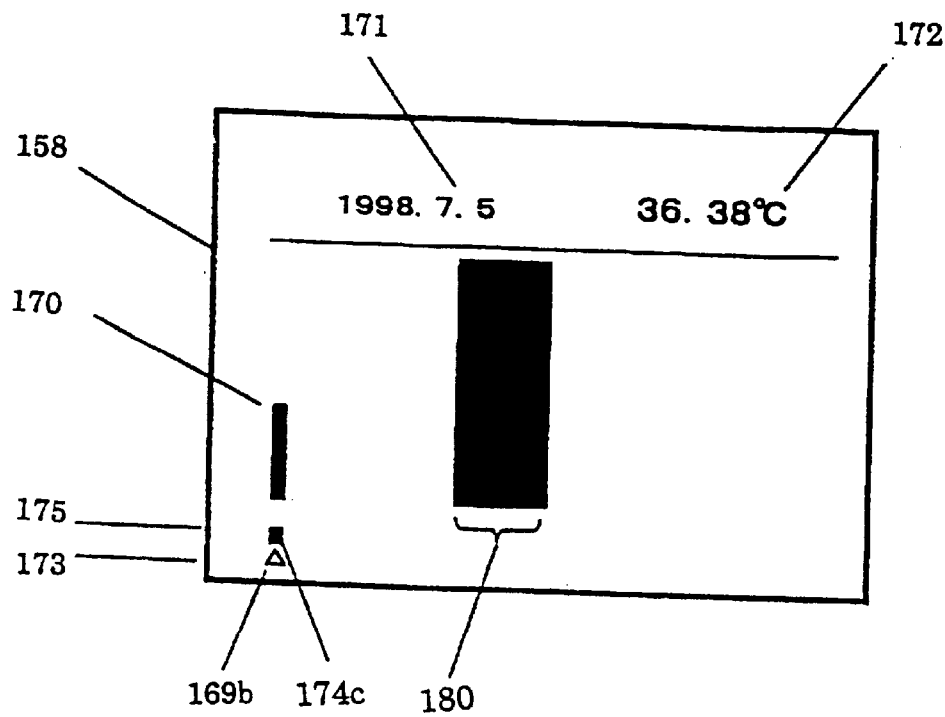
FIG. 47 is a diagram to illustrate the picture screen displaying an applicable ovulation date of an ear type thermometer for women in a thirtieth exemplary embodiment of the present invention.

Subsequently, a description is given to an ear type thermometer for women in a thirtieth exemplary embodiment of the present invention. According to the present exemplary embodiment, when a menstruation start date is entered by the menstruation start date entering means 160 and in a case where a notified applicable ovulation date falls in the time period ranging from the entered menstruation start date to the menstruation start date of the next time, the controlling means 165 notifies of the applicable ovulation date on the display screen of the liquid crystal display device 158 or of the fact that the applicable ovulation date falls in the menstrual period. FIG. 47 is an example of the display screen showing the displayed content of the foregoing. The display screen as FIG. 47 shows is displayed by the liquid crystal display device 158 when the data is invoked by the data invoking on/off switch 154.

Next, a description is made on how the ear type thermometer for women operates. When the date of Jul. 5, 1998 is displayed in the date column 171 as FIG. 47 shows, a menstruation start date is entered and a corresponding menstruation start date mark 174c is entered in the menstruation start date mark display line 175, resulting supposedly in a prediction of the menstruation start date of next time that reads "Aug. 2, 1998". The controlling means 165 determines that the applicable ovulation date of "Jul. 18, 1998" falls in the time period between the entered menstruation start date, i.e., "Jul. 5, 1998" and the menstruation start date of next time, i.e.,; "Aug. 2, 1998". At this time, the controlling means 165 has the applicable ovulation date notifying display screen displayed as FIG. 45 shows in place of FIG. 47 for a predetermined time period The display screen of FIG. 47 is displayed again, thereafter, but at this time the applicable ovulation period display 180 is being made to blink.

According to the present exemplary embodiment, at the time when a menstruation start date is entered, a notification of an applicable ovulation date and a notification to the effect that the applicable ovulation date falls in the menstrual period are made at the same time, but it is also allowed to make any one of the foregoing notifications. In addition, although the fact that the applicable ovulation date falls in the menstrual period is notified by blinking the applicable ovulation period display 180 of the graph, it does not matter whether a notification is given by clearly describing by letters as "the applicable ovulation date falls in the menstrual period". Furthermore, since a notification is given of the applicable ovulation date on a display screen, which is separate from the ordinary display screen, the foregoing method is employed, but when the same is displayed on the ordinary display screen all the time, it does not matter whether an alarming sound is generated at the alarming sound generator 166 and only the applicable ovulation date display column 17 is made to blink. Further, although the notification of change is to be made for a predetermined time period in the foregoing, it may be allowed to make an arrangement that until the time when the user makes an entry one way or another after the notification of change is made.

Thus, according to the present exemplary embodiment, the user is allowed to know on the first day of the menstrual period of an applicable menstrual period that the user is already in the menstrual period in question, thereby allowing the user to pay a special attention to her physical condition.

(Thirty First Exemplary Embodiment)

Figure 48:
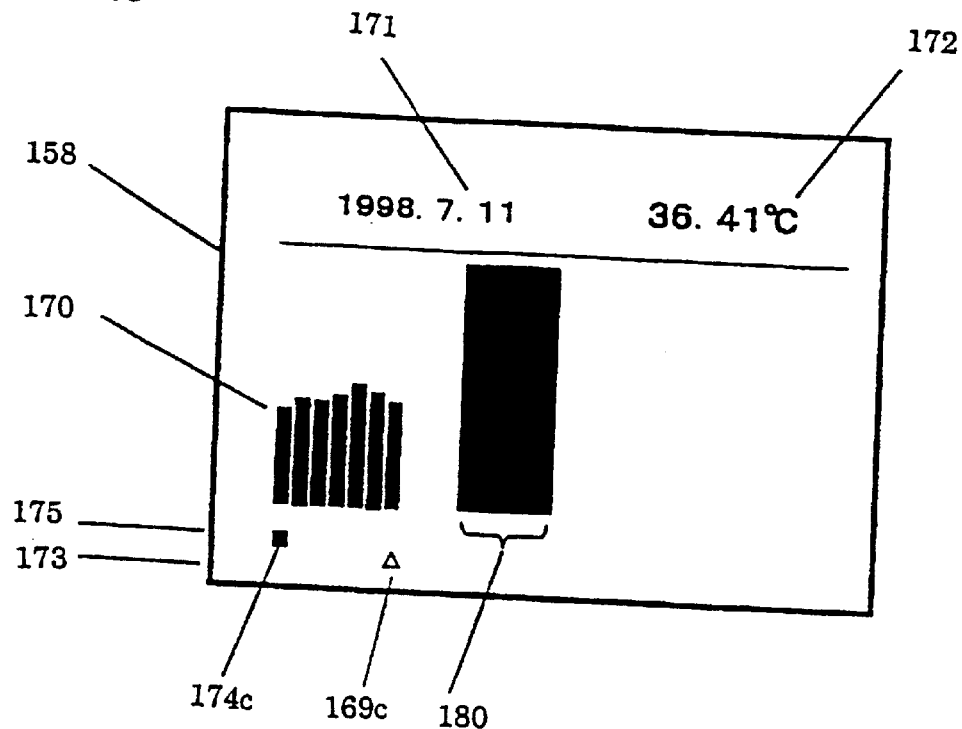
FIG. 48 is a diagram to illustrate the picture screen displaying an applicable ovulation date of an ear type thermometer for women in a thirty first exemplary embodiment of the present invention.

Subsequently, a description is given to an ear type thermometer for women in a thirty first exemplary embodiment of the present invention. According to the present exemplary embodiment, when the notified applicable ovulation date falls between the most recent menstruation start date entered by the user and the predicted menstruation start date of next time, the controlling means 165 notifies of the applicable ovulation date by displaying on the liquid crystal display device 158 or notifies on the liquid crystal display device 158 of the fact that the applicable ovulation date falls in the menstrual period. FIG. 48 is an example of the ordinary display screen displaying the foregoing.

Next, a description is made on how the ear type thermometer for women in the present exemplary embodiment operates. When the basal body temperature is to be measured every morning, the user operates the measurement instructing means 152 after an alarming sound is generated from the alarming sound generator 166. When a menstruation start date is entered, the data invoking on/off switch 154 is first operated. When the controlling means 165 detects the entries of above and the applicable ovulation date falls between the most recent menstruation start date and the menstruation start date of next time, supposing, for example, that the applicable ovulation date is "Jul. 18, 1998", the most recent menstruation start date is "Jul. 5, 1998" and the menstruation start date of next time is "Aug. 2, 1998", the controlling means 165 first has the applicable ovulation date notifying screen of FIG. 45 displayed for a predetermined time period before displaying the screen as FIG. 48 shows and then displays the screen of FIG. 48. At this time, the applicable ovulation period display 180 is made to blink.

Further, according to the present exemplary embodiment, in a case where the applicable ovulation date falls between the most recent menstruation start date and the menstruation start date of next time, i.e., in the corresponding menstrual period, a notification is given every time when actions on the part of the user such as a body temperature entry, a data invoking operation and the like are recognized during the menstrual period, and even when no actions are taken by the user, a notification is allowed to be given periodically. According to the present exemplary embodiment, a notification of an applicable ovulation date and a notification to the effect that the applicable ovulation date falls in the menstrual period are made at the same time, but it is also allowed to make only any one of the foregoing notifications. In addition, although the fact that the applicable ovulation date falls in the menstrual period is notified by blinking the applicable ovulation period display 180 of the graph, it does not matter whether a notification is given by clearly describing by letters as "the applicable ovulation date falls in the menstrual period". Furthermore, since a notification is given of the applicable ovulation date on a display screen, which is separate from the ordinary display screen, the foregoing method is employed, but when the same is displayed on the ordinary display screen all the time, it does not matter whether an alarming sound is generated at the alarming sound generator 166 and only the applicable ovulation date display column 17 is made to blink. Further, although the notification of change is to be made for a predetermined time period in the foregoing, it may be allowed to make an arrangement that until the time when the user makes an entry one way or another after the notification of change is made.

Thus, according to the present exemplary embodiment, the user is made aware that the user is already in the menstrual period of the applicable ovulation date, thereby allowing the user to pay an attention to her physical condition.

(Thirty Second Exemplary Embodiment)

Figure 49:
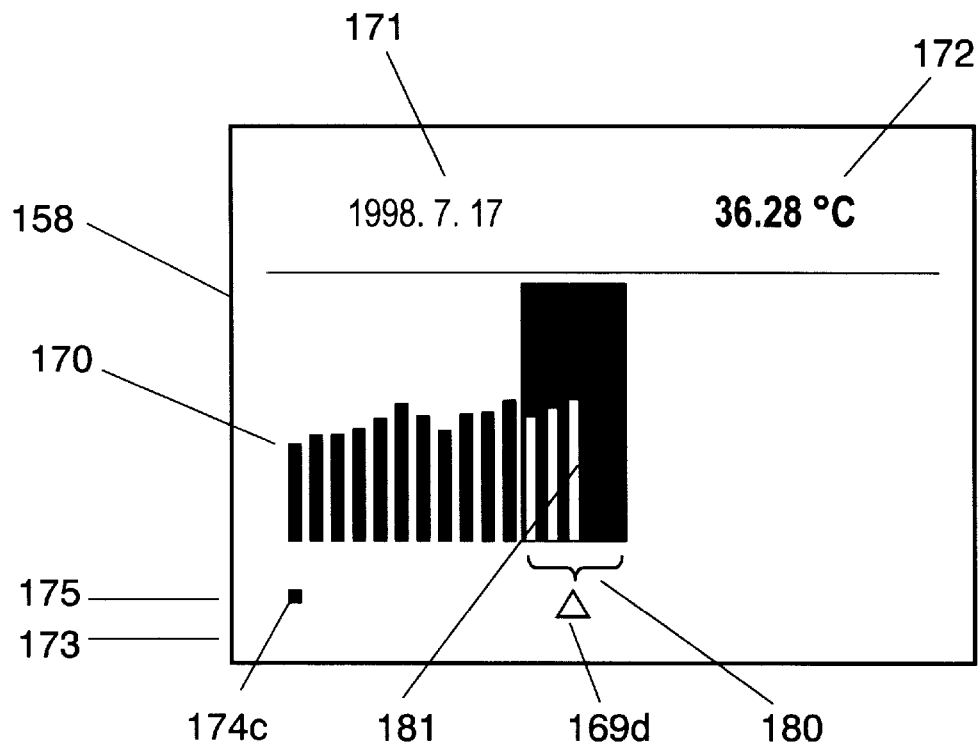
FIG. 49 is a diagram to illustrate the picture screen displayed by an ear type thermometer for women in a thirty second exemplary embodiment of the present invention.

Next, a description is given to an ear type thermometer for women in a thirty second exemplary embodiment of the present invention. According to the present exemplary embodiment, when the date of measuring a body temperature by the body temperature measuring means 151 falls within a predetermined number of days before and after the notified applicable ovulation date and also the body temperature measured on that particular date is found to be the lowest in comparison with the body temperature values measured within a predetermined number of days before and after the applicable ovulation date already stored in the storing means 162, the controlling means 165 is to give a notification to the effect that the particular date is most likely to be the true applicable ovulation date. FIG. 49 is an example of the display screen at this particular time. The applicable ovulation period display 180 shows the changes in body temperatures among the three days in total including the applicable ovulation date itself expressed as "Jul. 18, 1998" and another day before and after the applicable ovulation date. The bar indicated by the reference numeral 181 is the body temperature graph of July 17, which is found to be lowest among the three values in body temperature measured during the period "from Jul. 15 to Jul. 17, 1998", displayed on the applicable ovulation period display 180 and already stored in the storing means 162.

Now, a description is made on how the ear type thermometer for women in the present exemplary embodiment operates. When the body temperature of "July 15" is entered, the controlling means 165 makes a comparison between body temperatures. The date of "July 15" is the first day of the applicable ovulation period display 180 and no notification is made in particular. When the body temperature of "July 16" is entered, the controlling means 165 does not make any particular notification since the body temperature of that day is higher than the body temperature of "July 15" that is already stored in the storing means 162. Then, when the body temperature of "July 17" is entered, the controlling means 165 determines the body temperature of "July 17" to be lowest in comparison with the body temperatures of "July 15" and "July 16". As a result, the controlling means 165 activates the alarming sound generator 166 and has an alarming sound generated and makes the body temperature, graph 181 of July 17 blink until additional new body temperatures are entered, thereby making a notification to the effect that there is a great possibility for the date of "July 17" to be the true applicable ovulation date.

Although the predetermined number of days before and after the applicable ovulation date is made as three days before and one day after the applicable ovulation date, respectively, according to the present exemplary embodiment, this can be established so as to be an arbitrary number of days with reference to the applicable ovulation date. Although a notification is not made of the first day of the predetermined number before the applicable ovulation date (corresponding here to the first day of the applicable ovulation period), this can be notified any time. In addition, the fact that there is a great possibility to be the exact applicable ovulation date is notified by blinking the applicable bar graph but it does not matter whether a notification is given by clearly describing by letters as "the great possibility of the applicable ovulation date". Further, although the notification is said to be made by blinking the body temperature graph 181 of July 17 until additional new body temperatures are entered, it does not matter whether the blinking is made to continue for a predetermined time period.

Thus, according to the present exemplary embodiment, the user is allowed to know a more accurate applicable ovulation date.

(Thirty Third Exemplary Embodiment)

Figure 50:
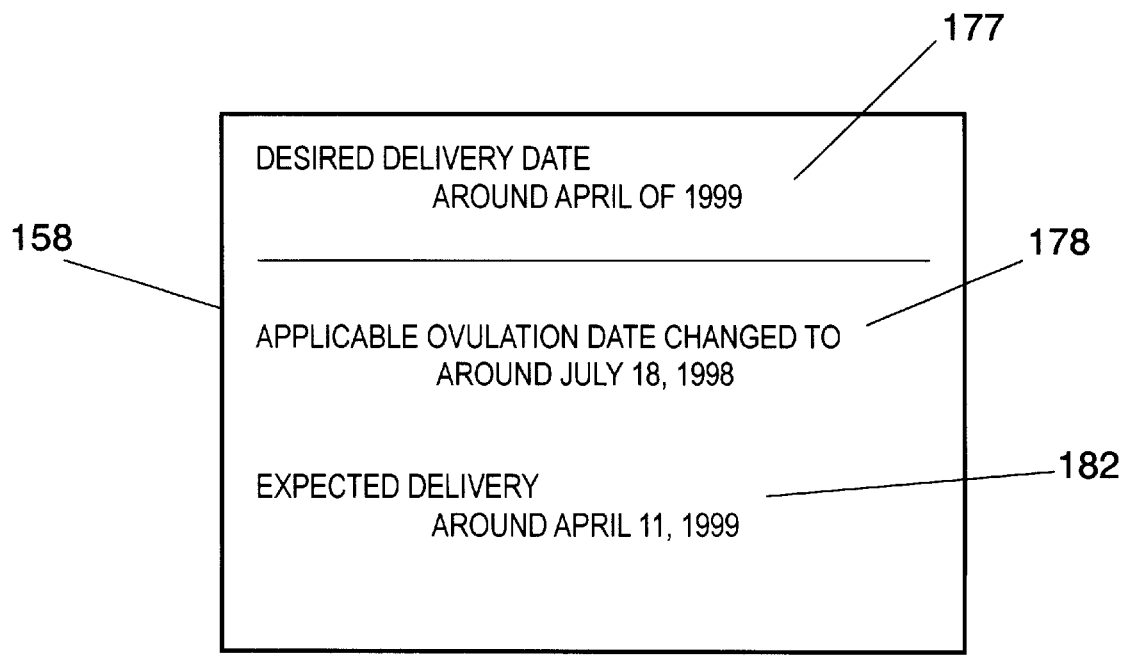
FIG. 50 is a diagram to illustrate the picture screen displaying an expected delivery date of an ear type thermometer for women in a thirty third exemplary embodiment of the present invention.

Subsequently, a description is given to an ear type thermometer for women in a thirty third exemplary embodiment of the present invention. According to the present exemplary embodiment, the controlling means 165 provides notification about the expected delivery date based on an assumption that the period of pregnancy starts on the applicable ovulation date. FIG. 50 is an example of the display screen according to the present exemplary embodiment.

Now, a description is made on how the ear type thermometer for women in the present exemplary embodiment operates. Upon entry of a desired delivery date in the desired delivery date entry column 177, an applicable ovulation date is displayed in the applicable ovulation date display column 178 as described in the twenty eight exemplary embodiment. When the applicable ovulation date is fixed and the period of pregnancy is assumed to start on the applicable ovulation date, the expected delivery date is derived by calculation based on the normal pregnancy period, an alarming sound is generated from the alarming sound generator 166 and consequently the expected delivery date is displayed in the expected delivery date display column 182. Upon checking the date displayed in the expected delivery date display column 182, the user applies an adjustment to the value in the desired delivery date entry column 177 so that the expected delivery date becomes closer to the desired delivery date as much as possible.

Thus, according to the present exemplary embodiment, a fine adjustment can be applied to the desired delivery date by finding out the discrepancy between the expected delivery date and the desired delivery date. Although the value entered in the desired delivery date entry column 177 is expressed by year and month according to the present exemplary embodiment, an entry by year, month and day makes the desired delivery date more exact, thereby multiplying the benefit of indicating the desired delivery date.

(Thirty Fourth Exemplary Embodiment)

Figure 51:
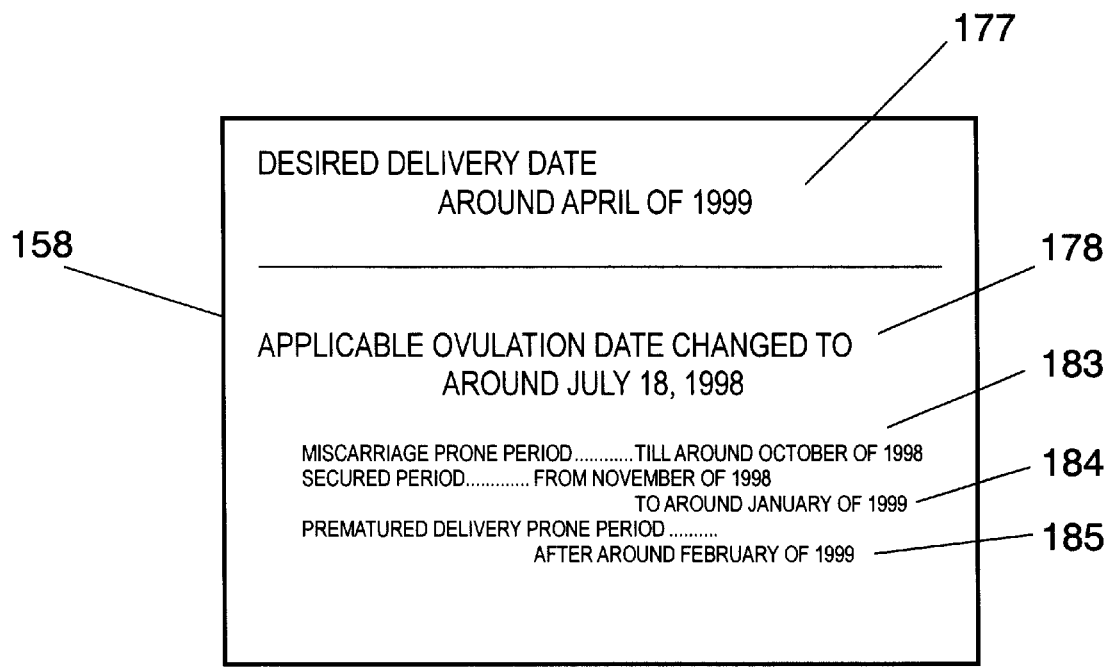
FIG. 51 is a diagram to illustrate the picture screen displaying a secure period and the like of an ear type thermometer for women in a thirty fourth exemplary embodiment of the present invention.

Next, a description is given to an ear type thermometer for women in a thirty fourth exemplary embodiment of the present invention. According to the present exemplary embodiment, the controlling means 165 provides notification about a miscarriage prone period, a secure period and a premature delivery prone period based on an assumption that the period of pregnancy starts on the notified ovulation date. FIG. 51 is an example of the display screen showing this information.

Now, a description is made on how the ear type thermometer for women in the present exemplary embodiment operates. Upon entry of a desired delivery date in the desired delivery date entry column 177, an applicable ovulation date is displayed in the applicable ovulation date display column 178 as described in the twenty eight exemplary embodiment. According to the present exemplary embodiment, when the applicable ovulation date is fixed, the controlling means 165 activates the alarming sound generator 166 to generate an alarming sound and displays the miscarriage prone period, secure period and premature delivery prone period in a miscarriage prone period display column 183, a secure period display column 184 and a premature delivery prone period display column 185, respectively, based on an assumption that the period of pregnancy starts on the applicable ovulation date. Upon checking the date displayed, the user applies an adjustment to the value in the desired delivery date entry column 177 so that the expected delivery date becomes closer to the desired delivery date as much as possible.

Although the values entered in the in the miscarriage prone period display column 183, secure period display column 184 and premature delivery prone period display column 185 are expressed by year and month according to the present exemplary embodiment, it does not matter whether the entries are made by year, month and day.

Thus, according to the present exemplary embodiment, the user tries to change the desired delivery date variously while checking such periods as the miscarriage prone period, secure period and premature delivery prone period displayed by changing in synchronization with the desired delivery date, thereby allowing the user to establish the delivery plan so as to be most suitable to her own activity plans during the period of pregnancy.

(Thirty Fifth Exemplary Embodiment)

Figure 52:
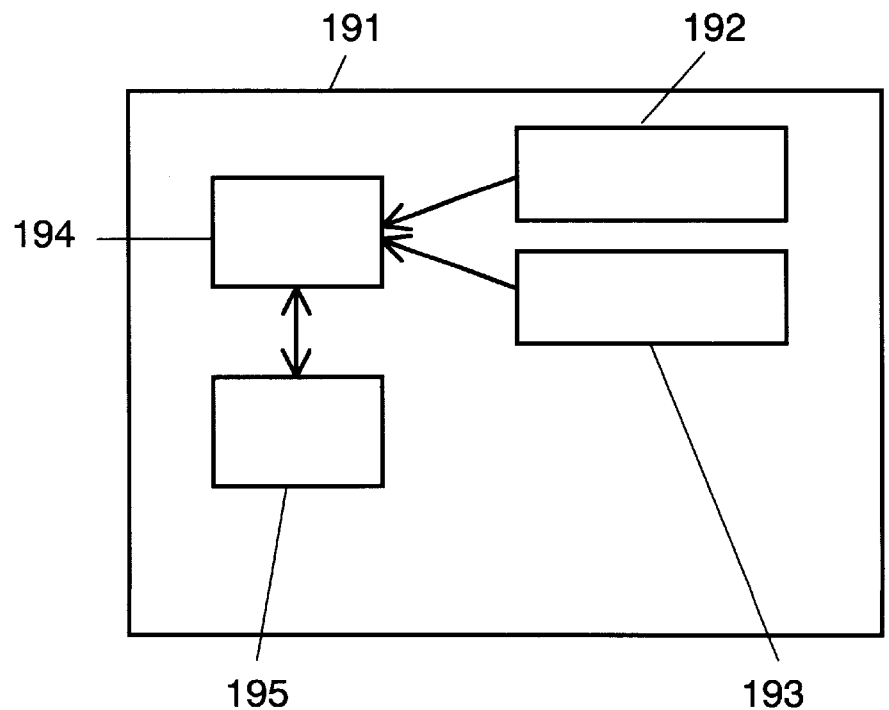
FIG. 52 is a block diagram to show the structure of an ear type thermometer for women in a thirty fifth exemplary embodiment of the present invention.

Next, a description is given to an ear type thermometer for women in a thirty fifth exemplary embodiment of the present invention. FIG. 52 is a block diagram to show the structure of the ear type thermometer for women in the present exemplary embodiment.

A data processing display device 191 of the ear type thermometer (referred to simply as a data processing display device 191 hereafter) comprises the elements of an ear type body temperature measurement unit 192, a menstruation start date entering means 193, a storing means 194 and a menstruation start date predicting means 195. The ear type body temperature measurement unit 192 comprises a thermistor, the menstruation start date entering means 193 comprises a button switch, the menstruation start date predicting means 195 comprises a microcomputer and has a calendar function.

The user places the ear type body temperature measurement unit 192 under her tongue to measure the basal body temperature under a rest once every morning before getting up while still remaining in the bed. When the user is in a menstrual period, the first day of her menstruation is entered as the menstruation start date in the menstruation start date entering means 193. The information of the basal body temperature and menstruation start date thus acquired are stored in the storing means 194 in such a way as the date of acquirement of each respective piece of the information can be identified. The menstruation start date predicting means 195 predicts future menstruation start dates of the next time and thereafter based on the data stored in the storing means 194.

Now, a description is made on how the menstruation start date predicting means 195 operates in the present exemplary embodiment with reference to a flow chart in FIG. 53.

First, the menstruation start date predicting means 195 derives by calculation the number of days in a menstrual period for each respective menstrual period based on the intervals between menstruation start dates stored in the storing means 194. Suppose the oldest menstruation start date is Jan. 1, 1998 and the second oldest menstruation start date is Jan. 29, 1998, for example, then the number of days in a first menstrual period counts 28 days. Then, the numbers of days in a menstrual period for all the menstrual periods stored in the storing means 194 are derived by calculation (Step 1) and the average number of days in a menstrual period is derived by calculation. (Step 2). Next, with respect to all the menstruation periods stored in the storing means 194, a difference between each respective number of days in a menstruation period and the calculated average number of days in a menstruation period is derived. When the difference of four days or more is found with any menstruation periods, the number of days in that particular menstrual period is made invalid and, when the difference of three days or less is found with any menstruation periods, an average body temperature in the high temperature range and an average body temperature in the low temperature range are derived by calculation for all the applicable menstruation periods. Then, the difference between the aforementioned average body temperatures is checked. If the difference is less than 0.3° C., the number of days in the applicable menstruation period is made invalid and if the difference is 0.3° C. or more, the number of days in the applicable menstruation period is made valid and determined as the valid menstruation period. (Steps 3 to 6) With respect to the menstruation periods determined as being valid, an average number of lays in a menstrual period is derived by calculation. (Step 7) Finally, (the most recent menstruation start date+n×the average number of days in valid menstrual periods) is derived by calculation, thereby predicting the menstruation start date of n'th period in future. (Step 8)

According to the present exemplary embodiment, although all the menstruation periods stored in the storing means 194 are used as the data for predicting the menstruation start date in future, only part of the menstruation periods stored in the storing means 194 is allowed to be used. In addition, although the predetermined value of difference between the numbers of days in a menstrual period is made as three days and the predetermined value of difference between the average body temperatures in high temperature ranges and the average body temperatures in low temperature ranges is made as 0.3° C., values such as a standard deviation and the like can also be used. Further, a predicting action is taken at the time when there is an entry of menstruation start dates, according to the present exemplary embodiment but it does not matter to make predictions at any time before the menstruation start date of next time.

Thus, according to present exemplary embodiment, irregular menstruation periods are eliminated, thereby enabling the supply of thermometers for women with enhanced accuracy in predicting future menstruation start dates.

(Thirty Sixth Exemplary Embodiment)

Subsequently, a description is given to an ear type thermometer for women in a thirty sixth exemplary embodiment of the present invention. FIG. 52 is a block diagram to show the structure of the ear type thermometer for women in the present exemplary embodiment in the same way as in the thirty fifth exemplary embodiment.

Now, a description is made on how the menstruation start date predicting means 195 of the present exemplary embodiment operates with reference to a flow chart of FIG. 54, in which the same step reference numerals are used for the same functions as in the thirty fifth exemplary embodiment. The flow chart of FIG. 54 is the same as the flow chart for the thirty fifth exemplary embodiment up to the step where the menstruation start date predicting means 195 determines whether each respective menstruation period is valid or invalid. When the determination on the valid menstrual periods is finished, the number of the valid menstrual periods is checked whether the number is two thirds or more of all the number of menstrual periods to be examined. (Step 9) Only when the number of the valid menstrual periods is two thirds or more of all the number of menstrual periods, the future menstruation start dates of next time and thereafter are predicted (Steps 10 to 11) and, when the number of the valid menstrual periods is less than the two thirds, any predictions are no longer made. For example, when there are ten menstrual periods to be checked in all, suppose there are seven or more of valid menstrual periods. Then, predictions are made about the future menstruation start dates. However, when the number of the valid menstrual periods is less than seven, no predictions are made about the future menstruation start dates.

Although the menstruation start date predicting means 195 is to predict future menstruation start dates, only when the number of valid menstrual periods is two thirds or more of all the number of menstrual periods to be checked, according to the present exemplary embodiment, it does not matter whether this proportion of two thirds is established arbitrarily in accordance with the applicable prediction accuracy.

Thus, according to the present exemplary embodiment, a thermometer for women with a much more enhanced accuracy in predicting future menstruation start dates is made available.

(Thirty Seventh Exemplary Embodiment)

Subsequently, a description is given to an ear type thermometer for women in a thirty seventh exemplary embodiment of the present invention. FIG. 52 is a block diagram to show the structure of the ear type thermometer for women in the present exemplary embodiment in the same way as in the thirty fifth exemplary embodiment.

Now, a description is made on how the menstruation start date predicting means 195 of the present exemplary embodiment operates with reference to a flow chart of FIG. 55. First, at the time when a menstruation start date is entered in the menstruation start date entering means 193, the menstruation start date predicting means 195 makes determinations about valid menstrual periods and predicts a menstrual start date in the same way as in the thirty fifth and thirty sixth exemplary embodiments. (Step 12) Only when this prediction was possible, the menstruation start date predicting means 195 operates as described below. (Step 13) First, the average number of days in the high temperature range of a valid menstrual period is obtained. (Step 14) Then, with respect to the basal body temperature measured by the ear type body temperature measurement unit 192, whether or not the body temperature was shifted from the low temperature range to the high temperature range is checked. (Step 15) If no shift is recognizable, any correction is not applied to the menstruation start date as predicted in Step 12. If a shift is recognizable, the menstruation start date predicted in Step 12 as "the next menstruation start date=one day before the first day of the high temperature range+the average number of days in the high temperature range" is corrected (Step 15) and also the menstruation start date of n periods in future is corrected and predicted as the next menstruation start date+(n−1)×the average number of days in valid menstrual periods. (Step 16)

Although the average number of days in a high temperature range is derived by calculation, only when the future menstruation start dates can be predicted, according to the present exemplary embodiment, it does not matter whether the average number of days in a high temperature range can be also derived by calculation whenever a menstruation start date is entered in the menstruation start date entering means 193. Further, according to the present exemplary embodiment, when the average number of days in a high temperature range is derived by calculation, only the valid menstrual periods are the objects of calculation. However, since the number of days in a high temperature range is almost constant regardless of the magnitude of the number of days in a menstrual period, the objects of calculation to derive the average number of days in a high temperature range can be the menstrual periods out of the ones determined as invalid, which have the, number of days in a menstrual period exceeding the average number of days by a predetermined value but the difference between the average body temperature in a high temperature range and the average body temperature in a low temperature range is, a predetermined value or more.

Thus, according to the present exemplary embodiment, such a thermometer for women is made available as having an enhanced accuracy in predicting future menstruation start dates, having an adverse effect due to variations in a low temperature range of the ongoing menstrual period eliminated and also having the differences between individuals taken into consideration (Thirty Eighth Exemplary Embodiment)

Figure 56:
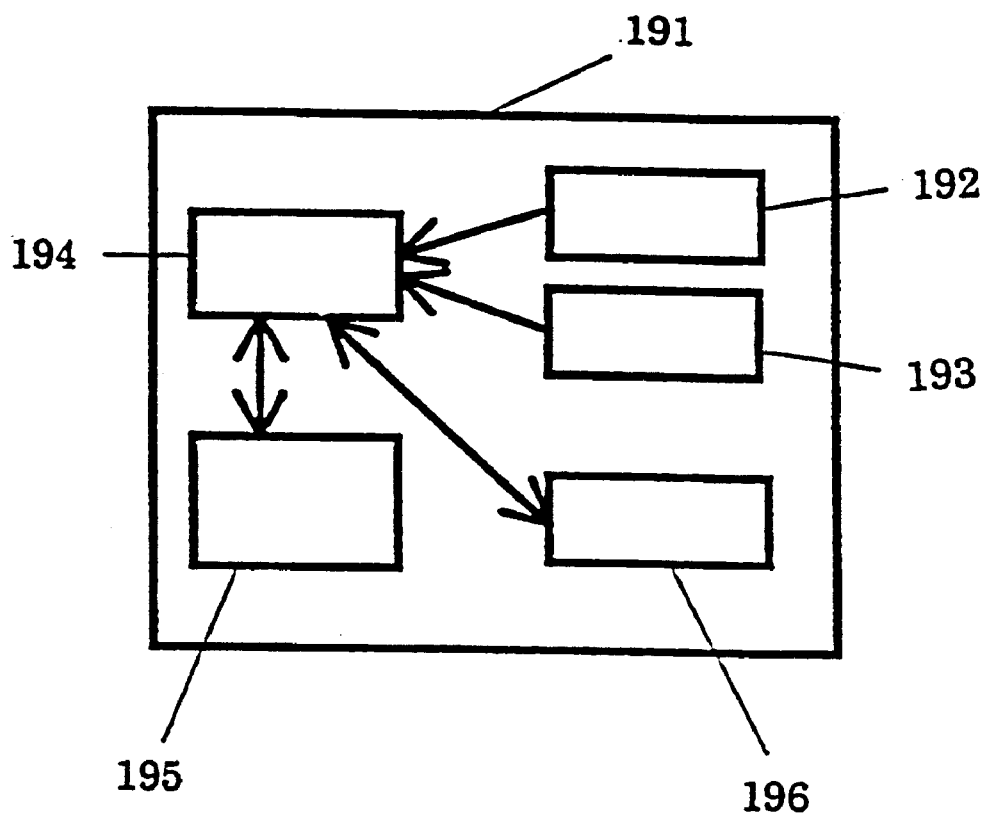
FIG. 56 is a block diagram to show the structure of an ear type thermometer for women in a thirty eighth exemplary embodiment of the present invention.

Subsequently, a description is given to an ear type thermometer for women in a thirty eighth exemplary embodiment of the present invention. FIG. 56 is a block diagram to show the structure of the ear type thermometer for women in the present exemplary embodiment.

The reference numeral 196 is a body temperature difference calculating means to derive by calculation a difference in body temperature between a menstruation start date and the day preceding the menstruation start date based on the basal body temperatures and menstruation start dates stored in the storing means 194. In FIG. 56, the same step reference numerals are used for the same functions as in the thirty fifth exemplary embodiment. The menstruation start date predicting means 195 and body temperature difference calculating means 196 comprise a microcomputer, respectively.

Now, a description is made on how the menstruation start date predicting means 195 and body temperature difference calculating means 196 of the present exemplary embodiment operate with reference to a flow chart of FIG. 57. First, at the time when a menstruation start date is entered in the menstruation start date entering means 193, the menstruation start date predicting means 195 predicts menstruation start dates thereafter or applies corrections thereto in the same way as in the thirty seventh exemplary embodiment. (Step 12 to Step 17) However, in a case where it was made possible for a menstruation start date to be predicted, at the same time the menstruation start date predicting means 195 derived by calculation the average number of days in a high temperature range, the body temperature difference calculating means 196 derives "the body temperature on the day preceding a menstruation start date—the basal body temperature on the menstruation start date" for each respective valid menstrual period, thereby deriving by calculation an average difference in body temperatures and storing the both data in the storing means 194. (Step 18) For example, an average difference of −0.2° C. in body temperatures and the like are stored in the storing means 194. When menstruation does not occur even if the next menstruation start date as predicted by the menstruation start date predicting means 195 is passed, namely, (there is no entry of the menstruation start date in the menstruation start date entering means 193) (Step 19), suppose an inequality of "the basal body temperature of the previous day—the basal body temperature measured by the ear type body temperature measuring means 192≧the average difference in body temperatures" is satisfied for a certain menstruation start date. Then, that date is taken as the corrected and predicted date of the next menstruation start date. (Step 20 to Step 21) At the same time, the menstruation start date at the nth menstrual period in future is corrected and predicted as "the next menstruation start date+(n−1)×the average number of days in a valid menstrual period". (Step 22)

Although the object, from which the body temperature differences are derived, is a valid menstrual period according to the present exemplary embodiment, it does not matter whether the body temperature differences are obtained from all the menstrual periods stored in the storing means 194 by applying a statistical process to the body temperature differences obtained.

Accordingly, with the thermometer for women in the present exemplary embodiment, when no menstruation start dates are entered to the menstruation start date entering means 193 even after the next predicted menstruation start date is passed, or even when the menstrual period has many days in a menstrual period, the prediction accuracy of future menstruation start dates can be enhanced with the differences between individuals taken into consideration.

(Thirty Ninth Exemplary Embodiment)

Figure 58:
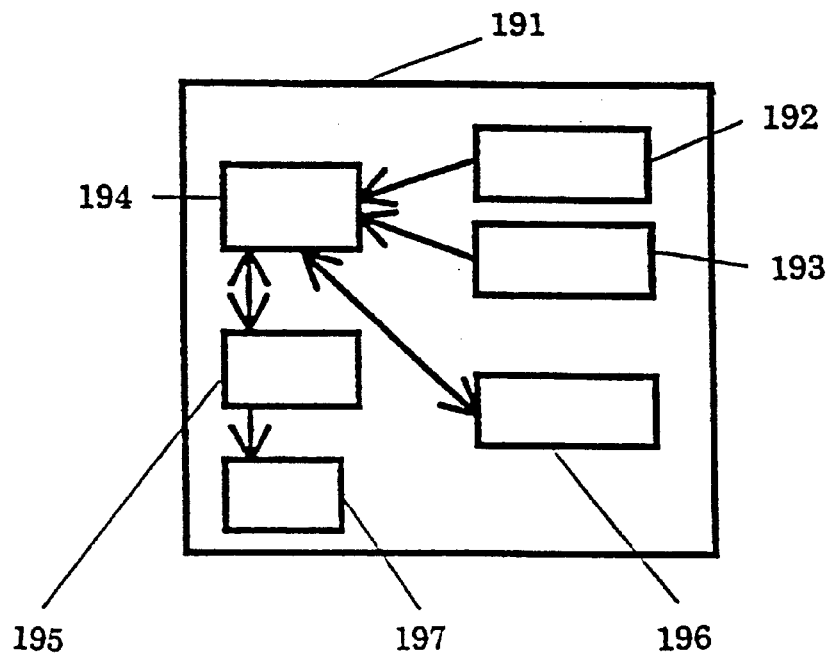
FIG. 58 is a block diagram to show the structure of an ear type thermometer for women in a thirty ninth exemplary embodiment of the present invention.

Subsequently, a description is given to an ear type thermometer for women in a thirty ninth exemplary embodiment of the present invention. FIG. 58 is a block diagram to show the structure of the ear type thermometer for women in the present exemplary embodiment.

The reference numeral 197 is a notifying means to notify the menstruation start date as predicted by the menstruation start date predicting means 195. In addition, the same step reference numerals are used for,the same functions as in the thirty eighth exemplary embodiment. The notifying means 197 comprises a buzzer sounding unit and a liquid crystal display device.

Next, a description is made on how the ear type thermometer for women in the present exemplary embodiment operates with reference to a a block diagram of FIG. 58 and a flow chart of FIG. 57. How the menstruation start date predicting means 195 operates in predicting or correcting menstruation start dates is the same as in the thirty eighth exemplary embodiment. Upon entry of a menstruation start date, predictions are made about future menstruation start dates. At the time of going to Step 18, or when entry of a menstruation start date allows future menstruation start dates to be predicted, a notification to that effect is made by the notifying means 197. More specifically, a beep is sounded from the buzzer sounding unit and a text-based display of the menstruation start dates of next time and thereafter appears on the liquid crystal display device. Also, when there is a change in menstruation start date achieved via the menstruation start date entering means 193, new future menstruation start dates are predicted based on the changed menstruation start date entry and a notification is given accordingly. Further, when a shift from a low temperature range to a high temperature range is confirmed and predictions are corrected accordingly (Step 17) and when predictions are corrected because no entry of a menstruation start date is made even if the predicted menstruation start date is passed and the difference in basal body temperatures between the previous day and the day in high temperature ranges shows the average difference in body temperature or higher (Step 22), future menstruation start dates are still to be notified by the notifying means 197.

Although a notification via the notifying means 197 is made by a buzzer sound and a text-based display on the liquid crystal display device according to the present exemplary embodiment, the same is allowed to be achieved by a voice and also by marking up on the displayed calendar or graph. In addition, when a menstruation start date is entered, the user is allowed to confirm the entry whenever she prefers in addition to the predicted time and corrected time or it does not matter whether the information is made always available by a text-based display and the like. According to the present exemplary embodiment, when a new menstruation start date is predicted, a notification is given actively so as to have the user notice the information rather than only relying on the confirmation made at her convenient time and displaying of the information all the time.

Thus, according to the present exemplary embodiment, an ear type thermometer for women is made available to the user so that she can recognize future menstruation start dates at any time with an excellent prediction accuracy.

(Fortieth Exemplary Embodiment)

Figure 59:
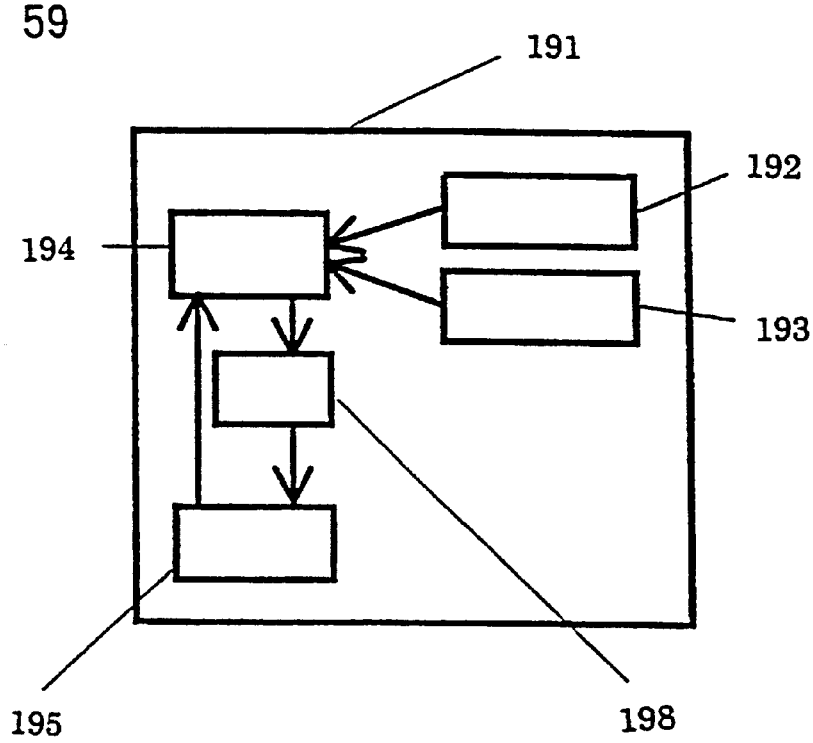
FIG. 59 is a block diagram to show the structure of an ear type thermometer for women in a fortieth exemplary embodiment of the present invention.
Figure 60:
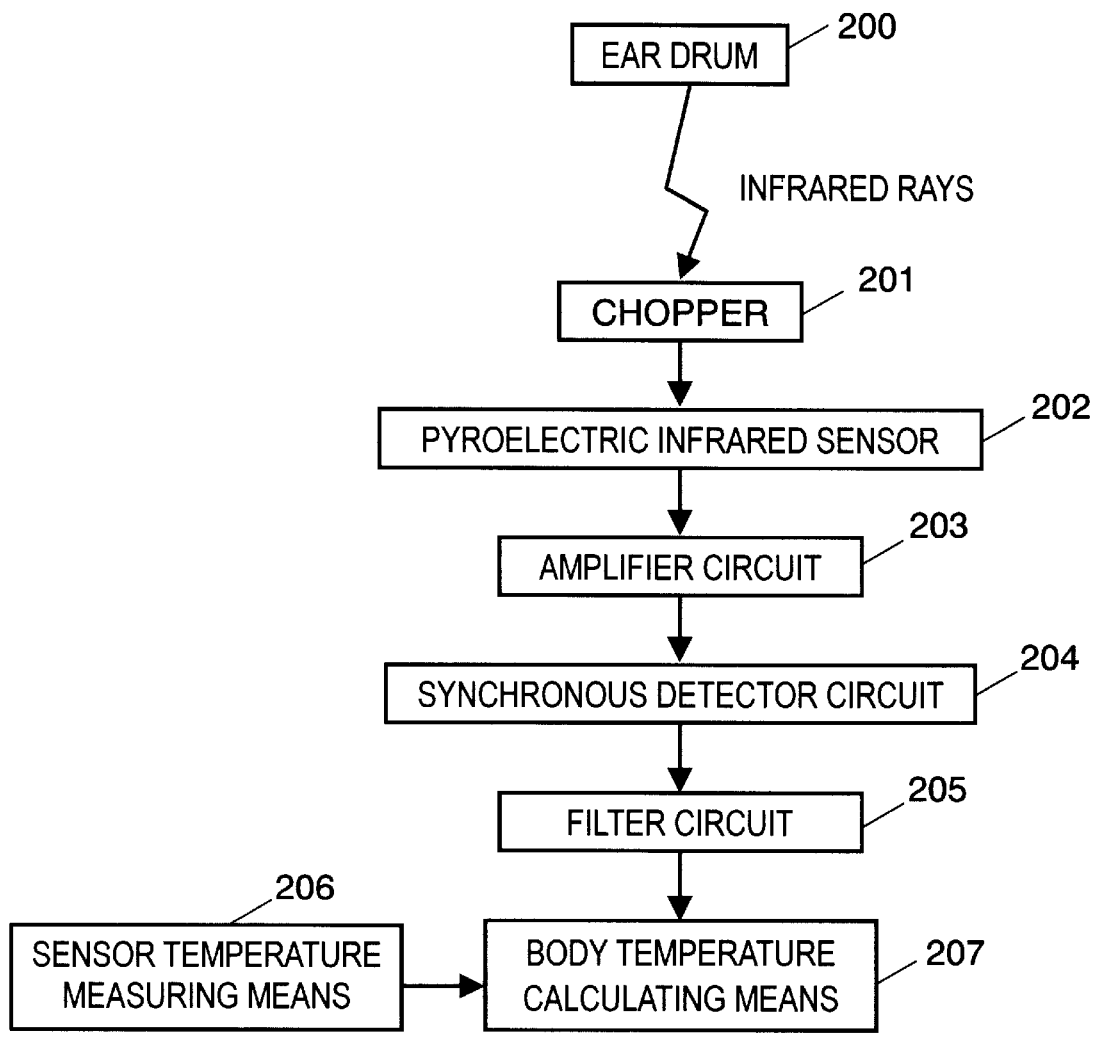
FIG. 60 is a block diagram of a prior art ear type thermometer for women.
Figure 61:
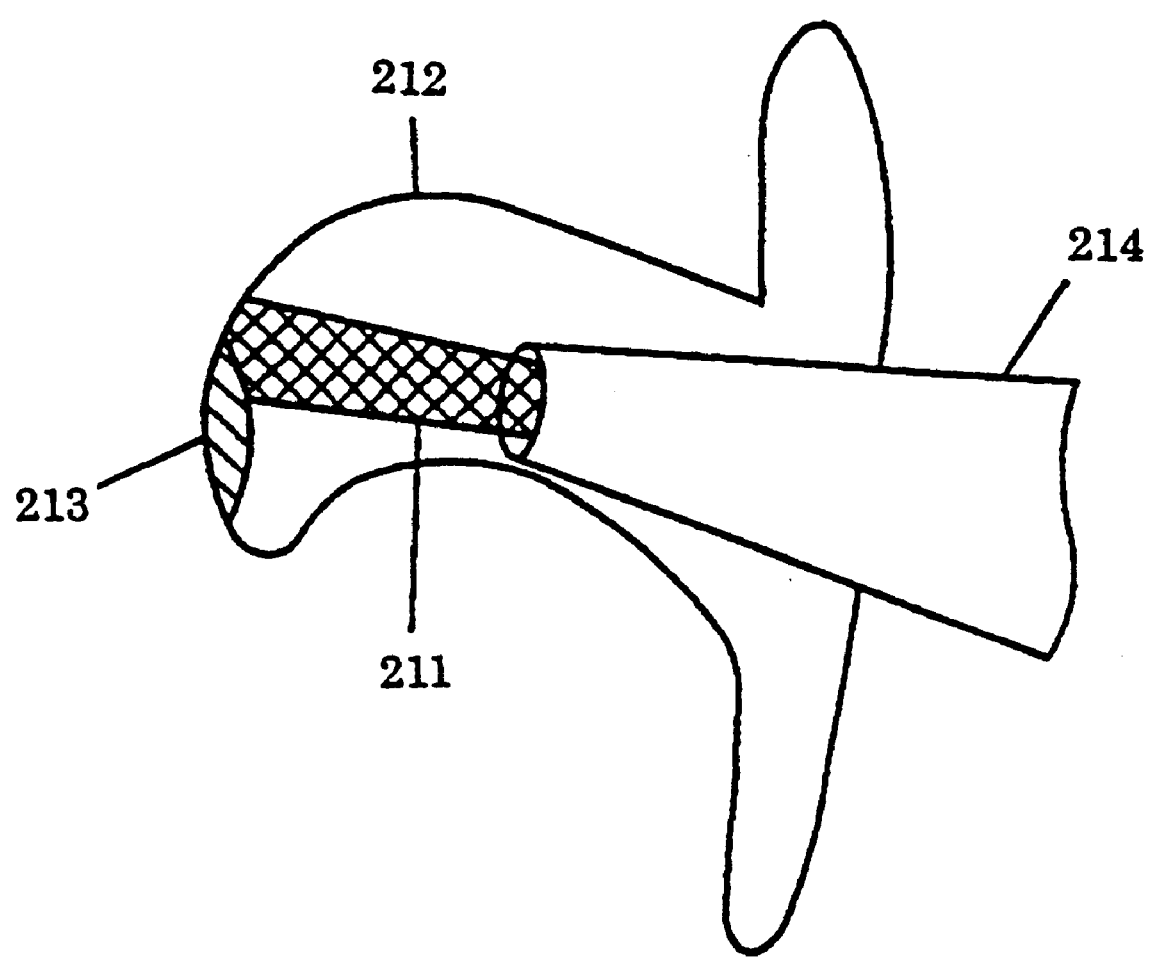
FIG. 61 is a diagram to illustrate the principle of capturing an eardrum temperature in a prior art ear type thermometer for women.
Figure 62:
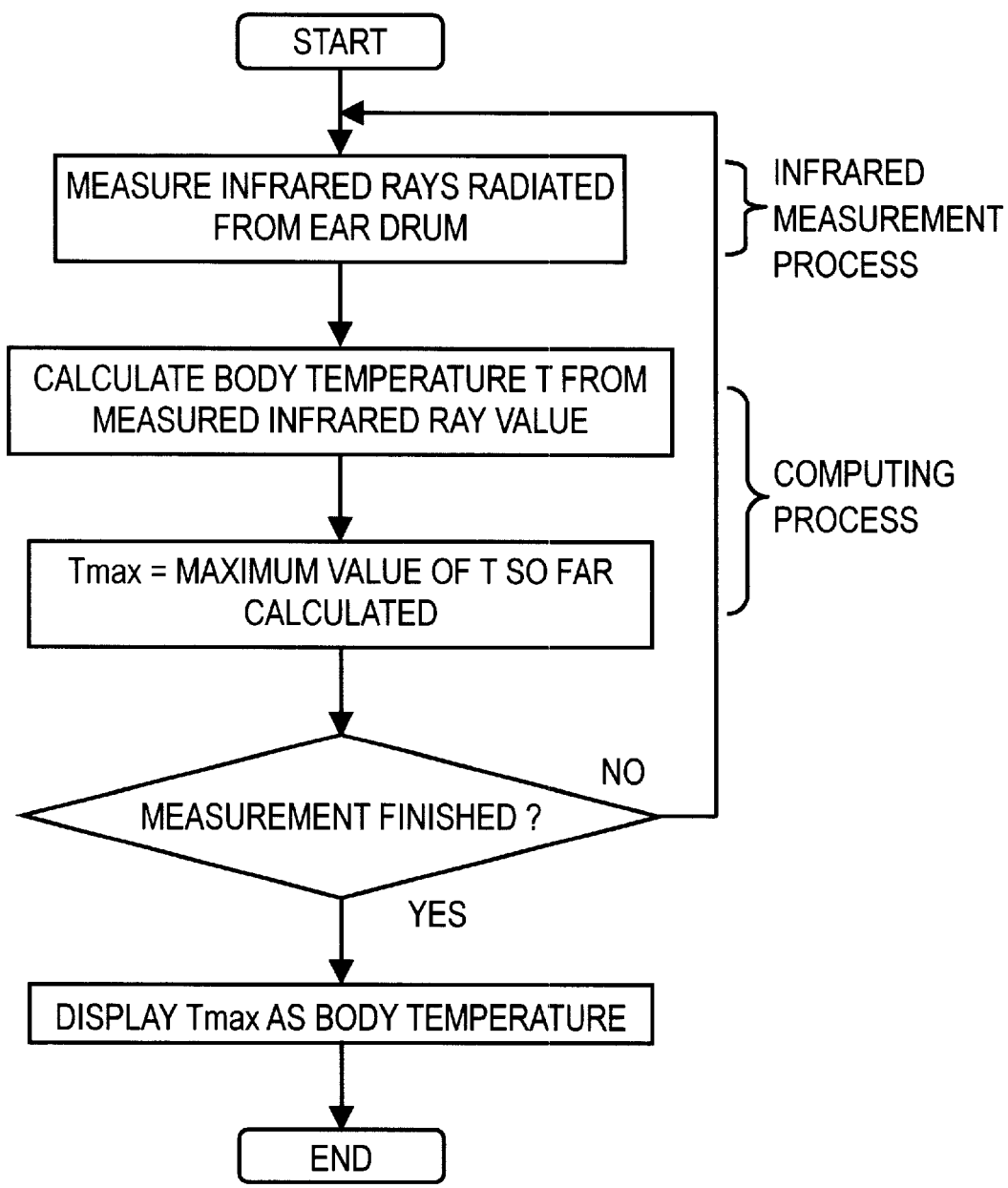
FIG. 62 is a flow chart to show how the prior art ear type thermometer for women of FIG. 61 operates.

Subsequently, a description is given to an ear type thermometer for women in a fortieth exemplary embodiment of the present invention. FIG. 59 is a block digram to show the structure of the ear type thermometer for women in the present exemplary embodiment.

The reference numeral 198 is a storing means restricting means to restrict the data used by the menstruation start date predicting means 195 for predicting future menstruation start dates to only what is available within a predetermined period of one year starting from the present day.

Next, a description is made on how the ear type thermometer for women in the present exemplary embodiment operates with reference to a block diagram of FIG. 59. When a menstruation start date is entered in the menstruation start date entering means 193, the menstruation start date predicting means 195 predicts future menstruation start dates based on the menstruation start dates and basal body temperatures stored in the storing means 194 but what is used for the predictions is restricted by the storing means restricting means 198 to only what is available within a predetermined period of one restarting from the present time out of the menstruation start dates and basal body temperatures stored in the storing means 194. How the process of prediction is performed is the same as in thirty eighth exemplary embodiment.

Although what is handled by the storing means restricting means 198 is restricted to part of what is stored in the storing means 194 according to the present exemplary embodiment, it is also acceptable to restrict the capacity of the storing means 194 to a capacity capable of storing the data involved for a period of one year.

Accordingly, since the conditions of menstruation for women change incessantly according to the growth and aging of the women, the ear type thermometer for women in the present exemplary embodiment allows the accuracy of predicting future menstruation start dates to be enhanced in accordance with the latest changing conditions of menstrual periods.

Industrial Applicability

The present invention relates to a thermometer for measuring temperatures of the object to be measured in temperature by using infrared rays and particularly relates to an ear type thermometer for women.

According to the ear type thermometer for women of the present invention, when a body temperature is measured, the time spent in measuring the body temperature is determined based on a tolerance required of the result of measurement and, therefore, the temperature of an eardrum is allowed to be measured by spending a reasonable length of time that corresponds to a tolerance.

Since the time required to measure a body temperature becomes short when the tolerance is large and conversely the time becomes long when the tolerance is small, there is such an effect as allowing the user to carry out a measurement of body temperatures by freely selecting from between a short measurement time with the priority placed on time and a long measurement time with the priority placed on tolerance. In other words, the tolerance can be determined according to the purpose of use of a thermometer.

The ear type thermometer for women according to the present invention also allows the user to detect the required body temperature promptly without using a large table or relying on a technique for speeding up the hardware's computations. Rather, the present invention aims at deriving a functional value that requires a smaller amount of computations rather than deriving a body temperature by calculation during the course of seeking the body temperature, thereby allowing the functional value to finally derive by calculation the body temperature that is the ultimate measurement value to obtain. In other words, the amount of computations itself required of the calculating process is reduced, thereby enabling the reduction in the computation time required of the calculation process with a net result of reducing the time spent on the body temperature measurement.

The ear type thermometer for women of the present invention has a plurality of replaceable auxiliary probes provided in order to guide the infrared rays inside of the ear hole for the measurement of body temperatures inside of the ear hole and also has a function to check the adaptability of those auxiliary probes, thereby allowing the user to select easily a probe that fits better to the external auditory miatus by coping with the individual differences and to measure the eardrum temperature correctly.

The configuration of a probe used with the ear type thermometer for women according to the present invention is devised so as to reduce contact areas with the external auditory miatus thereby reducing the adverse effect of room temperature imposed on the measurement value. Furthermore, in order to minimize the measurement errors against the respective room temperatures that are different form one another, it is devised to allow the user to obtain a stable measurement result even under a low room temperature by notifying the required continuous measurement times. In addition, it is also devised so as to allow the direction of a probe to be changed when the probe is not properly aligned in the direction of the eardrum.

The ear type thermometer for women of the present invention has a menstruation start date predicting means to predict future menstruation start dates and has a function of eliminating an irregular menstrual period by having the first day of each respective menstrual period, thereby enhancing the accuracy of predicting future menstruation start dates. The ear type thermometer for women also has a function of allowing the user to be helped with a well planed delivery by notifying the ovulation date that is closest to the desired delivery date entered in a desired delivery date entering means.

Accordingly, the present invention has a great effect on enhancement of performance and expansion of functions for a thermometer utilizing infrared rays and particularly for the use as an ear type thermometer for women.

What is claimed is:

1. An ear type thermometer to derive by calculation temperatures of an eardrum based on a measurement value of infrared rays radiated from the eardrum being an object to be measured in temperature, wherein said infrared rays are measured by a method to make a magnitude of an error contained in a measurement value of temperature of the eardrum derived by calculation increase or decrease according to a time spent on measurement.

2. The ear type thermometer according to claim 1 comprising an infrared ray measuring means to measure infrared rays radiated from an eardrum acting as an object to be measured in temperature by a method to make a magnitude of an error contained in a measurement value vary according to a time spent on measurement;
   a tolerance instructing means to instruct about a tolerance on a result of temperature measurement;
   a measurement time determining means to determine a time spent on infrared measurement for the infrared ray measuring means based on a tolerance instructed by the tolerance instructing means; and
   a body temperature calculating means to derive by calculation temperatures of an eardrum acting as an object to be measured in temperature based on a result of infrared measurement carried out by the infrared ray measuring means.

3. The ear type thermometer according to claim 2, wherein the tolerance instructing means is structured so as to instruct about a probability tolerance on a result of temperature measurement.

4. The ear type thermometer according to claim 2, wherein a time of infrared measurement determined by the measurement time determining means is in a simple decreasing relation with the tolerance instructed by the tolerance instructing means.

5. The ear type thermometer according to claim 4, wherein the infrared ray measuring means is provided with a plurality of filter circuits for smoothing measurement values of infrared rays, each respective filter circuit having a time constant different from one another, and also provided with a selection function of a filter circuit to be used according to the tolerance instructed by the tolerance instructing means.

6. The ear type thermometer according to claim 4, wherein a time of infrared measurement determined by the measurement time determining means is inversely proportional to the value expressed by a quadratic equation of the tolerance instructed by the tolerance instructing means.

7. The ear type thermometer according to claim 6, wherein a time of infrared measurement determined by the measurement time determining means is inversely proportional to a square of the tolerance instructed by the tolerance instructing means.

8. The ear type thermometer according to claim 6, wherein the time of infrared measurement determined by the measurement time determining means is inversely proportional to a square of a value derived by subtracting a predetermined value from the tolerance instructed by the tolerance instructing means.

9. The ear type thermometer according to claim 4, wherein the tolerance instructing means has a tolerance entering means to enter a tolerance with a numerical value.

10. The ear type thermometer according to claim 4, wherein the tolerance instructing means has a tolerance selecting means to select one tolerance from a plurality of the tolerances determined in advance.

11. The ear type thermometer according to claim 10, wherein the infrared ray measuring means starts an infrared measurement when a tolerance is selected by the tolerance selecting means.

12. The ear type thermometer according to claim 10, further comprising a measurement instructing means to instruct a start of temperature measurement, wherein the infrared ray measuring means starts an infrared measurement when an instruction is received from the measurement instructing means.

13. The ear type thermometer according to claim 10, wherein an object to be measured in temperature is a human body and the tolerance selecting means has a thermometer function selecting means whereby a selection is made whether the ear type thermometer is used as a thermometer for women or as a general purpose thermometer having a larger tolerance than the thermometer for women.

14. The ear type thermometer according to claim 3, wherein the tolerance instructing means is located so as to allow the user to perform an operation thereof whenever necessary.

15. The ear type thermometer according to claim 3, wherein the tolerance instructing means is arranged to be located before shipment so as not to allow the user to perform an operation thereof.

16. An ear type thermometer to derive by calculation body temperatures of an eardrum based on a measurement value of infrared rays radiated from the eardrum, comprising:
   a first computation method for deriving by computation a functional value of a function which is in a simple functional relation with body temperatures and uses a variable derived by executing a summation of a fourth power of an ambient temperature expressed in kelvins (K), under which the ear type thermometer is used, and a value derived by dividing an output voltage of an infrared sensor with a modifier representing sensitivity and temperature characteristics of the infrared sensor; and
   a second compution method for deriving a bi-quadratic root of a value formed by executing a summation of a fourth power of an ambient temperature expressed in kelvins (K), under which the ear type thermometer for women is used, and a value derived by dividing an output voltage of an infrared sensor with a modifier representing sensitivity and temperature characteristics of the infrared sensor,
   wherein a body temperature is derived by computation, employing the second computation method from a use of an output voltage and ambient temperature of the infrared sensor selected based on a magnitude of a value derived by computation via the first computation method.

17. The ear type thermometer according to claim 16, comprising:
a pyroelectric infrared sensor to convert infrared rays radiated from an eardrum to an electrical signal;
a chopper to interrupt periodically infrared rays from the eardrum that are incident on the pyroelectric infrared sensor;
a sampling means to produce an output of a discrete infrared ray data by accepting periodically an electrical signal presented as an output from the pyroelectric infrared sensor;
a first infrared measurement value calculating means to produce a discrete multiplication data as a result of multiplying an output signal of the pyroelectric infrared sensor by a sinusoidal or cosine signal and to derive by calculation a total summation of the discrete multiplication data for every one period of a chopper frequency;
a second infrared measurement value calculating means to derive by calculation an amplitude value of a frequency component of a frequency equaling to the chopper frequency from a discrete infrared ray data obtained as an output of the sampling means by discrete Fourier transform processing;
a first computation method for deriving by calculation a functional value of a function which is in a simple functional relation with body temperatures and uses a variable derived by dividing an output voltage of the infrared sensor with a modifier representing sensitivity and temperature characteristics of the infrared sensor against respective measurement values obtained by carrying out an infrared measurement a plurality of times and derived by calculation via the first infrared measurement value calculating means;
a second computation method for deriving a biquadratic root of a value derived by executing a summation of a fourth power of an ambient temperature expressed in kelvins (K), under which the ear type thermometer is used, and a value derived by dividing an output voltage of the infrared sensor with a modifier representing sensitivity and temperature characteristics of the infrared sensor;
a functional value calculating means to derive by calculation a functional value in accordance with the first computation method;
a functional value selecting means to select one functional value out of a group of functional values derived by calculation via the functional value calculating means based on a magnitude of each respective functional value; and
a body temperature calculating means to derive by calculation body temperatures according to the second computation method, using an amplitude value of a frequency component of a frequency equaling to a chopper frequency derived by calculation via the second infrared measurement value calculating means against a functional value selected by the functional value selecting means.

18. The ear type thermometer according to claim 17, wherein the functional value calculating means derives by calculation a functional value of a function that is in a simple increasing relation with body temperatures and the functional value selecting means selects a functional value with a largest value out of a group of functional values derived by calculation via the functional value calculating means.

19. The ear type thermometer according to claim 17, wherein the functional value calculating means derives by calculation a functional value of a function that is in a simple decreasing relation with body temperatures and the functional value selecting means selects a functional value with a smallest value out of a group of functional values derived by calculation via the functional value calculating means.

20. The ear type thermometer according to claim 17, further comprising a signal value storing means to store an electrical signal obtained by the infrared sensor, wherein the second infrared measurement value calculating means derives by calculation an infrared measurement value corresponding to a functional value selected by the functional value selecting means by using a signal value stored in the signal value storing means after the functional value is selected by the functional value selecting means.

21. The ear type thermometer according to claim 17, wherein a number of taking in times performed to capture an output signal from the infrared sensor, which is necessary for the first infrared measurement value calculating means to derive by calculation infrared measurement values is smaller than a number of taking in times performed to capture an output signal from the infrared sensor, which is necessary for the second infrared measurement value calculating means to derive by calculation infrared measurement values.

22. The ear type thermometer according to claim 17, wherein the functional value calculating means uses a measurement value from the first infrared measurement value calculating means, as is, as a functional value.

23. The ear type thermometer according to claim 17, further comprising a sensor temperature measuring means to measure an operating ambient temperature of the ear type thermometer a smaller number of times than a number of times performed to measure infrared rays by an infrared ray measuring means, wherein the body temperature calculating means corrects and derives by calculation body temperatures by using temperatures measured by the sensor temperature measuring means.

24. The ear type thermometer according to claim 23, wherein the sensor temperature measuring means measures an operating ambient temperature only once for each body temperature to be derived by calculation by the body temperature calculating means.

25. An ear type thermometer comprising:
an infrared ray measuring means to measure a body temperature in an ear hole;
a plurality of interchangeable probes to be inserted in the ear hole and to guide infrared rays radiated from a human body to the infrared ray measuring means;
a probe adaptability determining means; and
a notifying means,
wherein the probe adaptability determining means comprises:
a body temperature comparing means to compare a maximum value or an average value of body temperatures in the ear hole for each of a plurality of the probes with one another, which is obtained as a result of temperature measurements performed a predetermined number of times; and
a body temperature variation determining means to determine an extent of variation in body temperatures in the ear hole for a plurality of the probes obtained as a result of measurements performed a predetermined number of times, thereby determining and notifying adaptability of a probe at least based on results obtained at the body temperature comparing means and body temperature variation determining means.

26. The ear type thermometer according to claim 25, wherein the probe adaptability determining means has a probe identifying means to identify automatically each respective probe of a plurality of the probes when the probes are attached to the infrared ray measuring means and notifies adaptability of the probes identified automatically by the probe identifying means.

27. The ear type thermometer according to claim 25, further comprising:
   a room temperature measuring means to measure a room temperature; and
   a room temperature storing means,
   wherein the room temperature measuring means gives a notification that probe's adaptability is urged to be determined again by using the probe adaptability determining means when a room temperature has turned out to be just below a predetermined value for the first time after the room temperature at a time of measurement carried out by the infrared ray measuring means was stored in the room temperature storing means.

28. The ear type thermometer according to claim 25, further comprising a clocking means,
   wherein the clocking means gives a notification that probe's adaptability is urged to be determined again by using the probe adaptability determining means when a lapse of time measured by the clocking means after the probe adaptability determining means determined and notified probe's adaptability has passed a predetermined time.

29. The ear type thermometer according to claim 25, further comprising:
   an individuals switching means; and
   an adaptability storing means,
   wherein the probe adaptability determining means notifies the latest probe's adaptability determined for each respective individual by using the individuals switching means and so notified.

30. The ear type thermometer according to claim 25, further comprising a menstruation start date entering means,
   wherein the menstruation start date entering means gives a notification that probe's adaptability is urged to be determined again by using the probe adaptability determining means when a menstruation start date is entered.

31. An ear type thermometer with a main body of the ear type thermometer for women comprising:
   an infrared sensor to detect infrared rays;
   a body temperature measuring means to measure body temperatures based on a signal from the infrared sensor;
   a body temperature displaying means to display body temperatures;
   a probe provided on a tip end of the main body of ear type thermometer to be inserted in an ear and to guide infrared rays radiated from a human body to the infrared sensor; and
   a focusing means to focus incident light,
   wherein the probe comprises a raising material.

32. An ear type thermometer comprising:
   a room temperature measuring means to measure room temperatures;
   an infrared ray measuring means to measure body temperatures in an ear hole;
   a continuous measurement times determining means to determine a number of continuous measurement times performed per a measurement in accordance with a room temperature measured by the room temperature measuring means; and
   a notifying means,
   wherein the continuous measurement times determining means notifies a determined number of continuous measurement times to be performed.

33. The ear type thermometer according to claim 32, further comprising a storing means,
   wherein the notifying means notifies a maximum value of body temperatures in an ear hole measured during a period of the continuous measurement times determined by the continuous measurement times determining means.

34. The ear type thermometer according to claim 32, further comprising a clocking means,
   wherein, when a measurement interval of body temperature measurement in an ear hole exceeds a predetermined time period, the continuous measurement times determining means determines again a number of continuous measurement times to be performed at a room temperature at that particular time, and so notifies.

35. The ear type thermometer according to claim 32, further comprising a measurement value variation determining means,
   wherein, when an extent of measurement value variations in body temperature in an ear hole is a predetermined value or more, the continuous measurement times determining means stretches a number of continuous measurement times to be performed.

36. The ear type thermometer according to claim 32, wherein the continuous measurement times determining means notifies about a remaining number of continuous measurement times to be performed every time a measurement is finished.

37. The ear type thermometer according to claim 32, wherein the continuous measurement times determining means gives a notification of alarm when a measurement is about to be ended before reaching a notified number of continuous measurement times.

38. An ear type thermometer comprising:
   a body temperature measurement unit to measure body temperatures; and
   a data processing display device to process data on body temperatures obtained by measurement carried out in the body temperature measurement unit,
   wherein the data processing display device comprises:
      a clocking means with a calendar function;
      a menstruation start date entering means whereby a user enters
      a first day of each respective menstrual period;
      a desired delivery date entering means whereby a user enters a desired delivery date;
      a storing means to store at least the menstruation start date entered by the menstruation start date entering means and data on body temperatures obtained by measurement performed by the body temperature measurement unit so as to allow a measurement date thereof to be identified;
      a controlling means to predict future menstruation start dates and future ovulation dates based on the data stored in the storing means; and a notifying means,
wherein the controlling means notifies the notifying means about an ovulation date that is closest to a date derived by subtracting a normal period of pregnancy from the desired delivery date entered in the desired delivery date entering means,
wherein, if an applicable ovulation date notified at a time when a desired delivery date is entered by the desired delivery date entering means turns out different from a predicted applicable ovulation date according to data as of the aforementioned time and thereafter, the controlling means gives a notification that the applicable ovulation date is changed.

39. An ear type thermometer comprising:
a body temperature measurement unit to measure body temperatures; and
a data processing display device to process data on body temperatures obtained by measurement carried out in the body temperature measurement unit,
wherein the data processing display device comprises:
   a clocking means with a calendar function;
   a menstruation start date entering means whereby a user enters
   a first day of each respective menstrual period;
   a desired delivery date entering means whereby a user enters a desired delivery date;
   a storing means to store at least the menstruation start date entered by the menstruation start date entering means and data on body temperatures obtained by measurement performed by the body temperature measurement unit so as to allow a measurement date thereof to be identified;
   a controlling means to predict future menstruation start dates and future ovulation dates based on the data stored in the storing means; and
   a notifying means,
   wherein the controlling means notifies the notifying means about an ovulation date that is closest to a date derived by subtracting a normal period of pregnancy from the desired delivery date entered in the desired delivery date entering means, and
wherein the controlling means notifies a miscarriage prone period, a secure period and a premature delivery prone period based on an assumption that conception occurred on the notified applicable ovulation date.

40. An ear type thermometer comprising:
an ear type body temperature measurement unit to measure basal body temperatures;
a menstruation start date entering means to enter a first date of each respective menstrual period;
a storing means to store basal body temperatures measured by the body temperature measurement unit, menstruation start dates entered by the menstruation start date entering means and the like; and
a menstruation start date predicting means with a calendar function to predict future menstruation start dates based on data stored in the storing means,
wherein the menstruation start date predicting means derives by calculation an average number of days in valid menstrual periods, eliminating menstrual periods, each of which having a difference in a number of days exceeding a predetermined number of days from an average number of days of menstrual periods, where a number of days of a menstrual period is defined as an interval between menstruation start dates stored in the storing means, and menstrual periods, in which a difference between an average body temperature in high temperature range and an average body temperature in low temperature range for each respective menstrual period is smaller than a predetermined value, and predicts a menstruation start date of n periods in future as (a most recent menstruation start date+n×an average number of days in valid menstrual periods),
wherein the menstruation start date predicting means predicts future menstruation start dates when a number of valid menstrual periods exceeds a predetermined proportion of a total number of menstrual periods that form an object to be predicted.

41. An ear type thermometer comprising:
an ear type body temperature measurement unit to measure basal body temperatures;
a menstruation start date entering means to enter a first date of each respective menstrual period;
a storing means to store basal body temperatures measured by the body temperature measurement unit, menstruation start dates entered by the menstruation start date entering means and the like; and
a menstruation start date predicting means with a calendar function to predict future menstruation start dates based on data stored in the storing means,
wherein the menstruation start date predicting means derives by calculation an average number of days in valid menstrual periods, eliminating menstrual periods, each of which having a difference in a number of days exceeding a predetermined number of days from an average number of days of menstrual periods, where a number of days of a menstrual period is defined as an interval between menstruation start dates stored in the storing means, and menstrual periods, in which a difference between an average body temperature in high temperature range and an average body temperature in low temperature range for each respective menstrual period is smaller than a predetermined value, and predicts a menstruation start date of n periods in future as (a most recent menstruation start date+n×an average number of days invalid menstrual periods),
wherein, when a shift from a low temperature range to a high temperature range can be determined to have taken place according to a basal body temperature measured by the ear type body temperature measurement unit, the menstruation start date predicting means makes a modifying prediction that a next menstruation start date is a date derived by adding an average number of days in a high temperature range calculated from a basal body temperature of each respective menstrual period stored in the storing means to a day before a first day of a high temperature range.

42. An ear type thermometer comprising:
an ear type body temperature measurement unit to measure basal body temperatures;
a menstruation start date entering means to enter a first date of each respective menstrual period;
a storing means to store basal body temperatures measured by the body temperature measurement unit, menstruation start dates entered by the menstruation start date entering means and the like; and
a menstruation start date predicting means with a calendar function to predict future menstruation start dates based on data stored in the storing means,
wherein the menstruation start date predicting means derives by calculation an average number of days in valid menstrual periods, eliminating menstrual periods, each of which having a difference in a number of days exceeding a predetermined number of days from an average number of days of menstrual periods, where a number of days of a menstrual period is defined as an interval between menstruation start dates stored in the storing means, and menstrual periods, in which a difference between an average body temperature in high temperature range and an average body temperature in low temperature range for each respective menstrual period is smaller than a predetermined value, and predicts a menstruation start date of n periods in future as (a most menstruation start date+n×an average number of days in valid menstrual periods), and further comprising a body temperature difference calculating means to derive by calculation an average difference in body temperature between a menstruation start date and a day before the menstruation start date based on basal body temperatures and menstruation start dates stored in the storing means, wherein, when there is no entry of a menstruation start date in the menstruation start date entering means even after a predicted next menstruation start date is passed, the menstruation start date predicting means makes a modifying prediction that a next menstruation start date is a day when a basal body temperature measured by the ear type body temperature measurement unit is found to have exceeded a basal body temperature of a previous day plus a difference in body temperature derived by calculation by the body temperature difference calculating means.

* * * * *